US012643929B2

(12) United States Patent　　　　(10) Patent No.: US 12,643,929 B2
O'Shea et al.　　　　　　　　　　　(45) Date of Patent:　　Jun. 2, 2026

(54) GENETICALLY ENCODED FLUORESCENT-IRON FERRITIN NANOPARTICLE PROBES FOR DETECTING AN INTRACELLULAR TARGET BY FLUORESCENT AND ELECTRON MICROSCOPY

(71) Applicant: Salk Institute for Biological Studies, La Jolla, CA (US)

(72) Inventors: Clodagh O'Shea, San Diego, CA (US); Jingwen Yin, La Jolla, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 1453 days.

(21) Appl. No.: 16/900,275

(22) Filed: Jun. 12, 2020

(65) Prior Publication Data

US 2020/0308239 A1　　Oct. 1, 2020

Related U.S. Application Data

(63) Continuation of application No. PCT/US2018/065533, filed on Dec. 13, 2018.

(60) Provisional application No. 62/598,937, filed on Dec. 14, 2017.

(51) Int. Cl.
| | |
|---|---|
| *C12Q 1/68* | (2018.01) |
| *C07K 7/64* | (2006.01) |
| *C07K 14/47* | (2006.01) |
| *C12N 9/02* | (2006.01) |
| *C12P 19/34* | (2006.01) |
| *C12Q 1/6876* | (2018.01) |
| *G01N 33/50* | (2006.01) |
| *G01N 33/58* | (2006.01) |
| *G01N 33/68* | (2006.01) |

(52) U.S. Cl.
CPC ............... *C07K 14/47* (2013.01); *C07K 7/64* (2013.01); *C12N 9/0091* (2013.01); *C12Q 1/6876* (2013.01); *C12Y 116/03001* (2013.01); *G01N 33/5035* (2013.01); *G01N 33/582* (2013.01); *G01N 33/6803* (2013.01); *C07K 2319/33* (2013.01); *C07K 2319/40* (2013.01); *C07K 2319/735* (2013.01); *C07K 2319/80* (2013.01); *G01N 2458/00* (2013.01)

(58) Field of Classification Search
CPC combination set(s) only.
See application file for complete search history.

(56) References Cited

U.S. PATENT DOCUMENTS

| | | | |
|---|---|---|---|
| 2011/0201112 A1* | 8/2011 | Rome ................. | C12N 9/1077 435/375 |
| 2013/0142732 A1 | 6/2013 | Lee et al. | |
| 2014/0302527 A1 | 10/2014 | Lee et al. | |

FOREIGN PATENT DOCUMENTS

| | | | |
|---|---|---|---|
| WO | WO 2013/029025 | 2/2013 | |
| WO | WO 2016/049031 | 3/2016 | |
| WO | WO-2016168594 A1 * | 10/2016 | ......... C07K 16/1063 |

OTHER PUBLICATIONS

Wang, Qing, Christopher P. Mercogliano, and Jan Löwe. "A ferritin-based label for cellular electron cryotomography." Structure 19.2 (2011): 147-154. (Year: 2011).*
Orino, K. et al. "Sequence analysis of canine and equine ferritin H and L subunit cDNAs", DNA Sequence, Feb. 2005; 16(1): 58-64 (Year: 2005).*
Bhaskar Barnwal, et al. "A monoclonal antibody binds to threonine 49 in the non-structural 1 protein of influenza A virus and interferes with its ability to modulate viral replication" Antiviral Research, vol. 116, Apr. 2015, pp. 55-61 (Year: 2015).*
Rothbauer U, Zolghadr K, Tillib S, Nowak D, Schermelleh L, Gahl A, Backmann N, Conrath K, Muyldermans S, Cardoso MC, Leonhardt H. Targeting and tracing antigens in live cells with fluorescent nanobodies. Nat Methods. Nov. 2006;3(11):887-9 (Year: 2006).*
Georges Schwalbach, et al. "Production of Fluorescent Single-Chain Antibody Fragments in *Escherichia coli*" Protein Expression and Purification, vol. 18, Issue 2, Mar. 2000, pp. 121-132 (Year: 2000).*
Ido Golding et al. "RNA dynamics in live *Escherichia coli* cells" Proc Natl Acad Sci U S A, Aug. 3, 2004;101(31):11310-5 (Year: 2004).*
José Rino, et al. Imaging dynamic interactions between spliceosomal proteins and pre-mRNA in living cells, Methods vol. 65, Issue 3, Feb. 2014, pp. 359-366 (Year: 2014).*
Foruem question thread from https://www.researchgate.net/post/Expression-of-prokaryote-genes-in-eukaryotes (2012). (Year: 2012).*
"FerriTag: A Genetically-Encoded Inducible Tag for Correlative Light-Electron Microscopy", Nicholas I. Clarke, et al., from bioRxiv 095208; Posted Dec. 18, 2016, https://www.biorxiv.org/content/10.1101/095208v1. (Year: 2016).*
Caihong Jiang, et al. "Ferritin-EGFP Chimera as an Endogenous Dual-Reporter for Both Fluorescence and Magnetic Resonance Imaging in Human Glioma U251 Cells", Tomography. Mar. 2017;3(1):1-8. (Year: 2017).*
Giuliano Bellapadrona et al "Supramolecular Protein Assemblies in the Nucleus of Human Cells" Angewandte Chemie, vol. 53, Issue 6, Feb. 3, 2014 (Year: 2014).*
Bellapadrona and Elbaum, "Supramolecular Protein Assemblies in the Nucleus of Human Cells," *Angew Chem Int Ed Engl.* 53.6: 1534-1537, Feb. 2014.

(Continued)

*Primary Examiner* — Stephen T Kapushoc
(74) *Attorney, Agent, or Firm* — KLARQUIST SPARKMAN, LLP

(57)　　　　　　ABSTRACT

Disclosed are probes that are expressed in a cell to label an intracellular target (such as protein or DNA) for both light and electron microscopy. The probes comprise a targeting domain that specifically binds to the intracellular target, a detection tag that can be used to detect the intracellular location of the probe using light microscopy, and a ferritin nanoparticle ferritin nanoparticle with ferroxidase activity and that stores ferric oxide. Also disclosed are nucleic acids encoding the fusion proteins and methods of their use.

30 Claims, 26 Drawing Sheets

Specification includes a Sequence Listing.

(56)  References Cited

OTHER PUBLICATIONS

International Search Report and Written Opinion Issued in PCT/US2018/065533, ISA Australian Patent Office, mailed on Mar. 5, 2019 (10 pages).

Kim et al., "In Vivo Imaging of Tumor Transduced with Bimodal Lentiviral Vector Encoding Human Ferritin and Green Fluorescent Protein on a 1.5T Clinical Magnetic Resonance Scanner," *Cancer Res. 70.18*: 7316-7324, Sep. 2010.

Ou et al., "ChromEMT: Visualizing 3D Chromatin Structure and Compaction in Interphase and Mitotic Cells," *Science* 357.6349: eaag0025, Jul. 2017 (32 pages).

EBI Accession No. UNIPROT:Q8MIP0, "RecName: Full=Ferritin heavy chain; Short=Ferritin H subunit; EC=1.16.3.1; Contains: RecName: Full=Ferritin heavy chain, N-terminally processed;" Database UniProt, Oct. 17, 2006 (https://www.uniprot.org/uniprot/Q8MIP0.txt).

* cited by examiner

FIG. 1A

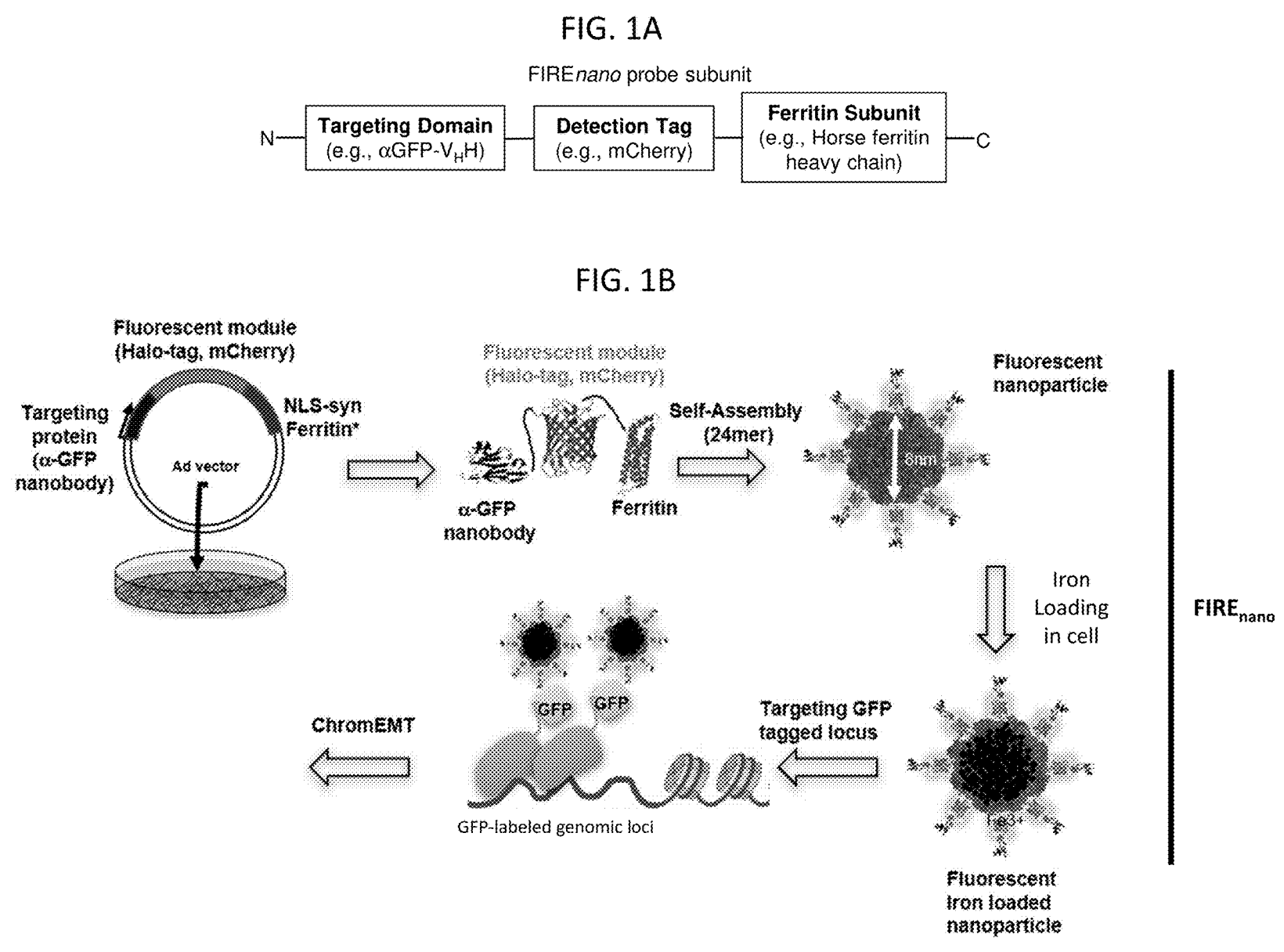

FIRE*nano* probe subunit

| Targeting Domain (e.g., αGFP-V$_H$H) | Detection Tag (e.g., mCherry) | Ferritin Subunit (e.g., Horse ferritin heavy chain) |
|---|---|---|

ORF3-GFP     αGFPV$_H$H-mCherry-*E.coli* ferritin

TRF1-GFP     αGFPV$_H$H-mCherry-*E.coli* ferritin

LacI-GFP     αGFPV$_H$H-mCherry-*E.coli* ferritin

CX43-GFP     αGFPV$_H$H-mCherry-*E.coli* ferritin     DAPI/Merge

αGFPV_HH-mCherry-*E.coli* ferritin

TRF1-GFP

DAPI

Fluorescence

Correlated light/TEM

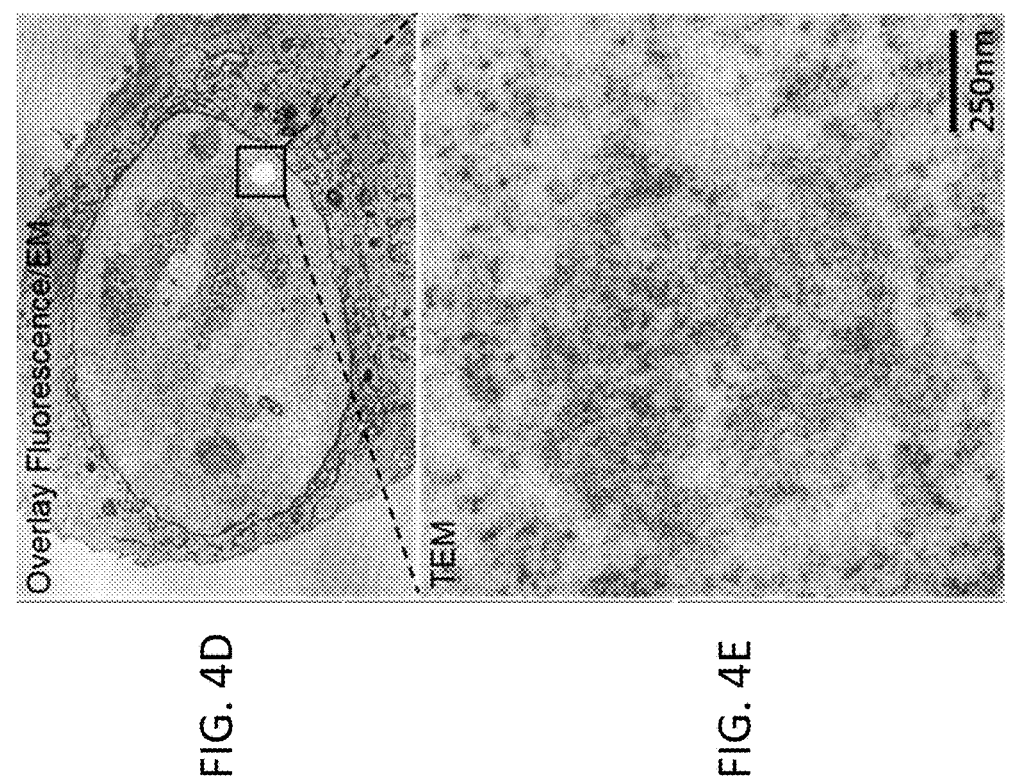
FIG. 4D
FIG. 4E
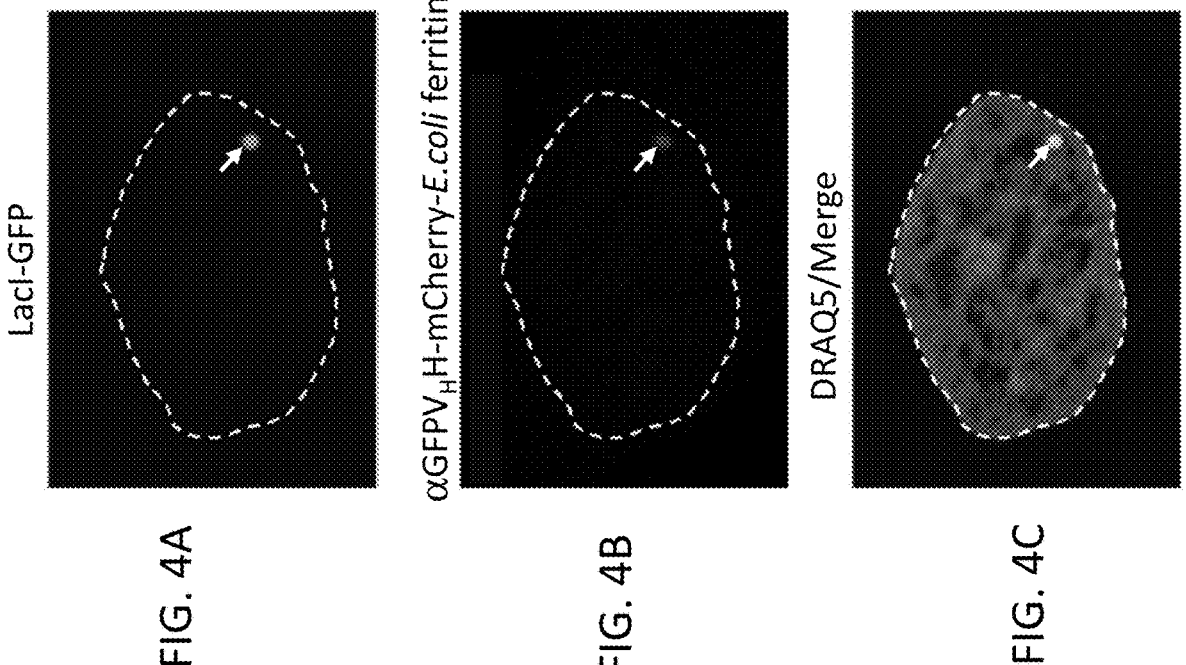
FIG. 4A
FIG. 4B
FIG. 4C

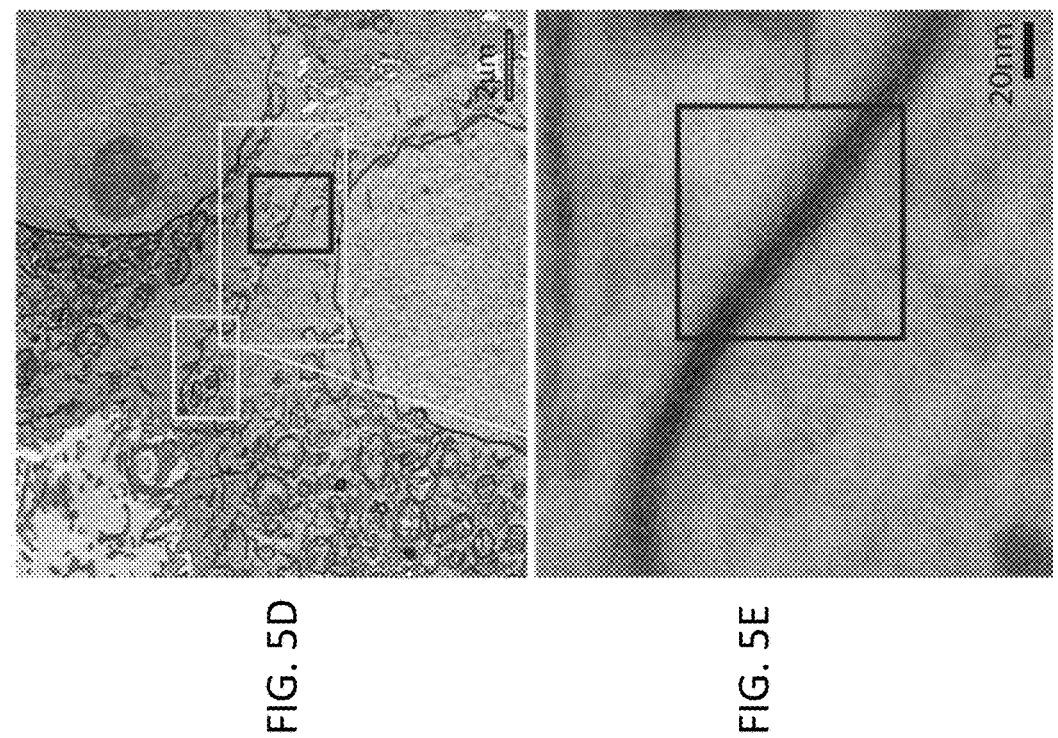
FIG. 5D
FIG. 5E
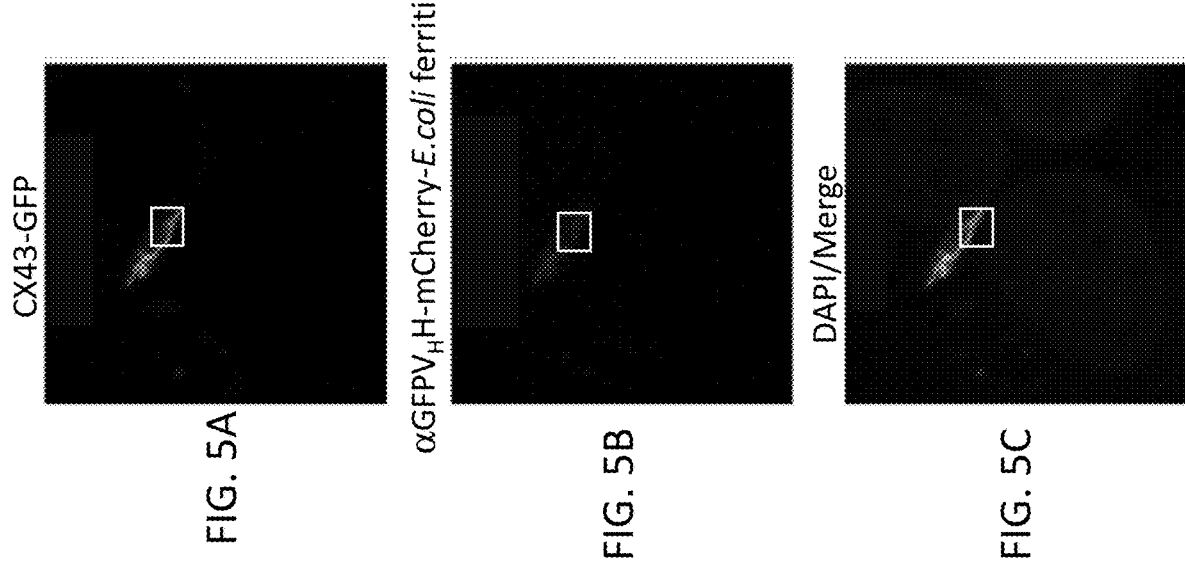
CX43-GFP
FIG. 5A
αGFPV$_H$-mCherry-*E.coli* ferritin
FIG. 5B
DAPI/Merge
FIG. 5C

| | | | | |
|---|---|---|---|---|
| 1 | FLAG | NLS | FKBP | Halo | Horse ferritin |
| 2 | FLAG | NLS | MS2 | Halo | Horse ferritin |
| 3 | FLAG | NLS | αGFPV$_H$H | mCherry | Horse ferritin |
| 4 | FLAG | NLS | αGFPV$_H$H | Halo | Horse ferritin |

Native gel

Prussian blue staining

Native gel

Silver staining

Denaturing gel

Anti-FLAG

Anti-β-actin

Horse spleen ferritin

10sec 2%UA    Unstained    2min 1%Osmium

FLAG-NLS-αGFPV$_H$H-horse ferritin

10sec 2%UA    Unstained    2min 1%Osmium

FLAG-NLS-αGFPV$_H$H-horse ferritin

Cryo-EM

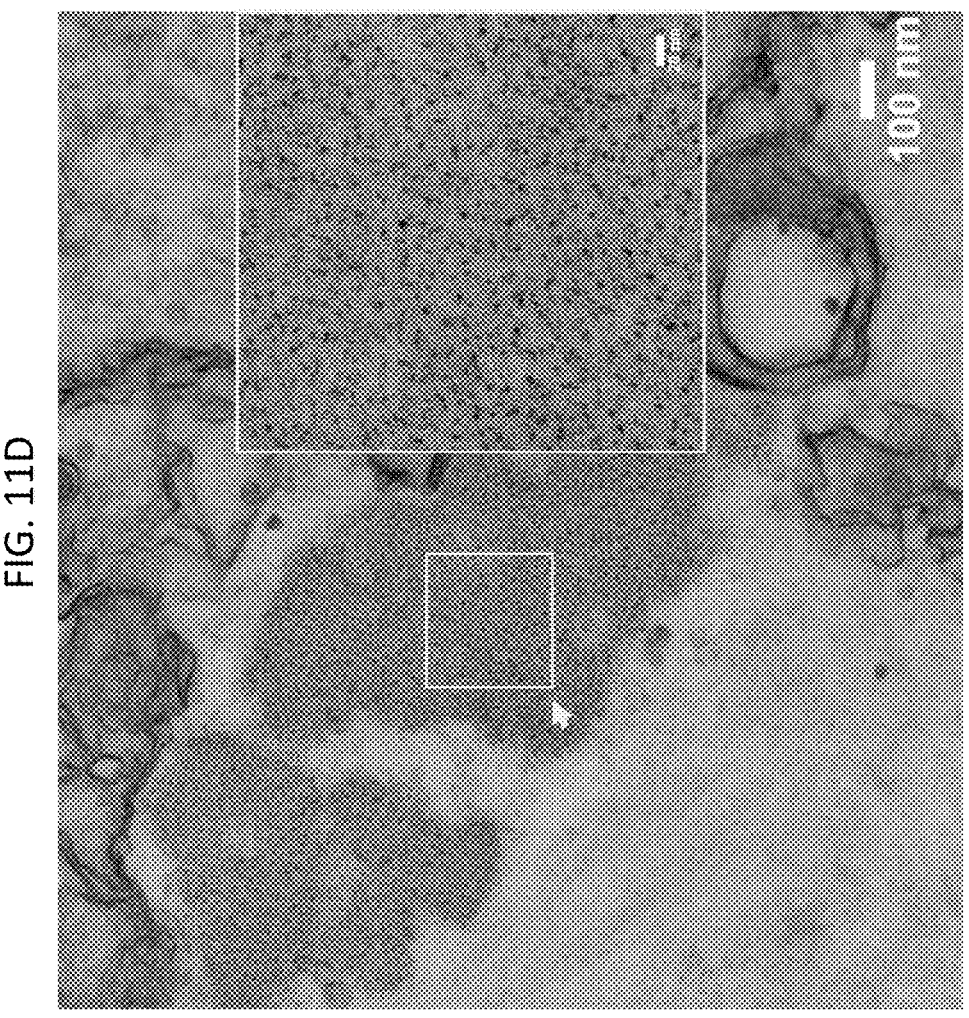
FIG. 11D
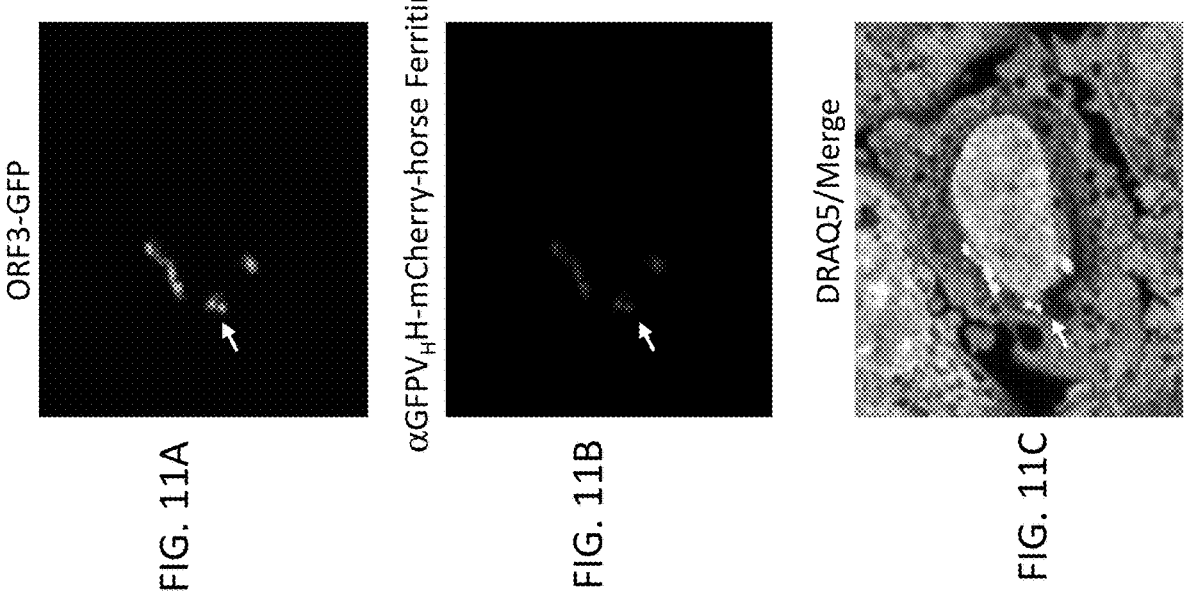
ORF3-GFP
FIG. 11A
αGFPV$_H$H-mCherry-horse Ferritin
FIG. 11B
DRAQ5/Merge
FIG. 11C

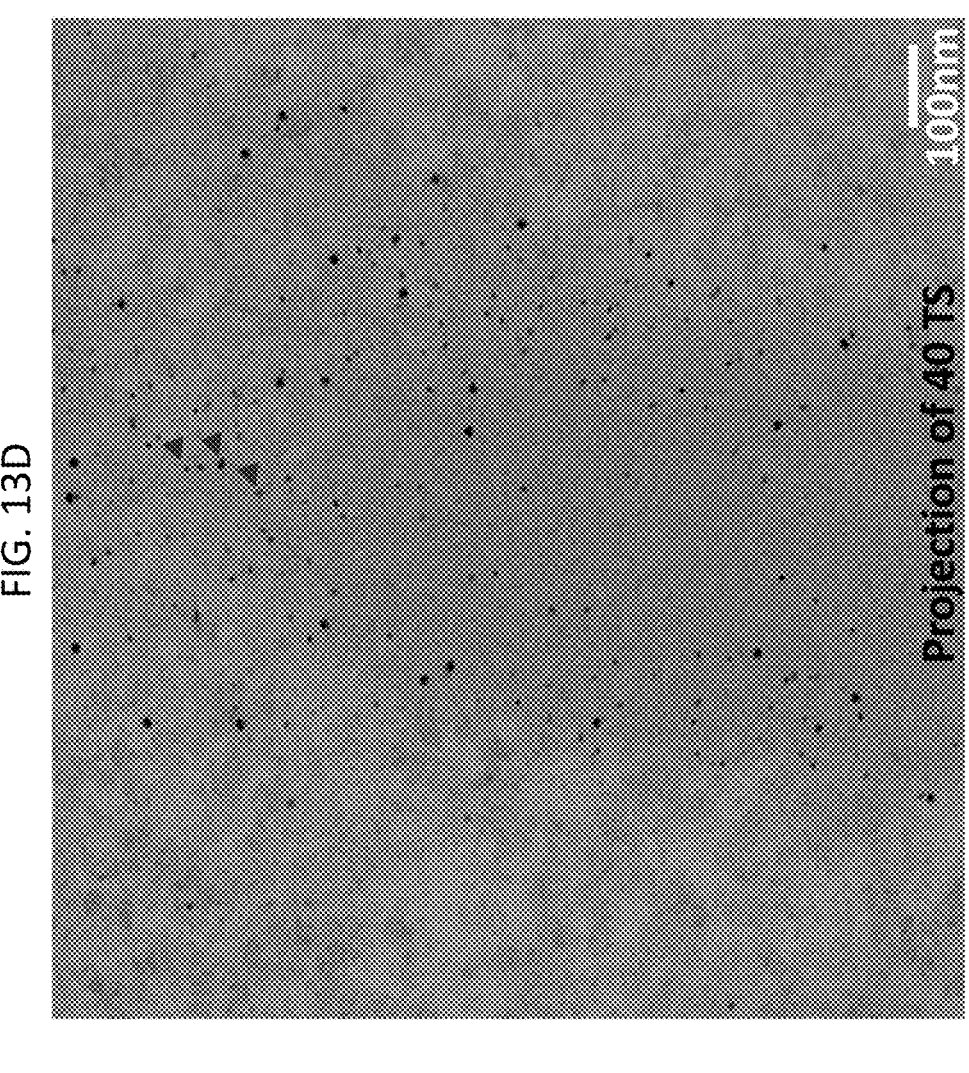
FIG. 13D
Projection of 40 TS
100nm
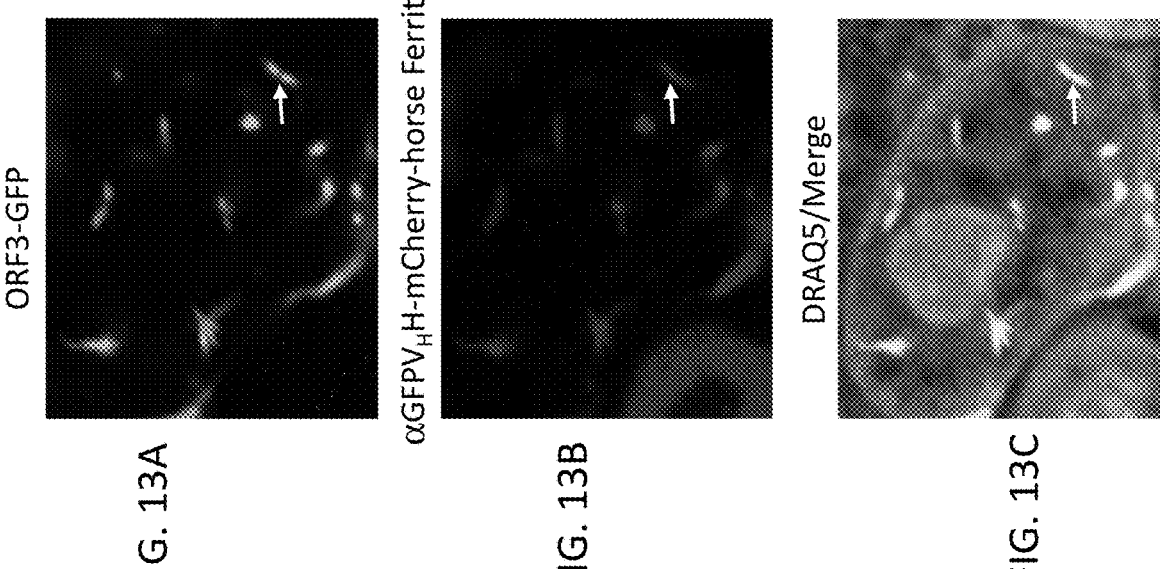
ORF3-GFP
FIG. 13A
αGFPV$_H$H-mCherry-horse Ferritin
FIG. 13B
DRAQ5/Merge
FIG. 13C

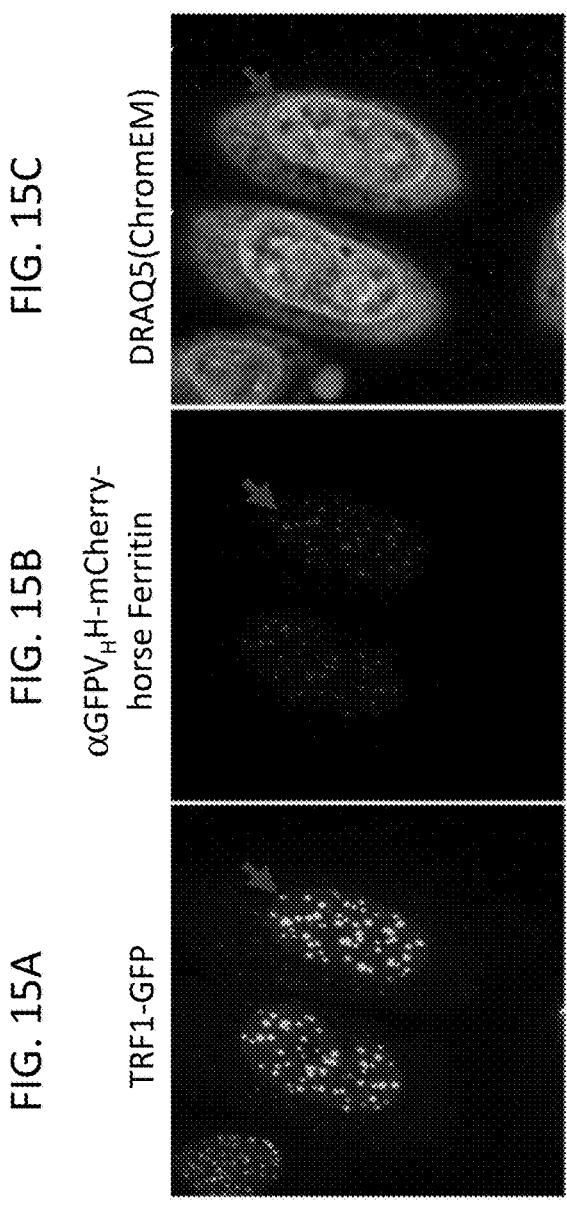
FIG. 15C
DRAQ5(ChromEM)
FIG. 15B
αGFPV$_H$H-mCherry-
horse Ferritin
FIG. 15A
TRF1-GFP
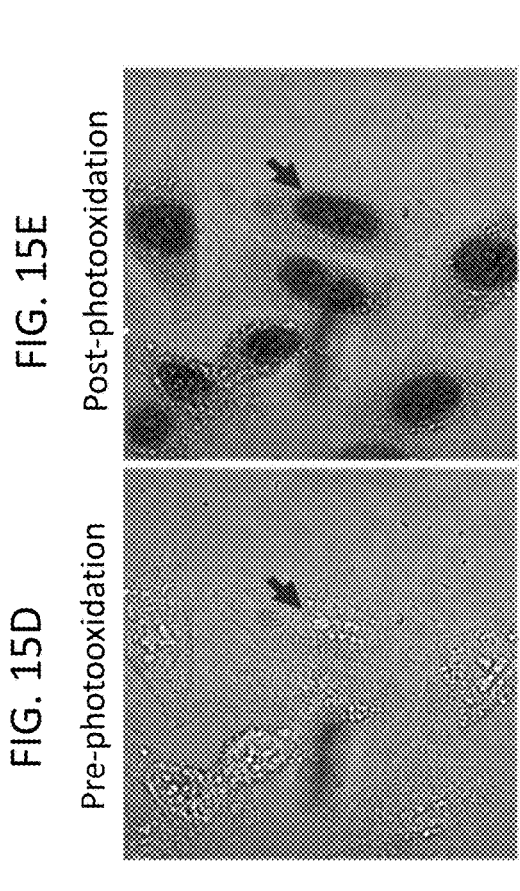
FIG. 15E
Post-photooxidation
FIG. 15D
Pre-photooxidation

LacI-GFP    αGFPV$_H$H-mCherry-horse ferritin    DRAQ5/Merge

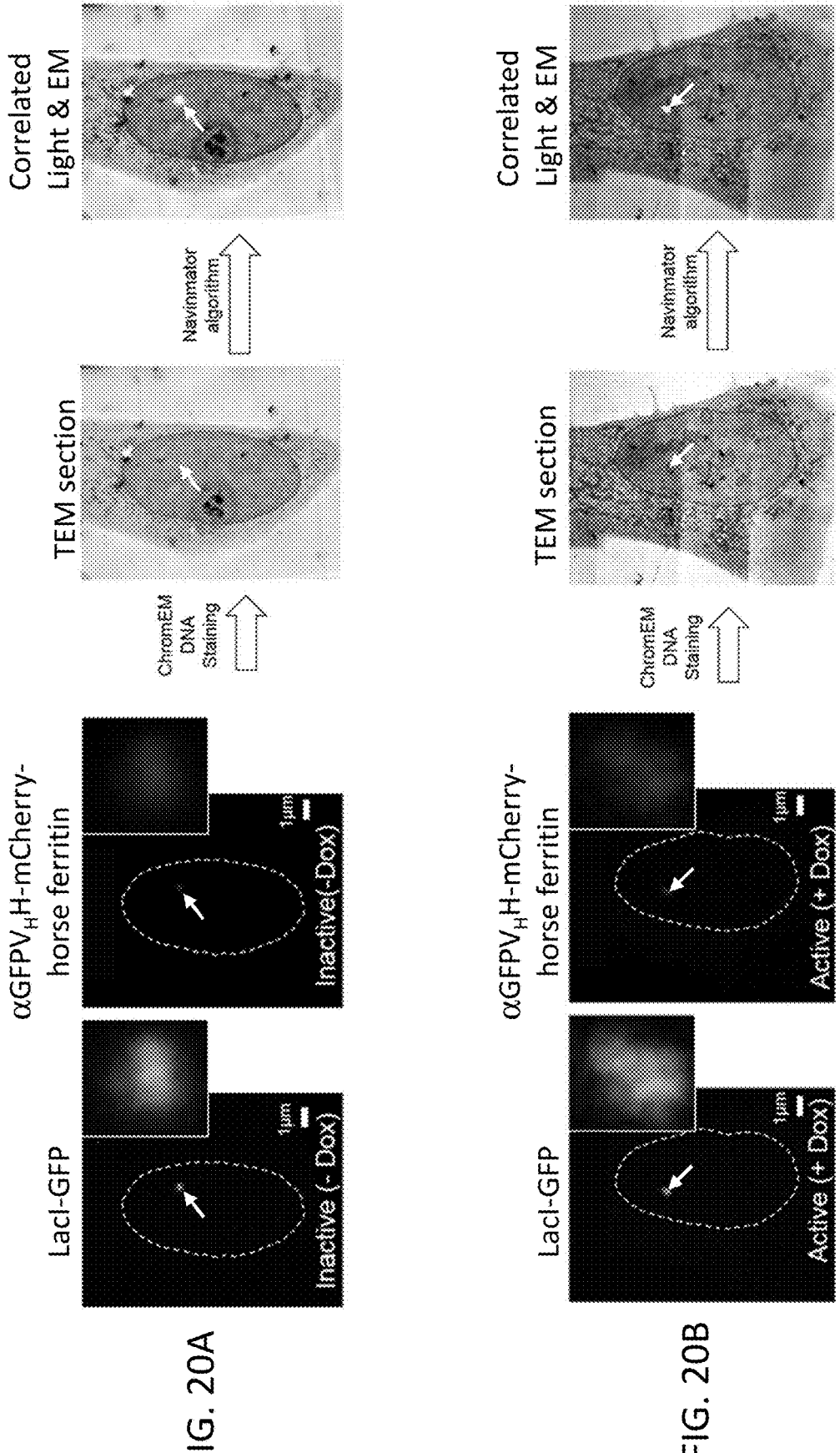

αGFPV$_H$H-mCherry-horse ferritin

TS #61

100 slices projection

Ferritin distribution

αGFPvₕH-mCherry-
horse ferritin

TS #39

100 slices projection

Ferritin distribution

SEQUENCE LISTING

```
<160> NUMBER OF SEQ ID NOS: 45

<210> SEQ ID NO 1
<211> LENGTH: 1677
<212> TYPE: DNA
<213> ORGANISM: Artificial Sequence
<220> FEATURE:
<223> OTHER INFORMATION: Recombinant ferritin sequence

<400> SEQUENCE: 1
atgcccaaaa agaagaggaa agtgggatcg ggtatggcag atgttcaatt ggtagaaagt      60
ggtggagcac tcgtacagcc tggtggttct cttcgactgt catgcgcagc ttcaggattt     120
ccagtgaata gatatagtat gagatggtat agacaagccc ctggaaaaga aagagagtgg     180
gtggccggaa tgtcctcagc cggagataga agtagttatg aagatagtgt taaaggacga     240
tttacaattt caagagatga tgcaagaaat acagtttacc tccaaatgaa tagtcttaaa     300
```

```
cctgaagata cagcagttta ttattgtaat gttaacgtgg gattcgaata ctggggtcag      360
ggaacacaag taacggtaag tagcggttca ggctggagcc acccgcagtt cgaaaaagga      420
tccgggcatc accatcatca ccacggatcc gggcccaaga aaaagcgcaa ggtaatggtg      480
agcaagggcg aggaggataa catggccatc atcaaggagt tcatgcgctt caaggtgcac      540
atggagggct ccgtgaacgg ccacgagttc gagatcgagg gcgagggcga gggccgcccc      600
tacgagggca cccagaccgc caagctgaag gtgaccaagg gtggccccct gcccttcgcc      660
tgggacatcc tgtcccctca gttcatgtac ggctccaagg cctacgtgaa gcaccccgcc      720
gacatccccg actacttgaa gctgtccttc cccgagggct tcaagtggga gcgcgtgatg      780
aacttcgagg acggcggcgt ggtgaccgtg acccaggact cctccctgca ggacggcgag      840
ttcatctaca aggtgaagct gcgcggcacc aacttcccct ccgacggccc cgtaatgcag      900
aagaagacca tgggctggga ggcctcctcc gagcggatgt accccgagga cggcgccctg      960
aagggcgaga tcaagcagag gctgaagctg aaggacggcg ccactacga cgctgaggtc     1020 aagaccacct acaaggccaa gaagcccgtg cagctgcccg gcgcctacaa cgtcaacatc     1080
aagttggaca tcacctccca caacgaggac tacaccatcg tggaacagta cgaacgcgcc     1140
gagggccgcc actccaccgg cggcatggac gagctgtaca agggatccgg ctcaggatct     1200
atgaagggcg acaccaaggt catcaactac ctgaacaagt tgctggggaa cgaactcgtg     1260
gccatcaacc agtacttcct gcacgcacgc atgttcaaga actggggcct gaagcgcctg     1320
aacgatgtgg agtaccacga gtccatcgac gagatgaagc acgccgatag atacatcgag     1380
cggattctgt ttctggaagg acttccgaat ttgcaagacc tggggaagct gaatatcgga     1440
gaggatgtgg aggaaatgct gagaagcgac ctcgcgctgg aacttgatgg tgccaagaac     1500
ctcagggaag ccattggata cgctgactcg gtgcacgact acgtgtcacg ggacatgatg     1560
atcgagatcc tgcgcgacga agaaggccac attgactggc tcgaaactga gctggacctg     1620
atccagaaga tgggactcca gaactatctg caagcgcaga ttcgggaaga gggttaa      1677
```

```
<210> SEQ ID NO 2
<211> LENGTH: 603
<212> TYPE: DNA
<213> ORGANISM: Artificial Sequence
<220> FEATURE:
<223> OTHER INFORMATION: Recombinant ferritin sequence

<400> SEQUENCE: 2
atggactaca aggaccacga tggtgattat aaggatcatg atatagacta taaggacgac       60
gacgacaagg gaggagggtc cggcggcgga agtggcggtg gctcaatgtt gaaacctgag      120
atgattgaga aacttaatga acagatgaat ttggaacttt acagttcctt gttgtatcag      180
caaatgagtg cttggtgcag ctatcatacg tttgagggtg cggcagcgtt cttgcggagg      240
catgcgcagg aggaaatgac ccacatgcag agactttttg attacctcac tgataccgga      300
aatcttcctc gaatcaacac ggtagaaagc cctttcgccg aatatagtag cttggacgag      360
ctgtttcaag aaacgtacaa acacgagcag ctcatcacac agaagataaa tgagctggct      420
catgctgcaa tgaccaatca agactaccct acatttaact ttctgcagtg gtatgtgagt      480
gaacaacacg aagaagagaa actgttcaaa tctattattg ataaacttag tctcgctggt      540
aagtccggtg agggtttgta tttcatagac aaagaactct ccactcttga tacccagaac      600
taa                                                                     603
```

```
<210> SEQ ID NO 3
<211> LENGTH: 549
<212> TYPE: DNA
<213> ORGANISM: Artificial Sequence
<220> FEATURE:
<223> OTHER INFORMATION: horse ferritin heavy chain

<400> SEQUENCE: 3
atgactaccg cttttccctc ccaagttagg caaaattacc atcaagacag cgaagctgct      60
atcaaccgcc agatcaatct tgagctccac gcttcctatg tctatctgtc tatgtccttt     120
tattttgata gagatgacgt cgcactgaag aacttcgcta agtacttcct gcatcagagt     180
cacgaggaaa gggagcacgc tgaaaagctt atgaaactgc aaaatcaacg gggggggcgc     240
atcttccttc aggatataaa aaagcctgac caagatgact gggagaacgg cctcaaggct     300
atggaatgcg ctctccatct ggagaagaac gtaaatgagt ctttgctgga gctgcacaag     360
ctggcgacag acaaaaatga cccgcatttg tgtgatttcc tggaaactca ttatcttaat     420
gaacaagtga aggctattaa agaattgggc gatcatgtaa cgaacctgag aaggatgggg     480
gcacctgaat cagggatggc cgaatatctg ttcgataagc atacattggg tgagtgtgac     540
gaatcttga                                                            549

<210> SEQ ID NO 4
<211> LENGTH: 609
<212> TYPE: DNA
<213> ORGANISM: Artificial Sequence
<220> FEATURE:
<223> OTHER INFORMATION: Recombinant ferritin sequence

<400> SEQUENCE: 4
atggactata aggaccatga tggcgattat aaagaccatg acattgatta taaggacgac      60
gacgataagg gcggcggcag cggggggggc tccggcggtg gctctatgtt gagtaaagac     120
atcataaaac tcctgaatga gcaggtaaac aaagagatgc agtcaagcaa cctctacatg     180
tcaatgtcct cttggtgtta cacacattct ctggatgggg cgggcttgtt cctttttcgac     240 cacgcagcgg aagagtatga gcacgcaaag aaactgatta tttttctcaa cgagaataac     300
gtgccggttc agcttacctc aatcagcgcc cccgagcaca aattcgaggg cttgactcaa     360
atcttccaaa aagcgtatga gcacgagcaa cacataagtg aatccattaa caacatagtg     420
gaccacgcta ttaagtccaa agatcacgca acctttaatt tcctgcagtg gtatgttgcc     480
gaacaacatg aggaagaggt tcttttttaaa gatatactgg ataagataga actcatcggg     540
aacgaaaatc atgggttgta cctcgctgat cagtacgtaa aaggaatagc taaatcaaga     600
aaaagttga                                                            609

<210> SEQ ID NO 5
<211> LENGTH: 633
<212> TYPE: DNA
<213> ORGANISM: Artificial Sequence
<220> FEATURE:
<223> OTHER INFORMATION: Recombinant ferritin sequence

<400> SEQUENCE: 5
atggattaca aggaccatga cggggattat aaggaccatg atattgacta taaagacgac      60
gatgataaag gaggcggcag tggtggtggt agtggcggtg gatccatgtc ttcacaaata     120
cgacaaaact actccaccga tgtagaggcg gcggtcaata gcctggtaa tttgtatctg      180 caagcatcat atacgtacct gtccctgggt ttttacttcg ataggacga tgttgccctg      240
```

-continued

```
gaaggtgtta gccatttttt ccgcgagttg gcagaagaaa aaagggaggg ttacgagagg      300
cttctgaaaa tgcagaatca gcggggtggt agagctttgt ttcaagatat aaaaaagcct      360
gccgaggacg aatggggcaa gactcctgat gccatgaagg cggccatggc cttggaaaaa      420
aagttgaacc aggcactcct cgatctgcat gctctcggca gcgcccggac ggaccccac       480 ttgtgtgact ttttggaaac acattttctg gacgaggaag tgaagctcat taaaaaaatg      540
ggggaccact tgactaatct gcaccgcctt gggggtccag aagccggatt gggcgaatat      600
ctttttgaga gactcaccttt gaagcatgat tga                                   633
```

```
<210> SEQ ID NO 6
<211> LENGTH: 1029
<212> TYPE: DNA
<213> ORGANISM: Artificial Sequence
<220> FEATURE:
<223> OTHER INFORMATION: Recombinant ferritin sequence

<400> SEQUENCE: 6
```

```
atggactaca aggaccacga tggcgattat aaagatcacg acatagatta caaagatgat      60
gatgataagc ctaagaagaa gcgaaaagtt ggcatggcgg atgttcagct cgtagagtct      120
ggcggcgcac tggtgcaacc cggtggctcc ctgcgcttga gctgtgctgc ttcaggattt      180
cccgtgaaca gatattccat gcgctggtat cggcaggctc ctggaaaaga gcgagagtgg      240
gtcgcaggga tgtcctccgc cggtgatagg agctcatacg aagacagcgt taagggacgc      300
tttacaatct ctcgagatga cgcccgcaat accgtctacc tgcagatgaa cagtcttaag      360
cctgaggata ccgcagttta ttattgtaac gtgaatgtcg gttttgagta ctgggggcag      420
ggcacgcagg tgacagtttc ttccggcggc ggtagtggag cgggatcagg gggcggtagc      480
atgacaaccg cttttcccag tcaggttcgg caaaactacc atcaggacag cgaagcagcg      540
atcaatcgac aaattaacct cgagctccat gctagctacg tttacttgag tatgtccttc      600
tattttgatc gcgacgatgt tgcgttgaaa aatttcgcta agtatttctt gcaccagtca      660
catgaggaac gcgagcatgc ggaaaagttg atgaagctgc aaaaccagcg aggcgggcgc      720
attttccttc aagacatcaa aaagccagat caggatgatt gggagaacgg ccttaaggca      780
atggagtgtg cgctccacct tgaaaagaat gtcaacgaat ccctgctcga actccataag      840
ctggcgaccg acaaaaatga tcctcacctt tgcgattttc tggagacaca ttatctgaat      900
gagcaagtga aagcaataaa ggagttgggt gatcatgtca caaaccttag acggatgggg      960
gcaccagaat ccggaatggc agaatacttg tttgataagc atacgctggg tgagtgtgat     1020
gaatcttag                                                             1029
```

```
<210> SEQ ID NO 7
<211> LENGTH: 1797
<212> TYPE: DNA
<213> ORGANISM: Artificial Sequence
<220> FEATURE:
<223> OTHER INFORMATION: Recombinant ferritin sequence

<400> SEQUENCE: 7
```

```
atggattaca aagatcacga cggagattat aaggatcacg atatcgatta taaagacgat      60
gatgacaaac ccaaaaaaaa gcgcaaagtt ggtatggcgg atgtgcagtt ggttgagtct      120
ggcggggcac tcgtgcagcc ggggggtagt ctgagattga gttgtgccgc ctccggattt      180
ccagtcaaca gatattccat gcgctggtat cgacaggcgc cagggaaaga gagagaatgg      240
```

-continued

```
gttgcgggta tgtcatcagc gggtgatcga tcctcttacg aggattcagt gaaagggcgg     300
tttacaataa gccgagatga cgccagaaat acggtatacc tccagatgaa ctccctcaag     360
ccggaagata cggcagttta ctattgtaac gttaatgttg gatttgagta ttggggccaa     420
ggaacgcaag tgaccgtcag cagtggtggt ggaagtggcg gagggtcagg aggcggatct     480
atggttagca agggcgagga ggataatatg gccattatca agaattcat gcgctttaag     540 gtccacatgg agggtagtgt caacggtcat gaatttgaga tagagggtga aggggaaggt     600
aggccttacg agggtactca aactgcgaaa ttgaaagtca caagggggg tcccctccct     660 tttgcgtggg atatactctc cccacaattt atgtacggtt caaaagccta tgttaagcac     720
cctgcggaca tccccgacta cctgaaactc agttttcctg aaggcttcaa gtgggagcgg     780
gtcatgaatt ttgaggacgg tggggtcgta acggtcactc aggactcatc tcttcaagat     840
ggtgagttta tctataaagt aaagttgcgc ggtactaact ttccgtccga cggaccagta     900
atgcaaaaaa aaacaatggg ttgggaggct tcatccgaac ggatgtatcc cgaagacggg     960
gctctcaagg gtgagattaa acaaaggctt aaactgaagg atggaggcca ttacgatgct    1020
gaagttaaaa ccacgtataa agcgaagaaa cccgttcagc tgcctggtgc atataatgtg    1080
aatatcaaat tggatataac ctcacacaat gaggactata ctatcgtaga acaatatgaa    1140
cgggcggaag acgacactc aaccggggga atggatgaac tttataaagg gggaggaagc    1200
gggggagggt ctgggggtgg ttcaggcggg ggatcaggtg gcgggagtat gactactgca    1260
ttcccgagcc aagtgcggca gaattaccac caggactctg aagcggccat caaccgacaa    1320
atcaacctgg aactgcatgc gtcttacgtt tatctgtcaa tgagctttta ctttgataga    1380
gacgatgtcg cattgaagaa cttcgccaaa tattttcttc atcagagcca tgaggaaagg    1440
gaacatgcag aaaaacttat gaaattgcag aaccagcgcg gtggaaggat tttcctccaa    1500
gacataaaga aaccggatca ggacgactgg gagaatggcc tgaaggcaat ggaatgtgca    1560
cttcacctcg aaaagaacgt gaacgagagc ctcctggaac tgcataaatt ggccactgac    1620
aaaaacgatc cacacctgtg cgatttcctt gagactcatt atcttaacga gcaagtgaaa    1680
gcaattaaag agttgggtga tcatgtcact aacctgagac gcatggggc accagaaagc    1740 ggcatggcag agtatttgtt tgacaagcat acacttggtg agtgtgacga gtcttga      1797
```

```
<210> SEQ ID NO 8
<211> LENGTH: 1989
<212> TYPE: DNA
<213> ORGANISM: Artificial Sequence
<220> FEATURE:
<223> OTHER INFORMATION: Recombinant ferritin sequence

<400> SEQUENCE: 8
atggattaca aagatcacga cggagattat aaggatcacg atatcgatta taaagacgat      60
gatgacaaac ccaaaaaaaa gcgcaaagtt ggtatggcgg atgtgcagtt ggttgagtct     120
ggcggggcac tcgtgcagcc gggggggtagt ctgagattga gttgtgccgc ctccggattt     180
ccagtcaaca gatattcaat gcgctggtat cgacaggcgc cagggaaaga gagagaatgg     240
gttgcgggta tgtcatcagc gggtgatcga tcctcttacg aggattcagt gaaagggcgg     300
tttacaataa gccgagatga cgccagaaat acggtatacc tccagatgaa ctccctcaag     360
ccggaagata cggcagttta ctattgtaac gttaatgttg gatttgagta ttggggccaa     420
ggaacgcaag tgaccgtcag cagtggtggt ggaagtggcg gagggtcagg aggcggatct     480
gaaatcggta ctggctttcc attcgacccc cattatgtgg aagtcctggg cgagcgcatg     540
```

-continued

```
cactacgtcg atgttggtcc gcgcgatggc acccctgtgc tgttcctgca cggtaacccg      600
acctcctcct acgtgtggcg caacatcatc ccgcatgttg caccgaccca tcgctgcatt      660
gctccagacc tgatcggtat gggcaaatcc gacaaaccag acctgggtta tttcttcgac      720
gaccacgtcc gcttcatgga tgccttcatc gaagccctgg gtctggaaga ggtcgtcctg      780
gtcattcacg actggggctc cgctctgggt ttccactggg ccaagcgcaa tccagagcgc      840
gtcaaaggta ttgcatttat ggagttcatc cgccctatcc cgacctggga cgaatggcca      900
gaatttgccc gcgagacctt ccaggccttc cgcaccaccg acgtcggccg caagctgatc      960
atcgatcaga acgtttttat cgagggtacg ctgccgatgg gtgtcgtccg cccgctgact     1020
gaagtcgaga tggaccatta ccgcgagccg ttcctgaatc ctgttgaccg cgagccactg     1080
tggcgcttcc caaacgagct gccaatcgcc ggtgagccag cgaacatcgt cgcgctggtc     1140
gaagaataca tggactggct gcaccagtcc cctgtcccga agctgctgtt ctggggcacc     1200
ccaggcgttc tgatcccacc ggccgaagcc gctcgcctgg ccaaaagcct gcctaactgc     1260
aaggctgtgg acatcggccc gggtctgaat ctgctgcaag aagacaaccc ggacctgatc     1320
ggcagcgaga tcgcgcgctg gctgtccacg ctcgagattt ccggcggggg aggaggcagc     1380
ggggggaggg gttctggggg tggtggatca ggcggggagg gctcaggtgg cggggggaagt     1440 atgactactg cattcccgag ccaagtgcgg cagaattacc accaggactc tgaagcggcc     1500
atcaaccgac aaatcaacct ggaactgcat gcgtcttacg tttatctgtc aatgagcttt     1560
tactttgata gagacgatgt cgcattgaag aacttcgcca atatttttct tcatcagagc     1620
catgaggaaa gggaacatgc agaaaaactt atgaaattgc agaaccagcg cggtggaagg     1680
attttcctcc aagacataaa gaaaccggat caggacgact gggagaatgg cctgaaggca     1740
atggaatgtg cacttcacct cgaaaagaac gtgaacgaga gcctcctgga actgcataaa     1800
ttggccactg acaaaaacga tccacacctg tgcgatttcc ttgagactca ttatcttaac     1860
gagcaagtga aagcaattaa agagttgggt gatcatgtca ctaacctgag acgcatgggg     1920
gcaccagaaa gcggcatggc agagtatttg tttgacaagc atacacttgg tgagtgtgac     1980
gagtcttga                                                             1989
```

```
<210> SEQ ID NO 9
<211> LENGTH: 351
<212> TYPE: DNA
<213> ORGANISM: Artificial Sequence
<220> FEATURE:
<223> OTHER INFORMATION: MS2 stem loop binding protein

<400> SEQUENCE: 9
```

```
atggcttcta actttactca gttcgttctc gtcgacaatg gcggaactgg cgacgtgact       60
gtcgccccaa gcaacttcgc taacgggatc gctgaatgga tcagctctaa ctcgcgttca      120
caggcttaca aagtaacctg tagcgttcgt cagagctctg cgcagaatcg caaatacacc      180
atcaaagtcg aggtgcctaa aggcgcctgg cgttcgtact aaatatggaa ctaaccatt       240 ccaattttcg ccacgaattc cgactgcgag cttattgtta aggcaatgca aggtctccta      300
aaagatggaa acccgattcc ctcagcaatc gcagcaaact ccggcatcta c              351
```

```
<210> SEQ ID NO 10
<211> LENGTH: 69
<212> TYPE: DNA
<213> ORGANISM: Artificial Sequence
<220> FEATURE:
```

```
<223> OTHER INFORMATION: lambda N22 RNA binding protein

<400> SEQUENCE: 10
atgggtaatg ctcggacccg gcgaagagag aggcgggctg agaagcaggc acagtggaag     60
gctgcaaac                                                             69

<210> SEQ ID NO 11
<211> LENGTH: 369
<212> TYPE: DNA
<213> ORGANISM: Artificial Sequence
<220> FEATURE:
<223> OTHER INFORMATION: PP7 RNA stem loop coat protein

<400> SEQUENCE: 11
atgggttcca aaaccatcgt tctttcggtc ggcgaggcta ctcgcactct gactgagatc     60
cagtccaccg cagaccgtca gatcttcgaa gagaaggtcg ggcctctggt gggtcggctg    120
cgcctcacgg cttcgctccg tcaaaacgga gccaagaccg cgtatcgcgt caacctaaaa    180
ctggatcagg cggacgtcgt tgattccgga cttccgaaag tgcgctacac tcaggtatgg    240
tcgcacgacg tgacaatcgt tgcgaatagc accgaggcct cgcgcaaatc gttgtacgat    300
ttgaccaagt ccctcgtcgc gacctcgcag gtcgaagatc ttgtcgtcaa ccttgtgccg    360
ctgggccgt                                                            369

<210> SEQ ID NO 12
<211> LENGTH: 741
<212> TYPE: DNA
<213> ORGANISM: Artificial Sequence
<220> FEATURE:
<223> OTHER INFORMATION: anti-suntag scFv

<400> SEQUENCE: 12
atgggtccag acatagtgat gacgcagagt ccgtctagtc tctcagcttc tgtcggcgac     60
cgggttacta ttacatgccg ctccagcact ggagcagtga caacgtctaa ctacgcttca    120
tgggttcaag aaaagccagg aaaactcttc aaaggcctga ttggtgggac caacaatcga    180
gcacccggtg ttcctagccg gttttctggc agcctcatag gagataaagc gacgctgact    240
atatcaagtt tgcaacctga ggatttcgcc acatacttct gcgccctttg gtattccaac    300
cactgggtct tcggacaagg cactaaggtg gaactgaaga gaggcggtgg cggctccggc    360
ggtggtggct ccggggcggg cgggtccagc ggtggtggga gcgaagtaaa gttgctcgaa    420
tccgggggag gactcgtgca acccggagga tcattgaaac tgtcctgcgc ggtgtcagga    480
ttctcactca cagactacgg agtaaattgg gttcgccaag ctccgggccg gggtctggaa    540
tggatcggcg tgatctgggg cgatggtatc accgactata actctgcact caaagatagg    600
tttatcattt ccaaagacaa tgggaagaac acggtatacc tgcagatgtc taaggtgaga    660
agcgatgaca cagcgttgta ttattgtgtg actgggcttt ttgattattg gggtcagggc    720
acactcgtga ctgtctccag c                                              741

<210> SEQ ID NO 13
<211> LENGTH: 387
<212> TYPE: DNA
<213> ORGANISM: Artificial Sequence
<220> FEATURE:
<223> OTHER INFORMATION: anti-mCherry VHH

<400> SEQUENCE: 13
atggctcaag ttcagcttgt cgagagcggc ggcagtttgg ttcaacctgg aggtagtctt     60
```

-continued

```
cggctctctt gcgcggctag tgggcggttt gcggagtctt ctagtatggg gtggtttcgg      120
caggccccag gcaaagaacg cgagtttgtt gcagcgatta gttggagtgg tggggcgacg      180
aattatgcag atagcgcaaa gggccgattt acgcttagcc gggacaacac taagaacacc      240
gtttacttgc aaatgaactc attgaaaccg gacgatacg cggtttatta ctgcgcggcc       300
aacttgggga actatatatc aagcaaccag aggctctacg gttactgggg ccaagggacg      360
caagttacag tatctagccc tttcacg                                          387
```

```
<210> SEQ ID NO 14
<211> LENGTH: 1062
<212> TYPE: DNA
<213> ORGANISM: Artificial Sequence
<220> FEATURE:
<223> OTHER INFORMATION: PUFa

<400> SEQUENCE: 14
tctagaggcc gcagccgcct tttggaagat tttcgaaaca accggtaccc caatttacaa       60
ctgcgggaga ttgctggaca tataatggaa ttttcccaag accagcatgg gtccagattc      120
attcagctga aactggagcg tgccacacca gctgagcgcc agcttgtctt caatgaaatc      180
ctccaggctg cctaccaact catggtggat gtgtttggta attacgtcat tcagaagttc      240
tttgaatttg gcagtcttga acagaagctg gctttggcag aacggattcg aggccacgtc      300
ctgtcattgg cactacagat gtatggcagc cgtgttatcg agaaagctct tgagtttatt      360
ccttcagacc agcagaatga gatggttcgg gaactagatg gccatgtctt gaagtgtgtg      420
aaagatcaga atggcaatca cgtggttcag aaatgcattg aatgtgtaca gccccagtct      480
ttgcaattta tcatcgatgc gtttaaggga caggtatttg ccttatccac acatccttat      540
ggctgccgag tgattcagag aatcctggag cactgtctcc ctgaccagac actccctatt      600
ttagaggagc ttcaccagca cacagagcag ctggtacagg atcaatatgg aaattatgta      660
atccaacatg tactggagca cggtcgtcct gaggataaaa gcaaaattgt agcagaaatc      720
cgaggcaatg tacttgtatt gagtcagcac aaatttgcaa gcaatgttgt ggagaagtgt      780
gttactcacg cctcacgtac ggagcgcgct gtgctcatcg acgaggtgtg caccatgaac      840
gacggtcccc acagtgcctt atacaccatg atgaaggacc agtatgccaa ctacgtggtc      900
cagaagatga ttgacgtggc ggagccaggc cagcggaaga tcgtcatgca taagatccgg      960
ccccacatcg caactcttcg taagtacacc tatggcaagc acattctggc caagctggag     1020
aagtactaca tgaagaacgg tgttgactta gggggggccgg cc                       1062
```

```
<210> SEQ ID NO 15
<211> LENGTH: 1062
<212> TYPE: DNA
<213> ORGANISM: Artificial Sequence
<220> FEATURE:
<223> OTHER INFORMATION: PUFb

<400> SEQUENCE: 15
tctagaggcc gcagccgcct tttggaagat tttcgaaaca accggtaccc caatttacaa       60
ctgcgggaga ttgctggaca tataatggaa ttttcccaag accagcatgg gtccagattc      120
attcagctga aactggagcg tgccacacca gctgagcgcc agcttgtctt caatgaaatc      180
ctccaggctg cctaccaact catggtggat gtgtttggta attacgtcat tcagaagttc      240
tttgaatttg gcagtcttga acagaagctg gctttggcag aacggattcg aggccacgtc      300
```

```
ctgtcattgg cactacagat gtatggctgc cgtgttatcc agaaagctct tgagtttatt      360
ccttcagacc agcagaatga gatggttcgg gaactagatg gccatgtctt gaagtgtgtg      420
aaagatcaga atggcaatca cgtggttcag aaatgcattg aatgtgtaca gccccagtct      480
ttgcaattta tcatcgatgc gtttaaggga caggtatttg ccttatccac acatccttat      540
ggctgccgag tgattcagag aatcctggag cactgtctcc ctgaccagac actccctatt      600
ttagaggagc ttcaccagca cacagagcag ctggtacagg atcaatatgg aagttatgta      660
atcgaacatg tactggagca cggtcgtcct gaggataaaa gcaaaattgt agcagaaatc      720
cgaggcaatg tacttgtatt gagtcagcac aaatttgcaa acaatgttgt gcagaagtgt      780
gttactcacg cctcacgtac ggagcgcgct gtgctcatcg atgaggtgtg caccatgaac      840
gacggtcccc acagtgcctt atacaccatg atgaaggacc agtatgccaa ctacgtggtc      900
cagaagatga ttgacgtggc ggagccaggc cagcggaaga tcgtcatgca taagatccgg      960
ccccacatcg caactcttcg taagtacacc tatggcaagc acattctggc caagctggag     1020
aagtactaca tgaagaacgg tgttgactta gggggggccgg cc                       1062

<210> SEQ ID NO 16
<211> LENGTH: 270
<212> TYPE: DNA
<213> ORGANISM: Artificial Sequence
<220> FEATURE:
<223> OTHER INFORMATION: FRB

<400> SEQUENCE: 16
gagatgtggc atgaaggcct agaagaggcc tctcgcttgt actttgggga gaggaacgtc       60
aaaggcatgt ttgaggtgct ggagcccctg catgctatga tggaacgcgg tccccagacc      120
ctgaaggaaa cgtcctttaa tcaggcatat ggtcgagatt taatggaggc acaagaatgg      180
tgccgaaagt acatgaaatc agggaacgtc aaggacctcc tccaagcctg ggacctctac      240
tatcacgtgt tcagacgaat ctcaaagcag                                      270

<210> SEQ ID NO 17
<211> LENGTH: 318
<212> TYPE: DNA
<213> ORGANISM: Artificial Sequence
<220> FEATURE:
<223> OTHER INFORMATION: FKBP

<400> SEQUENCE: 17
ggagtgcagg tggaaaccat ctccccagga gacgggcgca ccttccccaa gcgcggccag       60
acctgcgtgg tgcactacac cgggatgctt gaagatggaa agaaatttga ttcctcccgg      120
gacagaaaca gcccctttaa gtttatgcta ggcaagcagg aggtgatccg aggctgggaa      180
gaaggggttg cccagatgag tgtgggtcag agagccaaac tgactatatc tccagattat      240
gcctatggtg ccactgggca cccaggcatc atcccaccac atgccactct cgtcttcgat      300
gtggagcttc taaaactg                                                   318

<210> SEQ ID NO 18
<211> LENGTH: 4101
<212> TYPE: DNA
<213> ORGANISM: Artificial Sequence
<220> FEATURE:
<223> OTHER INFORMATION: dSpCas9

<400> SEQUENCE: 18
gacaagaagt actccattgg gctcgctatc ggtaccaaca gcgtcggctg ggccgtcatt       60
```

-continued

```
acggacgagt acaaggtgcc gagcaaaaaa ttcaaagttc tgggcaatac cgatcgccac      120
agcataaaga agaacctcat tggagccctc ctgttcgact ccggggagac ggccgaagcc      180
acgcggctca aaagaacagc acggcgcaga tatacccgca gaaagaatcg gatctgctac      240
ctgcaggaga tctttagtaa tgagatggct aaggtggatg actctttctt ccataggctg      300
gaggagtcct ttttggtgga ggaggataaa aagcacgagc gccacccaat ctttggcaat      360
atcgtggacg aggtggcgta ccatgaaaag tacccaacca tatatcatct gaggaagaag      420
ctggtagaca gtactgataa ggctgacttg cggttgatct atctcgcgct ggcgcacatg      480
atcaaatttc ggggacactt cctcatcgag ggggacctga acccagacaa cagcgatgtc      540
gacaaactct ttatccaact ggttcagact tacaatcagc ttttcgagga gaacccgatc      600
aacgcatccg gcgttgacgc caaagcaatc ctgagcgcta ggctgtccaa atcccggcgg      660
ctcgaaaacc tcatcgcaca gctccctggg gagaagaaga acggcctgtt tggtaatctt      720
atcgccctgt cactcgggct gacccccaac tttaaatcta acttcgacct ggccgaagat      780
gccaagctgc aactgagcaa agacacctac gatgatgatc tcgacaatct gctggcccag      840
atcggcgacc agtacgcaga cctttttttg gcggcaaaga acctgtcaga cgccattctg      900
ctgagtgata ttctgcgagt gaacacggag atcaccaaag ctccgctgag cgctagtatg      960
atcaagcgct atgatgagca ccaccaagac ttgactttgc tgaaggccct tgtcagacag     1020
caactgcctg agaagtacaa ggaaattttc ttcgatcagt ctaaaaatgg ctacgccgga     1080
tacattgacg gcggagcaag ccaggaggaa ttttacaaat ttattaagcc catcttggaa     1140
aaaatggacg gcaccgagga gctgctggta aagctgaaca gagaagatct gttgcgcaaa     1200
cagcgcactt tcgacaatgg aagcatcccc caccagattc acctgggcga actgcacgct     1260
atcctcaggc ggcaagagga tttctacccc tttttgaaag ataacaggga aaagattgag     1320
aaaatcctca catttcggat accctactat gtaggccccc tcgctcgggg aaattccaga     1380
ttcgcgtgga tgactcgcaa atcagaagag accatcactc cctggaactt cgaggaagtc     1440
gtggataagg gggcctctgc ccagtccttc atcgaaagga tgactaactt tgataaaaat     1500
ctgcctaacg aaaaggtgct tcctaaacac tctctgctgt acgagtactt cacagtttat     1560
aacgagctca ccaaggtcaa atacgtcaca gaagggatga gaaagccagc attcctgtct     1620
ggagagcaga gaaagctat cgtggacctc ctcttcaaga cgaaccggaa agttaccgtg     1680
aaacagctca agaagacta tttcaaaaag attgaatgtt tcgactctgt tgaaatcagc     1740
ggagtggagg atcgcttcaa cgcatccctg ggaacgtatc acgatctcct gaaaatcatt     1800
aaagacaagg acttcctgga caatgaggag aacgaggaca ttcttgagga cattgtcctc     1860
acccttacgt tgtttgaaga tagggagatg attgaagaac gcttgaaaac ttacgctcat     1920
ctcttcgacg acaaagtcat gaaacagctc aagagacgcc gatatacagg atgggggcgg     1980
ctgtcaagaa aactgatcaa tggcatccga gacaagcaga gtggaaagac aatcctggat     2040
tttcttaagt ccgatggatt tgccaaccgg aacttcatgc agttgatcca tgatgactct     2100 ctcacctttta aggaggacat ccagaaagca caagtttctg gccaggggga cagtcttcac     2160
gagcacatcg ctaatcttgc aggtagccca gctatcaaaa agggaatact gcagaccgtt     2220
aaggtcgtgg atgaactcgt caaagtaatg ggaaggcata gcccgagaa tatcgttatc     2280 gagatggccc gagagaacca aactacccag aagggcacaga agaacagtag ggaaaggatg     2340
aagaggattg aagagggtat aaaagaactg gggtcccaaa tccttaagga acacccagtt     2400
```

```
gaaaacaccc agcttcagaa tgagaagctc tacctgtact acctgcagaa cggcagggac     2460
atgtacgtgg atcaggaact ggacatcaac cggttgtccg actacgacgt ggatgctatc     2520
gtgccccaaa gctttctcaa agatgattct attgataata aagtgttgac aagatccgat     2580
aaaaatagag ggaagagtga taacgtcccc tcagaagaag ttgtcaagaa aatgaaaaat     2640
tattggcggc agctgctgaa cgccaaactg atcacacaac ggaagttcga taatctgact     2700
aaggctgaac gaggtggcct gtctgagttg ataaagccg gcttcatcaa aaggcagctt      2760
gttgagacac gccagatcac caagcacgtg gcccaaattc tcgattcacg catgaacacc     2820
aagtacgatg aaaatgacaa actgattcga gaggtgaaag ttattactct gaagtctaag     2880
ctggtctcag atttcagaaa ggactttcag ttttataagg tgagagagat caacaattac     2940
caccatgcgc atgatgccta cctgaatgca gtggtaggca ctgcacttat caaaaaatat     3000
cccaagctgg aatctgaatt tgtttacgga gactataaag tgtacgatgt taggaaaatg     3060
atcgcaaagt ctgagcagga aataggcaag gccaccgcta agtacttctt ttacagcaat     3120
attatgaatt ttttcaagac cgagattaca ctggccaatg gagagattcg gaagcgacca     3180
cttatcgaaa caaacggaga aacaggagaa atcgtgtggg acaagggtag ggatttcgcg     3240
acagtccgca aggtcctgtc catgccgcag gtgaacatcg ttaaaaagac cgaagtacag     3300
accggaggct ctccaaggga aagtatcctc ccgaaaagga acagcgacaa gctgatcgca     3360
cgcaaaaaag attgggaccc caagaaatac ggcggattcg attctcctac agtcgcttac     3420
agtgtactgg ttgtggccaa agtggagaaa gggaagtcta aaaaactcaa aagcgtcaag     3480
gaactgctgg gcatcacaat catggagcga tccagcttcg agaaaaaccc catcgacttt     3540
ctcgaagcga aggatataa agaggtcaaa aaagacctca tcattaagct gcccaagtac      3600
tctctctttg agcttgaaaa cggccggaaa cgaatgctcg ctagtgcggg cgagctgcag     3660
aaaggtaacg agctggcact gccctctaaa tacgttaatt tcttgtatct ggccagccac     3720
tatgaaaagc tcaaagggtc tcccgaagat aatgagcaga agcagctgtt cgtgaacaa      3780 cacaaacact accttgatga gatcatcgag caaataagcg agttctccaa aagagtgatc     3840
ctcgccgacg ctaacctcga taaggtgctt tctgcttaca ataagcacag ggataagccc     3900
atcagggagc aggcagaaaa cattatccac ttgtttactc tgaccaactt gggcgcgcct     3960
gcagccttca agtacttcga caccaccata gacagaaagc ggtacacctc tacaaaggag     4020
gtcctggacg ccacactgat tcatcagtca attacggggc tctatgaaac aagaatcgac     4080
ctctctcagc tcggtggaga c                                             4101
```

<210> SEQ ID NO 19
<211> LENGTH: 558
<212> TYPE: PRT
<213> ORGANISM: Artificial Sequence
<220> FEATURE:
<223> OTHER INFORMATION: Recombinant ferritin sequence

<400> SEQUENCE: 19

```
Met Pro Lys Lys Lys Arg Lys Val Gly Ser Gly Met Ala Asp Val Gln
1               5                   10                  15

Leu Val Glu Ser Gly Gly Ala Leu Val Gln Pro Gly Gly Ser Leu Arg
            20                  25                  30

Leu Ser Cys Ala Ala Ser Gly Phe Pro Val Asn Arg Tyr Ser Met Arg
        35                  40                  45

Trp Tyr Arg Gln Ala Pro Gly Lys Glu Arg Glu Trp Val Ala Gly Met
    50                  55                  60
```

-continued

```
Ser Ser Ala Gly Asp Arg Ser Ser Tyr Glu Asp Ser Val Lys Gly Arg
65              70              75              80

Phe Thr Ile Ser Arg Asp Asp Ala Arg Asn Thr Val Tyr Leu Gln Met
                85              90              95

Asn Ser Leu Lys Pro Glu Asp Thr Ala Val Tyr Tyr Cys Asn Val Asn
            100             105             110

Val Gly Phe Glu Tyr Trp Gly Gln Gly Thr Gln Val Thr Val Ser Ser
            115             120             125

Gly Ser Gly Trp Ser His Pro Gln Phe Glu Lys Gly Ser Gly His His
            130             135             140

His His His His Gly Ser Gly Pro Lys Lys Lys Arg Lys Val Met Val
145             150             155             160

Ser Lys Gly Glu Glu Asp Asn Met Ala Ile Ile Lys Glu Phe Met Arg
                165             170             175

Phe Lys Val His Met Glu Gly Ser Val Asn Gly His Glu Phe Glu Ile
            180             185             190

Glu Gly Glu Gly Glu Gly Arg Pro Tyr Glu Gly Thr Gln Thr Ala Lys
            195             200             205

Leu Lys Val Thr Lys Gly Gly Pro Leu Pro Phe Ala Trp Asp Ile Leu
            210             215             220

Ser Pro Gln Phe Met Tyr Gly Ser Lys Ala Tyr Val Lys His Pro Ala
225             230             235             240

Asp Ile Pro Asp Tyr Leu Lys Leu Ser Phe Pro Glu Gly Phe Lys Trp
                245             250             255

Glu Arg Val Met Asn Phe Glu Asp Gly Gly Val Val Thr Val Thr Gln
            260             265             270

Asp Ser Ser Leu Gln Asp Gly Glu Phe Ile Tyr Lys Val Lys Leu Arg
            275             280             285

Gly Thr Asn Phe Pro Ser Asp Gly Pro Val Met Gln Lys Lys Thr Met
            290             295             300

Gly Trp Glu Ala Ser Ser Glu Arg Met Tyr Pro Glu Asp Gly Ala Leu
305             310             315             320

Lys Gly Glu Ile Lys Gln Arg Leu Lys Leu Lys Asp Gly Gly His Tyr
                325             330             335

Asp Ala Glu Val Lys Thr Thr Tyr Lys Ala Lys Lys Pro Val Gln Leu
            340             345             350

Pro Gly Ala Tyr Asn Val Asn Ile Lys Leu Asp Ile Thr Ser His Asn
            355             360             365

Glu Asp Tyr Thr Ile Val Glu Gln Tyr Glu Arg Ala Glu Gly Arg His
            370             375             380

Ser Thr Gly Gly Met Asp Glu Leu Tyr Lys Gly Ser Gly Ser Gly Ser
385             390             395             400

Met Lys Gly Asp Thr Lys Val Ile Asn Tyr Leu Asn Lys Leu Leu Gly
                405             410             415

Asn Glu Leu Val Ala Ile Asn Gln Tyr Phe Leu His Ala Arg Met Phe
            420             425             430

Lys Asn Trp Gly Leu Lys Arg Leu Asn Asp Val Glu Tyr His Glu Ser
            435             440             445

Ile Asp Glu Met Lys His Ala Asp Arg Tyr Ile Glu Arg Ile Leu Phe
            450             455             460

Leu Glu Gly Leu Pro Asn Leu Gln Asp Leu Gly Lys Leu Asn Ile Gly
465             470             475             480
```

-continued

```
Glu Asp Val Glu Glu Met Leu Arg Ser Asp Leu Ala Leu Glu Leu Asp
                485             490             495

Gly Ala Lys Asn Leu Arg Glu Ala Ile Gly Tyr Ala Asp Ser Val His
            500             505             510

Asp Tyr Val Ser Arg Asp Met Met Ile Glu Ile Leu Arg Asp Glu Glu
            515             520             525

Gly His Ile Asp Trp Leu Glu Thr Glu Leu Asp Leu Ile Gln Lys Met
        530             535             540

Gly Leu Gln Asn Tyr Leu Gln Ala Gln Ile Arg Glu Glu Gly
545             550             555
```

```
<210> SEQ ID NO 20
<211> LENGTH: 200
<212> TYPE: PRT
<213> ORGANISM: Artificial Sequence
<220> FEATURE:
<223> OTHER INFORMATION: Recombinant ferritin sequence

<400> SEQUENCE: 20

Met Asp Tyr Lys Asp His Asp Gly Asp Tyr Lys Asp His Asp Ile Asp
1               5               10              15

Tyr Lys Asp Asp Asp Asp Lys Gly Gly Gly Ser Gly Gly Gly Ser Gly
            20              25              30

Gly Gly Ser Met Leu Lys Pro Glu Met Ile Glu Lys Leu Asn Glu Gln
        35              40              45

Met Asn Leu Glu Leu Tyr Ser Ser Leu Leu Tyr Gln Gln Met Ser Ala
    50              55              60

Trp Cys Ser Tyr His Thr Phe Glu Gly Ala Ala Ala Phe Leu Arg Arg
65              70              75              80

His Ala Gln Glu Glu Met Thr His Met Gln Arg Leu Phe Asp Tyr Leu
                85              90              95

Thr Asp Thr Gly Asn Leu Pro Arg Ile Asn Thr Val Glu Ser Pro Phe
            100             105             110

Ala Glu Tyr Ser Ser Leu Asp Glu Leu Phe Gln Glu Thr Tyr Lys His
            115             120             125

Glu Gln Leu Ile Thr Gln Lys Ile Asn Glu Leu Ala His Ala Ala Met
        130             135             140

Thr Asn Gln Asp Tyr Pro Thr Phe Asn Phe Leu Gln Trp Tyr Val Ser
145             150             155             160

Glu Gln His Glu Glu Glu Lys Leu Phe Lys Ser Ile Ile Asp Lys Leu
                165             170             175

Ser Leu Ala Gly Lys Ser Gly Glu Gly Leu Tyr Phe Ile Asp Lys Glu
            180             185             190

Leu Ser Thr Leu Asp Thr Gln Asn
        195             200
```

```
<210> SEQ ID NO 21
<211> LENGTH: 182
<212> TYPE: PRT
<213> ORGANISM: Artificial Sequence
<220> FEATURE:
<223> OTHER INFORMATION: Recombinant ferritin sequence

<400> SEQUENCE: 21

Met Thr Thr Ala Phe Pro Ser Gln Val Arg Gln Asn Tyr His Gln Asp
1               5               10              15

Ser Glu Ala Ala Ile Asn Arg Gln Ile Asn Leu Glu Leu His Ala Ser
            20              25              30
```

Tyr Val Tyr Leu Ser Met Ser Phe Tyr Phe Asp Arg Asp Asp Val Ala
        35                  40                  45

Leu Lys Asn Phe Ala Lys Tyr Phe Leu His Gln Ser His Glu Glu Arg
    50                  55                  60

Glu His Ala Glu Lys Leu Met Lys Leu Gln Asn Gln Arg Gly Gly Arg
65                  70                  75                  80

Ile Phe Leu Gln Asp Ile Lys Lys Pro Asp Gln Asp Asp Trp Glu Asn
                85                  90                  95

Gly Leu Lys Ala Met Glu Cys Ala Leu His Leu Glu Lys Asn Val Asn
                100                 105                 110

Glu Ser Leu Leu Glu Leu His Lys Leu Ala Thr Asp Lys Asn Asp Pro
        115                 120                 125

His Leu Cys Asp Phe Leu Glu Thr His Tyr Leu Asn Glu Gln Val Lys
        130                 135                 140

Ala Ile Lys Glu Leu Gly Asp His Val Thr Asn Leu Arg Arg Met Gly
145                 150                 155                 160

Ala Pro Glu Ser Gly Met Ala Glu Tyr Leu Phe Asp Lys His Thr Leu
                165                 170                 175

Gly Glu Cys Asp Glu Ser
                180

<210> SEQ ID NO 22
<211> LENGTH: 202
<212> TYPE: PRT
<213> ORGANISM: Artificial Sequence
<220> FEATURE:
<223> OTHER INFORMATION: Recombinant ferritin sequence

<400> SEQUENCE: 22

Met Asp Tyr Lys Asp His Asp Gly Asp Tyr Lys Asp His Asp Ile Asp
1                   5                   10                  15

Tyr Lys Asp Asp Asp Asp Lys Gly Gly Gly Ser Gly Gly Gly Ser Gly
                20                  25                  30

Gly Gly Ser Met Leu Ser Lys Asp Ile Ile Lys Leu Leu Asn Glu Gln
        35                  40                  45

Val Asn Lys Glu Met Gln Ser Ser Asn Leu Tyr Met Ser Met Ser Ser
    50                  55                  60

Trp Cys Tyr Thr His Ser Leu Asp Gly Ala Gly Leu Phe Leu Phe Asp
65                  70                  75                  80

His Ala Ala Glu Glu Tyr Glu His Ala Lys Lys Leu Ile Ile Phe Leu
                85                  90                  95

Asn Glu Asn Asn Val Pro Val Gln Leu Thr Ser Ile Ser Ala Pro Glu
                100                 105                 110

His Lys Phe Glu Gly Leu Thr Gln Ile Phe Gln Lys Ala Tyr Glu His
        115                 120                 125

Glu Gln His Ile Ser Glu Ser Ile Asn Asn Ile Val Asp His Ala Ile
        130                 135                 140

Lys Ser Lys Asp His Ala Thr Phe Asn Phe Leu Gln Trp Tyr Val Ala
145                 150                 155                 160

Glu Gln His Glu Glu Glu Val Leu Phe Lys Asp Ile Leu Asp Lys Ile
                165                 170                 175

Glu Leu Ile Gly Asn Glu Asn His Gly Leu Tyr Leu Ala Asp Gln Tyr
                180                 185                 190

Val Lys Gly Ile Ala Lys Ser Arg Lys Ser
        195                 200

-continued

<210> SEQ ID NO 23
<211> LENGTH: 210
<212> TYPE: PRT
<213> ORGANISM: Artificial Sequence
<220> FEATURE:
<223> OTHER INFORMATION: Recombinant ferritin sequence

<400> SEQUENCE: 23

Met Asp Tyr Lys Asp His Asp Gly Asp Tyr Lys Asp His Asp Ile Asp
1               5                   10                  15

Tyr Lys Asp Asp Asp Asp Lys Gly Gly Gly Ser Gly Gly Gly Ser Gly
            20                  25                  30

Gly Gly Ser Met Ser Ser Gln Ile Arg Gln Asn Tyr Ser Thr Asp Val
            35                  40                  45

Glu Ala Ala Val Asn Ser Leu Val Asn Leu Tyr Leu Gln Ala Ser Tyr
        50                  55                  60

Thr Tyr Leu Ser Leu Gly Phe Tyr Phe Asp Arg Asp Asp Val Ala Leu
65                  70                  75                  80

Glu Gly Val Ser His Phe Phe Arg Glu Leu Ala Glu Glu Lys Arg Glu
                85                  90                  95

Gly Tyr Glu Arg Leu Leu Lys Met Gln Asn Gln Arg Gly Gly Arg Ala
            100                 105                 110

Leu Phe Gln Asp Ile Lys Lys Pro Ala Glu Asp Glu Trp Gly Lys Thr
            115                 120                 125

Pro Asp Ala Met Lys Ala Ala Met Ala Leu Glu Lys Lys Leu Asn Gln
        130                 135                 140

Ala Leu Leu Asp Leu His Ala Leu Gly Ser Ala Arg Thr Asp Pro His
145                 150                 155                 160

Leu Cys Asp Phe Leu Glu Thr His Phe Leu Asp Glu Glu Val Lys Leu
                165                 170                 175

Ile Lys Lys Met Gly Asp His Leu Thr Asn Leu His Arg Leu Gly Gly
            180                 185                 190

Pro Glu Ala Gly Leu Gly Glu Tyr Leu Phe Glu Arg Leu Thr Leu Lys
            195                 200                 205

His Asp
    210

<210> SEQ ID NO 24
<211> LENGTH: 342
<212> TYPE: PRT
<213> ORGANISM: Artificial Sequence
<220> FEATURE:
<223> OTHER INFORMATION: Recombinant ferritin sequence

<400> SEQUENCE: 24

Met Asp Tyr Lys Asp His Asp Gly Asp Tyr Lys Asp His Asp Ile Asp
1               5                   10                  15

Tyr Lys Asp Asp Asp Asp Lys Pro Lys Lys Arg Lys Val Gly Met
            20                  25                  30

Ala Asp Val Gln Leu Val Glu Ser Gly Gly Ala Leu Val Gln Pro Gly
            35                  40                  45

Gly Ser Leu Arg Leu Ser Cys Ala Ala Ser Gly Phe Pro Val Asn Arg
        50                  55                  60

Tyr Ser Met Arg Trp Tyr Arg Gln Ala Pro Gly Lys Glu Arg Glu Trp
65                  70                  75                  80

Val Ala Gly Met Ser Ser Ala Gly Asp Arg Ser Ser Tyr Glu Asp Ser

-continued

```
                   85                   90                   95
Val Lys Gly Arg Phe Thr Ile Ser Arg Asp Asp Ala Arg Asn Thr Val
            100                 105                 110

Tyr Leu Gln Met Asn Ser Leu Lys Pro Glu Asp Thr Ala Val Tyr Tyr
        115                 120                 125

Cys Asn Val Asn Val Gly Phe Glu Tyr Trp Gly Gln Gly Thr Gln Val
        130                 135                 140

Thr Val Ser Ser Gly Gly Gly Ser Gly Gly Ser Gly Gly Gly Ser
145                 150                 155                 160

Met Thr Thr Ala Phe Pro Ser Gln Val Arg Gln Asn Tyr His Gln Asp
                165                 170                 175

Ser Glu Ala Ala Ile Asn Arg Gln Ile Asn Leu Glu Leu His Ala Ser
            180                 185                 190

Tyr Val Tyr Leu Ser Met Ser Phe Tyr Phe Asp Arg Asp Asp Val Ala
        195                 200                 205

Leu Lys Asn Phe Ala Lys Tyr Phe Leu His Gln Ser His Glu Glu Arg
        210                 215                 220

Glu His Ala Glu Lys Leu Met Lys Leu Gln Asn Gln Arg Gly Gly Arg
225                 230                 235                 240

Ile Phe Leu Gln Asp Ile Lys Lys Pro Asp Gln Asp Asp Trp Glu Asn
                245                 250                 255

Gly Leu Lys Ala Met Glu Cys Ala Leu His Leu Glu Lys Asn Val Asn
            260                 265                 270

Glu Ser Leu Leu Glu Leu His Lys Leu Ala Thr Asp Lys Asn Asp Pro
        275                 280                 285

His Leu Cys Asp Phe Leu Glu Thr His Tyr Leu Asn Glu Gln Val Lys
    290                 295                 300

Ala Ile Lys Glu Leu Gly Asp His Val Thr Asn Leu Arg Arg Met Gly
305                 310                 315                 320

Ala Pro Glu Ser Gly Met Ala Glu Tyr Leu Phe Asp Lys His Thr Leu
                325                 330                 335

Gly Glu Cys Asp Glu Ser
                340
```

```
<210> SEQ ID NO 25
<211> LENGTH: 598
<212> TYPE: PRT
<213> ORGANISM: Artificial Sequence
<220> FEATURE:
<223> OTHER INFORMATION: Recombinant ferritin sequence

<400> SEQUENCE: 25
```

```
Met Asp Tyr Lys Asp His Asp Gly Asp Tyr Lys Asp His Asp Ile Asp
1               5                   10                  15

Tyr Lys Asp Asp Asp Asp Lys Pro Lys Lys Lys Arg Lys Val Gly Met
            20                  25                  30

Ala Asp Val Gln Leu Val Glu Ser Gly Gly Ala Leu Val Gln Pro Gly
        35                  40                  45

Gly Ser Leu Arg Leu Ser Cys Ala Ala Ser Gly Phe Pro Val Asn Arg
    50                  55                  60

Tyr Ser Met Arg Trp Tyr Arg Gln Ala Pro Gly Lys Glu Arg Glu Trp
65                  70                  75                  80

Val Ala Gly Met Ser Ser Ala Gly Asp Arg Ser Ser Tyr Glu Asp Ser
                85                  90                  95

Val Lys Gly Arg Phe Thr Ile Ser Arg Asp Asp Ala Arg Asn Thr Val
```

```
              100               105               110
Tyr Leu Gln Met Asn Ser Leu Lys Pro Glu Asp Thr Ala Val Tyr Tyr
          115               120               125

Cys Asn Val Asn Val Gly Phe Glu Tyr Trp Gly Gln Gly Thr Gln Val
      130               135               140

Thr Val Ser Ser Gly Gly Gly Ser Gly Gly Gly Ser Gly Gly Gly Ser
145               150               155               160

Met Val Ser Lys Gly Glu Glu Asp Asn Met Ala Ile Ile Lys Glu Phe
              165               170               175

Met Arg Phe Lys Val His Met Glu Gly Ser Val Asn Gly His Glu Phe
          180               185               190

Glu Ile Glu Gly Glu Gly Glu Gly Arg Pro Tyr Glu Gly Thr Gln Thr
          195               200               205

Ala Lys Leu Lys Val Thr Lys Gly Gly Pro Leu Pro Phe Ala Trp Asp
      210               215               220

Ile Leu Ser Pro Gln Phe Met Tyr Gly Ser Lys Ala Tyr Val Lys His
225               230               235               240

Pro Ala Asp Ile Pro Asp Tyr Leu Lys Leu Ser Phe Pro Glu Gly Phe
              245               250               255

Lys Trp Glu Arg Val Met Asn Phe Glu Asp Gly Gly Val Val Thr Val
          260               265               270

Thr Gln Asp Ser Ser Leu Gln Asp Gly Glu Phe Ile Tyr Lys Val Lys
          275               280               285

Leu Arg Gly Thr Asn Phe Pro Ser Asp Gly Pro Val Met Gln Lys Lys
      290               295               300

Thr Met Gly Trp Glu Ala Ser Ser Glu Arg Met Tyr Pro Glu Asp Gly
305               310               315               320

Ala Leu Lys Gly Glu Ile Lys Gln Arg Leu Lys Leu Lys Asp Gly Gly
              325               330               335

His Tyr Asp Ala Glu Val Lys Thr Thr Tyr Lys Ala Lys Lys Pro Val
          340               345               350

Gln Leu Pro Gly Ala Tyr Asn Val Asn Ile Lys Leu Asp Ile Thr Ser
          355               360               365

His Asn Glu Asp Tyr Thr Ile Val Glu Gln Tyr Glu Arg Ala Glu Gly
      370               375               380

Arg His Ser Thr Gly Gly Met Asp Glu Leu Tyr Lys Gly Gly Gly Ser
385               390               395               400

Gly Gly Gly Ser Gly Gly Gly Ser Gly Gly Gly Ser Gly Gly Gly Ser
              405               410               415

Met Thr Thr Ala Phe Pro Ser Gln Val Arg Gln Asn Tyr His Gln Asp
          420               425               430

Ser Glu Ala Ala Ile Asn Arg Gln Ile Asn Leu Glu Leu His Ala Ser
          435               440               445

Tyr Val Tyr Leu Ser Met Ser Phe Tyr Phe Asp Arg Asp Asp Val Ala
      450               455               460

Leu Lys Asn Phe Ala Lys Tyr Phe Leu His Gln Ser His Glu Glu Arg
465               470               475               480

Glu His Ala Glu Lys Leu Met Lys Leu Gln Asn Gln Arg Gly Gly Arg
              485               490               495

Ile Phe Leu Gln Asp Ile Lys Lys Pro Asp Gln Asp Asp Trp Glu Asn
          500               505               510

Gly Leu Lys Ala Met Glu Cys Ala Leu His Leu Glu Lys Asn Val Asn
          515               520               525
```

-continued

```
Glu Ser Leu Leu Glu Leu His Lys Leu Ala Thr Asp Lys Asn Asp Pro
    530                 535                 540

His Leu Cys Asp Phe Leu Glu Thr His Tyr Leu Asn Glu Gln Val Lys
545                 550                 555                 560

Ala Ile Lys Glu Leu Gly Asp His Val Thr Asn Leu Arg Arg Met Gly
                565                 570                 575

Ala Pro Glu Ser Gly Met Ala Glu Tyr Leu Phe Asp Lys His Thr Leu
                580                 585                 590

Gly Glu Cys Asp Glu Ser
            595

<210> SEQ ID NO 26
<211> LENGTH: 662
<212> TYPE: PRT
<213> ORGANISM: Artificial Sequence
<220> FEATURE:
<223> OTHER INFORMATION: Recombinant ferritin sequence

<400> SEQUENCE: 26

Met Asp Tyr Lys Asp His Asp Gly Asp Tyr Lys Asp His Asp Ile Asp
1               5                   10                  15

Tyr Lys Asp Asp Asp Asp Lys Pro Lys Lys Lys Arg Lys Val Gly Met
                20                  25                  30

Ala Asp Val Gln Leu Val Glu Ser Gly Gly Ala Leu Val Gln Pro Gly
            35                  40                  45

Gly Ser Leu Arg Leu Ser Cys Ala Ala Ser Gly Phe Pro Val Asn Arg
        50                  55                  60

Tyr Ser Met Arg Trp Tyr Arg Gln Ala Pro Gly Lys Glu Arg Glu Trp
65                  70                  75                  80

Val Ala Gly Met Ser Ser Ala Gly Asp Arg Ser Ser Tyr Glu Asp Ser
                85                  90                  95

Val Lys Gly Arg Phe Thr Ile Ser Arg Asp Asp Ala Arg Asn Thr Val
                100                 105                 110

Tyr Leu Gln Met Asn Ser Leu Lys Pro Glu Asp Thr Ala Val Tyr Tyr
            115                 120                 125

Cys Asn Val Asn Val Gly Phe Glu Tyr Trp Gly Gln Gly Thr Gln Val
        130                 135                 140

Thr Val Ser Ser Gly Gly Gly Ser Gly Gly Gly Ser Gly Gly Gly Ser
145                 150                 155                 160

Glu Ile Gly Thr Gly Phe Pro Phe Asp Pro His Tyr Val Glu Val Leu
                165                 170                 175

Gly Glu Arg Met His Tyr Val Asp Val Gly Pro Arg Asp Gly Thr Pro
                180                 185                 190

Val Leu Phe Leu His Gly Asn Pro Thr Ser Ser Tyr Val Trp Arg Asn
            195                 200                 205

Ile Ile Pro His Val Ala Pro Thr His Arg Cys Ile Ala Pro Asp Leu
    210                 215                 220

Ile Gly Met Gly Lys Ser Asp Lys Pro Asp Leu Gly Tyr Phe Phe Asp
225                 230                 235                 240

Asp His Val Arg Phe Met Asp Ala Phe Ile Glu Ala Leu Gly Leu Glu
                245                 250                 255

Glu Val Val Leu Val Ile His Asp Trp Gly Ser Ala Leu Gly Phe His
            260                 265                 270

Trp Ala Lys Arg Asn Pro Glu Arg Val Lys Gly Ile Ala Phe Met Glu
    275                 280                 285
```

-continued

```
Phe Ile Arg Pro Ile Pro Thr Trp Asp Glu Trp Pro Glu Phe Ala Arg
    290                 295                 300

Glu Thr Phe Gln Ala Phe Arg Thr Thr Asp Val Gly Arg Lys Leu Ile
305                 310                 315                 320

Ile Asp Gln Asn Val Phe Ile Glu Gly Thr Leu Pro Met Gly Val Val
                325                 330                 335

Arg Pro Leu Thr Glu Val Glu Met Asp His Tyr Arg Glu Pro Phe Leu
            340                 345                 350

Asn Pro Val Asp Arg Glu Pro Leu Trp Arg Phe Pro Asn Glu Leu Pro
            355                 360                 365

Ile Ala Gly Glu Pro Ala Asn Ile Val Ala Leu Val Glu Glu Tyr Met
    370                 375                 380

Asp Trp Leu His Gln Ser Pro Val Pro Lys Leu Leu Phe Trp Gly Thr
385                 390                 395                 400

Pro Gly Val Leu Ile Pro Pro Ala Glu Ala Ala Arg Leu Ala Lys Ser
            405                 410                 415

Leu Pro Asn Cys Lys Ala Val Asp Ile Gly Pro Gly Leu Asn Leu Leu
            420                 425                 430

Gln Glu Asp Asn Pro Asp Leu Ile Gly Ser Glu Ile Ala Arg Trp Leu
            435                 440                 445

Ser Thr Leu Glu Ile Ser Gly Gly Gly Gly Ser Gly Gly Gly Gly
    450                 455                 460

Ser Gly Gly Gly Gly Ser Gly Gly Gly Gly Ser Gly Gly Gly Gly Ser
465                 470                 475                 480

Met Thr Thr Ala Phe Pro Ser Gln Val Arg Gln Asn Tyr His Gln Asp
            485                 490                 495

Ser Glu Ala Ala Ile Asn Arg Gln Ile Asn Leu Glu Leu His Ala Ser
            500                 505                 510

Tyr Val Tyr Leu Ser Met Ser Phe Tyr Phe Asp Arg Asp Asp Val Ala
    515                 520                 525

Leu Lys Asn Phe Ala Lys Tyr Phe Leu His Gln Ser His Glu Glu Arg
    530                 535                 540

Glu His Ala Glu Lys Leu Met Lys Leu Gln Asn Gln Arg Gly Gly Arg
545                 550                 555                 560

Ile Phe Leu Gln Asp Ile Lys Lys Pro Asp Gln Asp Asp Trp Glu Asn
            565                 570                 575

Gly Leu Lys Ala Met Glu Cys Ala Leu His Leu Glu Lys Asn Val Asn
            580                 585                 590

Glu Ser Leu Leu Glu Leu His Lys Leu Ala Thr Asp Lys Asn Asp Pro
    595                 600                 605

His Leu Cys Asp Phe Leu Glu Thr His Tyr Leu Asn Glu Gln Val Lys
    610                 615                 620

Ala Ile Lys Glu Leu Gly Asp His Val Thr Asn Leu Arg Arg Met Gly
625                 630                 635                 640

Ala Pro Glu Ser Gly Met Ala Glu Tyr Leu Phe Asp Lys His Thr Leu
            645                 650                 655

Gly Glu Cys Asp Glu Ser
            660
```

<210> SEQ ID NO 27
<211> LENGTH: 117
<212> TYPE: PRT
<213> ORGANISM: Artificial Sequence
<220> FEATURE:

-continued

<223> OTHER INFORMATION: MS2 binding protein

<400> SEQUENCE: 27

```
Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Ile Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Gly Ala Trp Arg Ser Tyr Leu Asn Met Glu Leu Thr Ile
65                  70                  75                  80

Pro Ile Phe Ala Thr Asn Ser Asp Cys Glu Leu Ile Val Lys Ala Met
                85                  90                  95

Gln Gly Leu Leu Lys Asp Gly Asn Pro Ile Pro Ser Ala Ile Ala Ala
            100                 105                 110

Asn Ser Gly Ile Tyr
        115
```

<210> SEQ ID NO 28
<211> LENGTH: 23
<212> TYPE: PRT
<213> ORGANISM: Artificial Sequence
<220> FEATURE:
<223> OTHER INFORMATION: lambda N22 RNA binding protein

<400> SEQUENCE: 28

```
Met Gly Asn Ala Arg Thr Arg Arg Arg Glu Arg Arg Ala Glu Lys Gln
1               5                   10                  15

Ala Gln Trp Lys Ala Ala Asn
            20
```

<210> SEQ ID NO 29
<211> LENGTH: 123
<212> TYPE: PRT
<213> ORGANISM: Artificial Sequence
<220> FEATURE:
<223> OTHER INFORMATION: PP7 RNA stem loop coat protein

<400> SEQUENCE: 29

```
Met Gly Ser Lys Thr Ile Val Leu Ser Val Gly Glu Ala Thr Arg Thr
1               5                   10                  15

Leu Thr Glu Ile Gln Ser Thr Ala Asp Arg Gln Ile Phe Glu Glu Lys
            20                  25                  30

Val Gly Pro Leu Val Gly Arg Leu Arg Leu Thr Ala Ser Leu Arg Gln
        35                  40                  45

Asn Gly Ala Lys Thr Ala Tyr Arg Val Asn Leu Lys Leu Asp Gln Ala
    50                  55                  60

Asp Val Val Asp Ser Gly Leu Pro Lys Val Arg Tyr Thr Gln Val Trp
65                  70                  75                  80

Ser His Asp Val Thr Ile Val Ala Asn Ser Thr Glu Ala Ser Arg Lys
                85                  90                  95

Ser Leu Tyr Asp Leu Thr Lys Ser Leu Val Ala Thr Ser Gln Val Glu
            100                 105                 110

Asp Leu Val Val Asn Leu Val Pro Leu Gly Arg
        115                 120
```

```
<210> SEQ ID NO 30
<211> LENGTH: 247
<212> TYPE: PRT
<213> ORGANISM: Artificial Sequence
<220> FEATURE:
<223> OTHER INFORMATION: anti-suntag scFv

<400> SEQUENCE: 30

Met Gly Pro Asp Ile Val Met Thr Gln Ser Pro Ser Ser Leu Ser Ala
1               5                   10                  15

Ser Val Gly Asp Arg Val Thr Ile Thr Cys Arg Ser Ser Thr Gly Ala
            20                  25                  30

Val Thr Thr Ser Asn Tyr Ala Ser Trp Val Gln Glu Lys Pro Gly Lys
        35                  40                  45

Leu Phe Lys Gly Leu Ile Gly Gly Thr Asn Asn Arg Ala Pro Gly Val
    50                  55                  60

Pro Ser Arg Phe Ser Gly Ser Leu Ile Gly Asp Lys Ala Thr Leu Thr
65                  70                  75                  80

Ile Ser Ser Leu Gln Pro Glu Asp Phe Ala Thr Tyr Phe Cys Ala Leu
                85                  90                  95

Trp Tyr Ser Asn His Trp Val Phe Gly Gln Gly Thr Lys Val Glu Leu
            100                 105                 110

Lys Arg Gly Gly Gly Gly Ser Gly Gly Gly Gly Ser Gly Gly Gly Gly
            115                 120                 125

Ser Ser Gly Gly Gly Ser Glu Val Lys Leu Leu Glu Ser Gly Gly Gly
        130                 135                 140

Leu Val Gln Pro Gly Gly Ser Leu Lys Leu Ser Cys Ala Val Ser Gly
145                 150                 155                 160

Phe Ser Leu Thr Asp Tyr Gly Val Asn Trp Val Arg Gln Ala Pro Gly
                165                 170                 175

Arg Gly Leu Glu Trp Ile Gly Val Ile Trp Gly Asp Gly Ile Thr Asp
            180                 185                 190

Tyr Asn Ser Ala Leu Lys Asp Arg Phe Ile Ile Ser Lys Asp Asn Gly
            195                 200                 205

Lys Asn Thr Val Tyr Leu Gln Met Ser Lys Val Arg Ser Asp Asp Thr
        210                 215                 220

Ala Leu Tyr Tyr Cys Val Thr Gly Leu Phe Asp Tyr Trp Gly Gln Gly
225                 230                 235                 240

Thr Leu Val Thr Val Ser Ser
                245

<210> SEQ ID NO 31
<211> LENGTH: 129
<212> TYPE: PRT
<213> ORGANISM: Artificial Sequence
<220> FEATURE:
<223> OTHER INFORMATION: anti-mCherry VHH

<400> SEQUENCE: 31

Met Ala Gln Val Gln Leu Val Glu Ser Gly Gly Ser Leu Val Gln Pro
1               5                   10                  15

Gly Gly Ser Leu Arg Leu Ser Cys Ala Ala Ser Gly Arg Phe Ala Glu
            20                  25                  30

Ser Ser Ser Met Gly Trp Phe Arg Gln Ala Pro Gly Lys Glu Arg Glu
        35                  40                  45

Phe Val Ala Ala Ile Ser Trp Ser Gly Gly Ala Thr Asn Tyr Ala Asp
    50                  55                  60
```

-continued

Ser Ala Lys Gly Arg Phe Thr Leu Ser Arg Asp Asn Thr Lys Asn Thr
65                  70                  75                  80

Val Tyr Leu Gln Met Asn Ser Leu Lys Pro Asp Asp Thr Ala Val Tyr
                85                  90                  95

Tyr Cys Ala Ala Asn Leu Gly Asn Tyr Ile Ser Ser Asn Gln Arg Leu
                100                 105                 110

Tyr Gly Tyr Trp Gly Gln Gly Thr Gln Val Thr Val Ser Ser Pro Phe
                115                 120                 125

Thr

<210> SEQ ID NO 32
<211> LENGTH: 354
<212> TYPE: PRT
<213> ORGANISM: Artificial Sequence
<220> FEATURE:
<223> OTHER INFORMATION: PUFa

<400> SEQUENCE: 32

Ser Arg Gly Arg Ser Arg Leu Leu Glu Asp Phe Arg Asn Asn Arg Tyr
1               5                   10                  15

Pro Asn Leu Gln Leu Arg Glu Ile Ala Gly His Ile Met Glu Phe Ser
                20                  25                  30

Gln Asp Gln His Gly Ser Arg Phe Ile Gln Leu Lys Leu Glu Arg Ala
                35                  40                  45

Thr Pro Ala Glu Arg Gln Leu Val Phe Asn Glu Ile Leu Gln Ala Ala
                50                  55                  60

Tyr Gln Leu Met Val Asp Val Phe Gly Asn Tyr Val Ile Gln Lys Phe
65                  70                  75                  80

Phe Glu Phe Gly Ser Leu Glu Gln Lys Leu Ala Leu Ala Glu Arg Ile
                85                  90                  95

Arg Gly His Val Leu Ser Leu Ala Leu Gln Met Tyr Gly Ser Arg Val
                100                 105                 110

Ile Glu Lys Ala Leu Glu Phe Ile Pro Ser Asp Gln Gln Asn Glu Met
                115                 120                 125

Val Arg Glu Leu Asp Gly His Val Leu Lys Cys Val Lys Asp Gln Asn
                130                 135                 140

Gly Asn His Val Val Gln Lys Cys Ile Glu Cys Val Gln Pro Gln Ser
145                 150                 155                 160

Leu Gln Phe Ile Ile Asp Ala Phe Lys Gly Gln Val Phe Ala Leu Ser
                165                 170                 175

Thr His Pro Tyr Gly Cys Arg Val Ile Gln Arg Ile Leu Glu His Cys
                180                 185                 190

Leu Pro Asp Gln Thr Leu Pro Ile Leu Glu Glu Leu His Gln His Thr
                195                 200                 205

Glu Gln Leu Val Gln Asp Gln Tyr Gly Asn Tyr Val Ile Gln His Val
                210                 215                 220

Leu Glu His Gly Arg Pro Glu Asp Lys Ser Lys Ile Val Ala Glu Ile
225                 230                 235                 240

Arg Gly Asn Val Leu Val Leu Ser Gln His Lys Phe Ala Ser Asn Val
                245                 250                 255

Val Glu Lys Cys Val Thr His Ala Ser Arg Thr Glu Arg Ala Val Leu
                260                 265                 270

Ile Asp Glu Val Cys Thr Met Asn Asp Gly Pro His Ser Ala Leu Tyr
                275                 280                 285

Thr Met Met Lys Asp Gln Tyr Ala Asn Tyr Val Val Gln Lys Met Ile

-continued

```
        290              295              300

Asp Val Ala Glu Pro Gly Gln Arg Lys Ile Val Met His Lys Ile Arg
305                 310              315              320

Pro His Ile Ala Thr Leu Arg Lys Tyr Thr Tyr Gly Lys His Ile Leu
                325              330              335

Ala Lys Leu Glu Lys Tyr Tyr Met Lys Asn Gly Val Asp Leu Gly Gly
            340              345              350

Pro Ala

<210> SEQ ID NO 33
<211> LENGTH: 354
<212> TYPE: PRT
<213> ORGANISM: Artificial Sequence
<220> FEATURE:
<223> OTHER INFORMATION: PUFb

<400> SEQUENCE: 33

Ser Arg Gly Arg Ser Arg Leu Leu Glu Asp Phe Arg Asn Asn Arg Tyr
1               5                10               15

Pro Asn Leu Gln Leu Arg Glu Ile Ala Gly His Ile Met Glu Phe Ser
            20               25               30

Gln Asp Gln His Gly Ser Arg Phe Ile Gln Leu Lys Leu Glu Arg Ala
        35               40               45

Thr Pro Ala Glu Arg Gln Leu Val Phe Asn Glu Ile Leu Gln Ala Ala
    50               55               60

Tyr Gln Leu Met Val Asp Val Phe Gly Asn Tyr Val Ile Gln Lys Phe
65               70               75               80

Phe Glu Phe Gly Ser Leu Glu Gln Lys Leu Ala Leu Ala Glu Arg Ile
            85               90               95

Arg Gly His Val Leu Ser Leu Ala Leu Gln Met Tyr Gly Cys Arg Val
        100              105              110

Ile Gln Lys Ala Leu Glu Phe Ile Pro Ser Asp Gln Gln Asn Glu Met
        115              120              125

Val Arg Glu Leu Asp Gly His Val Leu Lys Cys Val Lys Asp Gln Asn
    130              135              140

Gly Asn His Val Val Gln Lys Cys Ile Glu Cys Val Gln Pro Gln Ser
145              150              155              160

Leu Gln Phe Ile Ile Asp Ala Phe Lys Gly Gln Val Phe Ala Leu Ser
            165              170              175

Thr His Pro Tyr Gly Cys Arg Val Ile Gln Arg Ile Leu Glu His Cys
            180              185              190

Leu Pro Asp Gln Thr Leu Pro Ile Leu Glu Glu Leu His Gln His Thr
        195              200              205

Glu Gln Leu Val Gln Asp Gln Tyr Gly Ser Tyr Val Ile Glu His Val
        210              215              220

Leu Glu His Gly Arg Pro Glu Asp Lys Ser Lys Ile Val Ala Glu Ile
225              230              235              240

Arg Gly Asn Val Leu Val Leu Ser Gln His Lys Phe Ala Asn Asn Val
            245              250              255

Val Gln Lys Cys Val Thr His Ala Ser Arg Thr Glu Arg Ala Val Leu
            260              265              270

Ile Asp Glu Val Cys Thr Met Asn Asp Gly Pro His Ser Ala Leu Tyr
        275              280              285

Thr Met Met Lys Asp Gln Tyr Ala Asn Tyr Val Val Gln Lys Met Ile
    290              295              300
```

Asp Val Ala Glu Pro Gly Gln Arg Lys Ile Val Met His Lys Ile Arg
305               310              315              320

Pro His Ile Ala Thr Leu Arg Lys Tyr Thr Tyr Gly Lys His Ile Leu
              325              330              335

Ala Lys Leu Glu Lys Tyr Tyr Met Lys Asn Gly Val Asp Leu Gly Gly
          340              345              350

Pro Ala

<210> SEQ ID NO 34
<211> LENGTH: 90
<212> TYPE: PRT
<213> ORGANISM: Artificial Sequence
<220> FEATURE:
<223> OTHER INFORMATION: FRB

<400> SEQUENCE: 34

Glu Met Trp His Glu Gly Leu Glu Glu Ala Ser Arg Leu Tyr Phe Gly
1               5              10              15

Glu Arg Asn Val Lys Gly Met Phe Glu Val Leu Glu Pro Leu His Ala
              20              25              30

Met Met Glu Arg Gly Pro Gln Thr Leu Lys Glu Thr Ser Phe Asn Gln
          35              40              45

Ala Tyr Gly Arg Asp Leu Met Glu Ala Gln Glu Trp Cys Arg Lys Tyr
      50              55              60

Met Lys Ser Gly Asn Val Lys Asp Leu Leu Gln Ala Trp Asp Leu Tyr
65              70              75              80

Tyr His Val Phe Arg Arg Ile Ser Lys Gln
              85              90

<210> SEQ ID NO 35
<211> LENGTH: 106
<212> TYPE: PRT
<213> ORGANISM: Artificial Sequence
<220> FEATURE:
<223> OTHER INFORMATION: FKBP

<400> SEQUENCE: 35

Gly Val Gln Val Glu Thr Ile Ser Pro Gly Asp Gly Arg Thr Phe Pro
1               5              10              15

Lys Arg Gly Gln Thr Cys Val Val His Tyr Thr Gly Met Leu Glu Asp
              20              25              30

Gly Lys Lys Phe Asp Ser Ser Arg Asp Arg Asn Lys Pro Phe Lys Phe
          35              40              45

Met Leu Gly Lys Gln Glu Val Ile Arg Gly Trp Glu Glu Gly Val Ala
      50              55              60

Gln Met Ser Val Gly Gln Arg Ala Lys Leu Thr Ile Ser Pro Asp Tyr
65              70              75              80

Ala Tyr Gly Ala Thr Gly His Pro Gly Ile Ile Pro Pro His Ala Thr
              85              90              95

Leu Val Phe Asp Val Glu Leu Leu Lys Leu
          100              105

<210> SEQ ID NO 36
<211> LENGTH: 1367
<212> TYPE: PRT
<213> ORGANISM: Artificial Sequence
<220> FEATURE:
<223> OTHER INFORMATION: dSpCas9

-continued

<400> SEQUENCE: 36

Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
                20                  25                  30

Val Leu Gly Asn Thr Asp Arg His Ser Ile Lys Lys Asn Leu Ile Gly
            35                  40                  45

Ala Leu Leu Phe Asp Ser Gly Glu Thr Ala Glu Ala Thr Arg Leu Lys
        50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
            115                 120                 125

Glu Lys Tyr Pro Thr Ile Tyr His Leu Arg Lys Lys Leu Val Asp Ser
        130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
                180                 185                 190

Gln Leu Phe Glu Glu Asn Pro Ile Asn Ala Ser Gly Val Asp Ala Lys
            195                 200                 205

Ala Ile Leu Ser Ala Arg Leu Ser Lys Ser Arg Arg Leu Glu Asn Leu
        210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
        290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
            355                 360                 365

Glu Glu Phe Tyr Lys Phe Ile Lys Pro Ile Leu Glu Lys Met Asp Gly
        370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

```
Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
            435                 440                 445

Tyr Tyr Val Gly Pro Leu Ala Arg Gly Asn Ser Arg Phe Ala Trp Met
        450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
            515                 520                 525

Val Thr Glu Gly Met Arg Lys Pro Ala Phe Leu Ser Gly Glu Gln Lys
        530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
            565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
            595                 600                 605

Glu Glu Asn Glu Asp Ile Leu Glu Asp Ile Val Leu Thr Leu Thr Leu
            610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
            675                 680                 685

Asn Arg Asn Phe Met Gln Leu Ile His Asp Asp Ser Leu Thr Phe Lys
            690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
            755                 760                 765

Thr Gln Lys Gly Gln Lys Asn Ser Arg Glu Arg Met Lys Arg Ile Glu
        770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830
```

```
Ser Asp Tyr Asp Val Asp Ala Ile Val Pro Gln Ser Phe Leu Lys Asp
    835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
                900                 905                 910

Ala Gly Phe Ile Lys Arg Gln Leu Val Glu Thr Arg Gln Ile Thr Lys
            915                 920                 925

His Val Ala Gln Ile Leu Asp Ser Arg Met Asn Thr Lys Tyr Asp Glu
        930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
                980                 985                 990

Gly Thr Ala Leu Ile Lys Lys Tyr  Pro Lys Leu Glu Ser  Glu Phe Val
            995                 1000                1005

Tyr Gly  Asp Tyr Lys Val Tyr  Asp Val Arg Lys Met  Ile Ala Lys
    1010                1015                1020

Ser Glu  Gln Glu Ile Gly Lys  Ala Thr Ala Lys Tyr  Phe Phe Tyr
    1025                1030                1035

Ser Asn  Ile Met Asn Phe Phe  Lys Thr Glu Ile Thr  Leu Ala Asn
    1040                1045                1050

Gly Glu  Ile Arg Lys Arg Pro  Leu Ile Glu Thr Asn  Gly Glu Thr
    1055                1060                1065

Gly Glu  Ile Val Trp Asp Lys  Gly Arg Asp Phe Ala  Thr Val Arg
    1070                1075                1080

Lys Val  Leu Ser Met Pro Gln  Val Asn Ile Val Lys  Lys Thr Glu
    1085                1090                1095

Val Gln  Thr Gly Gly Phe Ser  Lys Glu Ser Ile Leu  Pro Lys Arg
    1100                1105                1110

Asn Ser  Asp Lys Leu Ile Ala  Arg Lys Lys Asp Trp  Asp Pro Lys
    1115                1120                1125

Lys Tyr  Gly Gly Phe Asp Ser  Pro Thr Val Ala Tyr  Ser Val Leu
    1130                1135                1140

Val Val  Ala Lys Val Glu Lys  Gly Lys Ser Lys Lys  Leu Lys Ser
    1145                1150                1155

Val Lys  Glu Leu Leu Gly Ile  Thr Ile Met Glu Arg  Ser Ser Phe
    1160                1165                1170

Glu Lys  Asn Pro Ile Asp Phe  Leu Glu Ala Lys Gly  Tyr Lys Glu
    1175                1180                1185

Val Lys  Lys Asp Leu Ile Ile  Lys Leu Pro Lys Tyr  Ser Leu Phe
    1190                1195                1200

Glu Leu  Glu Asn Gly Arg Lys  Arg Met Leu Ala Ser  Ala Gly Glu
    1205                1210                1215

Leu Gln  Lys Gly Asn Glu Leu  Ala Leu Pro Ser Lys  Tyr Val Asn
    1220                1225                1230

Phe Leu  Tyr Leu Ala Ser His  Tyr Glu Lys Leu Lys  Gly Ser Pro
```

-continued

```
      1235                1240                1245

Glu Asp  Asn Glu Gln Lys Gln  Leu Phe Val Glu Gln  His Lys His
      1250                1255                1260

Tyr Leu  Asp Glu Ile Ile Glu  Gln Ile Ser Glu Phe  Ser Lys Arg
      1265                1270                1275

Val Ile  Leu Ala Asp Ala Asn  Leu Asp Lys Val Leu  Ser Ala Tyr
      1280                1285                1290

Asn Lys  His Arg Asp Lys Pro  Ile Arg Glu Gln Ala  Glu Asn Ile
      1295                1300                1305

Ile His  Leu Phe Thr Leu Thr  Asn Leu Gly Ala Pro  Ala Ala Phe
      1310                1315                1320

Lys Tyr  Phe Asp Thr Thr Ile  Asp Arg Lys Arg Tyr  Thr Ser Thr
      1325                1330                1335

Lys Glu  Val Leu Asp Ala Thr  Leu Ile His Gln Ser  Ile Thr Gly
      1340                1345                1350

Leu Tyr  Glu Thr Arg Ile Asp  Leu Ser Gln Leu Gly  Gly Asp
      1355                1360                1365
```

```
<210> SEQ ID NO 37
<211> LENGTH: 12
<212> TYPE: PRT
<213> ORGANISM: Artificial Sequence
<220> FEATURE:
<223> OTHER INFORMATION: glycine-serine peptide linker

<400> SEQUENCE: 37

Gly Gly Gly Ser Gly Gly Gly Ser Gly Gly Gly Ser
1               5                   10

<210> SEQ ID NO 38
<211> LENGTH: 885
<212> TYPE: DNA
<213> ORGANISM: Artificial Sequence
<220> FEATURE:
<223> OTHER INFORMATION: halo tag

<400> SEQUENCE: 38
gaaatcggta ctggctttcc attcgacccc cattatgtgg aagtcctggg cgagcgcatg      60
cactacgtcg atgttggtcc gcgcgatggc acccctgtgc tgttcctgca cggtaacccg     120
acctcctcct acgtgtggcg caacatcatc ccgcatgttg caccgaccca tcgctgcatt     180
gctccagacc tgatcggtat gggcaaatcc gacaaaccag acctgggtta tttcttcgac     240
gaccacgtcc gcttcatgga tgccttcatc gaagccctgg gtctggaaga ggtcgtcctg     300
gtcattcacg actggggctc cgctctgggt ttccactggg ccaagcgcaa tccagagcgc     360
gtcaaaggta ttgcatttat ggagttcatc cgccctatcc cgacctggga cgaatggcca     420
gaatttgccc gcgagacctt ccaggccttc cgcaccaccg acgtcggccg caagctgatc     480
atcgatcaga acgtttttat cgagggtacg ctgccgatgg gtgtcgtccg cccgctgact     540
gaagtcgaga tggaccatta ccgcgagccg ttcctgaatc ctgttgaccg cgagccactg     600
tggcgcttcc caaacgagct gccaatcgcc ggtgagccag cgaacatcgt cgcgctggtc     660
gaagaataca tggactggct gcaccagtcc cctgtcccga gctgctgtt ctggggcacc     720 ccaggcgttc tgatcccacc ggccgaagcc gctcgcctgg ccaaaagcct gcctaactgc     780
aaggctgtgg acatcggccc gggtctgaat ctgctgcaag aagacaaccc ggacctgatc     840
ggcagcgaga tcgcgcgctg gctgtccacg ctcgagattt ccggc                     885
```

-continued

<210> SEQ ID NO 39
<211> LENGTH: 295
<212> TYPE: PRT
<213> ORGANISM: Artificial Sequence
<220> FEATURE:
<223> OTHER INFORMATION: halotag

<400> SEQUENCE: 39

Glu Ile Gly Thr Gly Phe Pro Phe Asp Pro His Tyr Val Glu Val Leu
1               5                   10                  15

Gly Glu Arg Met His Tyr Val Asp Val Gly Pro Arg Asp Gly Thr Pro
            20                  25                  30

Val Leu Phe Leu His Gly Asn Pro Thr Ser Ser Tyr Val Trp Arg Asn
        35                  40                  45

Ile Ile Pro His Val Ala Pro Thr His Arg Cys Ile Ala Pro Asp Leu
    50                  55                  60

Ile Gly Met Gly Lys Ser Asp Lys Pro Asp Leu Gly Tyr Phe Phe Asp
65                  70                  75                  80

Asp His Val Arg Phe Met Asp Ala Phe Ile Glu Ala Leu Gly Leu Glu
                85                  90                  95

Glu Val Val Leu Val Ile His Asp Trp Gly Ser Ala Leu Gly Phe His
            100                 105                 110

Trp Ala Lys Arg Asn Pro Glu Arg Val Lys Gly Ile Ala Phe Met Glu
            115                 120                 125

Phe Ile Arg Pro Ile Pro Thr Trp Asp Glu Trp Pro Glu Phe Ala Arg
    130                 135                 140

Glu Thr Phe Gln Ala Phe Arg Thr Thr Asp Val Gly Arg Lys Leu Ile
145                 150                 155                 160

Ile Asp Gln Asn Val Phe Ile Glu Gly Thr Leu Pro Met Gly Val Val
                165                 170                 175

Arg Pro Leu Thr Glu Val Glu Met Asp His Tyr Arg Glu Pro Phe Leu
            180                 185                 190

Asn Pro Val Asp Arg Glu Pro Leu Trp Arg Phe Pro Asn Glu Leu Pro
            195                 200                 205

Ile Ala Gly Glu Pro Ala Asn Ile Val Ala Leu Val Glu Glu Tyr Met
    210                 215                 220

Asp Trp Leu His Gln Ser Pro Val Pro Lys Leu Leu Phe Trp Gly Thr
225                 230                 235                 240

Pro Gly Val Leu Ile Pro Pro Ala Glu Ala Ala Arg Leu Ala Lys Ser
            245                 250                 255

Leu Pro Asn Cys Lys Ala Val Asp Ile Gly Pro Gly Leu Asn Leu Leu
            260                 265                 270

Gln Glu Asp Asn Pro Asp Leu Ile Gly Ser Glu Ile Ala Arg Trp Leu
            275                 280                 285

Ser Thr Leu Glu Ile Ser Gly
    290                 295

<210> SEQ ID NO 40
<211> LENGTH: 708
<212> TYPE: DNA
<213> ORGANISM: Artificial Sequence
<220> FEATURE:
<223> OTHER INFORMATION: mCherry

<400> SEQUENCE: 40
atggttagca agggcgagga ggataatatg gccattatca aagaattcat gcgctttaag      60

```
gtccacatgg agggtagtgt caacggtcat gaatttgaga tagagggtga aggggaaggt    120
aggccttacg agggtactca aactgcgaaa ttgaaagtca caaaggggggg tcccctccct    180 tttgcgtggg atatactctc cccacaattt atgtacggtt caaaagccta tgttaagcac    240
cctgcggaca tccccgacta cctgaaactc agttttcctg aaggcttcaa gtgggagcgg    300
gtcatgaatt ttgaggacgg tggggtcgta acggtcactc aggactcatc tcttcaagat    360
ggtgagttta tctataaagt aaagttgcgc ggtactaact ttccgtccga cggaccagta    420
atgcaaaaaa aaacaatggg ttgggaggct tcatccgaac ggatgtatcc cgaagacggg    480
gctctcaagg gtgagattaa acaaaggctt aaactgaagg atggaggcca ttacgatgct    540
gaagttaaaa ccacgtataa agcgaagaaa cccgttcagc tgcctggtgc atataatgtg    600
aatatcaaat tggatataac ctcacacaat gaggactata ctatcgtaga acaatatgaa    660
cgggcggaag gacgacactc aaccgggggga atggatgaac tttataaa           708
```

```
<210> SEQ ID NO 41
<211> LENGTH: 236
<212> TYPE: PRT
<213> ORGANISM: Artificial Sequence
<220> FEATURE:
<223> OTHER INFORMATION: mCherry

<400> SEQUENCE: 41

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235
```

```
<210> SEQ ID NO 42
```

```
<211> LENGTH: 1701
<212> TYPE: DNA
<213> ORGANISM: Artificial Sequence
<220> FEATURE:
<223> OTHER INFORMATION: Recombinant ferritin sequence

<400> SEQUENCE: 42
atggatgtgc agttggttga gtctggcggg gcactcgtgc agccgggggg tagtctgaga       60
ttgagttgtg ccgcctccgg atttccagtc aacagatatt caatgcgctg gtatcgacag      120
gcgccaggga aagagagaga atgggttgcg ggtatgtcat cagcgggtga tcgatcctct      180
tacgaggatt cagtgaaagg gcggtttaca ataagccgag atgacgccag aaatacggta      240
tacctccaga tgaactccct caagccggaa gatacggcag tttactattg taacgttaat      300
gttggatttg agtattgggg ccaaggaacg caagtgaccg tcagcagtgg tggtggaagt      360
ggcggagggt caggaggcgg atctatggtt agcaagggcg aggaggataa tatggccatt      420
atcaaagaat tcatgcgctt taaggtccac atggagggta gtgtcaacgg tcatgaattt      480
gagatagagg gtgaagggga aggtaggcct tacgagggta ctcaaactgc gaaattgaaa      540
gtcacaaagg ggggtcccct ccctttttgcg tgggatatac tctccccaca atttatgtac      600
ggttcaaaag cctatgttaa gcaccctgcg gacatccccg actacctgaa actcagtttt      660
cctgaaggct tcaagtggga gcgggtcatg aattttgagg acggtggggt cgtaacggtc      720
actcaggact catctcttca agatggtgag tttatctata aagtaaagtt gcgcggtact      780
aactttccgt ccgacggacc agtaatgcaa aaaaaacaa tgggttggga ggcttcatcc       840
gaacggatgt atcccgaaga cggggctctc aagggtgaga ttaaacaaag gcttaaactg      900
aaggatggag gccattacga tgctgaagtt aaaaccacgt ataaagcgaa gaaacccgtt      960
cagctgcctg gtgcatataa tgtgaatatc aaattggata taacctcaca caatgaggac     1020
tatactatcg tagaacaata tgaacgggcg gaaggacgac actcaaccgg gggaatggat     1080
gaactttata aaggggaagg aagcgggga gggtctgggg gtggttcagg cggggggatca     1140 ggtggcggga gtatgactac tgcattcccg agccaagtgc ggcagaatta ccaccaggac     1200
tctgaagcgg ccatcaaccg acaaatcaac ctggaactgc atgcgtctta cgtttatctg     1260
tcaatgagct tttactttga tagagacgat gtcgcattga agaacttcgc caaatatttt     1320
cttcatcaga gccatgagga aagggaacat gcagaaaaac ttatgaaatt gcagaaccag     1380
cgcggtggaa ggattttcct ccaagacata aagaaaccgg atcaggacga ctgggagaat     1440
ggcctgaagg caatggaatg tgcacttcac ctcgaaaaga cgtgaacga gagcctcctg     1500 gaactgcata aattggccac tgacaaaaac gatccacacc tgtgcgattt ccttgagact     1560
cattatctta cgagcaagt gaaagcaatt aaagagttgg gtgatcatgt cactaacctg     1620
agacgcatgg gggcaccaga aagcggcatg gcagagtatt tgtttgacaa gcatacactt     1680
ggtgagtgtg acgagtcttg a                                              1701

<210> SEQ ID NO 43
<211> LENGTH: 565
<212> TYPE: PRT
<213> ORGANISM: Artificial Sequence
<220> FEATURE:
<223> OTHER INFORMATION: Recombinant ferritin sequence

<400> SEQUENCE: 43

Asp Val Gln Leu Val Glu Ser Gly Gly Ala Leu Val Gln Pro Gly Gly
1               5                   10                  15
```

```
Ser Leu Arg Leu Ser Cys Ala Ala Ser Gly Phe Pro Val Asn Arg Tyr
        20              25                  30

Ser Met Arg Trp Tyr Arg Gln Ala Pro Gly Lys Glu Arg Glu Trp Val
        35              40              45

Ala Gly Met Ser Ser Ala Gly Asp Arg Ser Ser Tyr Glu Asp Ser Val
        50              55              60

Lys Gly Arg Phe Thr Ile Ser Arg Asp Asp Ala Arg Asn Thr Val Tyr
65              70              75              80

Leu Gln Met Asn Ser Leu Lys Pro Glu Asp Thr Ala Val Tyr Tyr Cys
            85              90                  95

Asn Val Asn Val Gly Phe Glu Tyr Trp Gly Gln Gly Thr Gln Val Thr
            100             105             110

Val Ser Ser Gly Gly Gly Ser Gly Gly Gly Ser Gly Gly Gly Ser Met
        115             120             125

Val Ser Lys Gly Glu Glu Asp Asn Met Ala Ile Ile Lys Glu Phe Met
        130             135             140

Arg Phe Lys Val His Met Glu Gly Ser Val Asn Gly His Glu Phe Glu
145             150             155             160

Ile Glu Gly Glu Gly Glu Gly Arg Pro Tyr Glu Gly Thr Gln Thr Ala
            165             170             175

Lys Leu Lys Val Thr Lys Gly Gly Pro Leu Pro Phe Ala Trp Asp Ile
            180             185             190

Leu Ser Pro Gln Phe Met Tyr Gly Ser Lys Ala Tyr Val Lys His Pro
        195             200             205

Ala Asp Ile Pro Asp Tyr Leu Lys Leu Ser Phe Pro Glu Gly Phe Lys
        210             215             220

Trp Glu Arg Val Met Asn Phe Glu Asp Gly Gly Val Val Thr Val Thr
225             230             235             240

Gln Asp Ser Ser Leu Gln Asp Gly Glu Phe Ile Tyr Lys Val Lys Leu
            245             250             255

Arg Gly Thr Asn Phe Pro Ser Asp Gly Pro Val Met Gln Lys Lys Thr
            260             265             270

Met Gly Trp Glu Ala Ser Ser Glu Arg Met Tyr Pro Glu Asp Gly Ala
        275             280             285

Leu Lys Gly Glu Ile Lys Gln Arg Leu Lys Leu Lys Asp Gly Gly His
        290             295             300

Tyr Asp Ala Glu Val Lys Thr Thr Tyr Lys Ala Lys Lys Pro Val Gln
305             310             315             320

Leu Pro Gly Ala Tyr Asn Val Asn Ile Lys Leu Asp Ile Thr Ser His
            325             330             335

Asn Glu Asp Tyr Thr Ile Val Glu Gln Tyr Glu Arg Ala Glu Gly Arg
            340             345             350

His Ser Thr Gly Gly Met Asp Glu Leu Tyr Lys Gly Gly Gly Ser Gly
        355             360             365

Gly Gly Ser Gly Gly Gly Ser Gly Gly Gly Ser Gly Gly Gly Ser Met
        370             375             380

Thr Thr Ala Phe Pro Ser Gln Val Arg Gln Asn Tyr His Gln Asp Ser
385             390             395             400

Glu Ala Ala Ile Asn Arg Gln Ile Asn Leu Glu Leu His Ala Ser Tyr
            405             410             415

Val Tyr Leu Ser Met Ser Phe Tyr Phe Asp Arg Asp Asp Val Ala Leu
            420             425             430

Lys Asn Phe Ala Lys Tyr Phe Leu His Gln Ser His Glu Glu Arg Glu
```

```
            435                 440                 445
His Ala Glu Lys Leu Met Lys Leu Gln Asn Gln Arg Gly Gly Arg Ile
    450                 455                 460

Phe Leu Gln Asp Ile Lys Lys Pro Asp Gln Asp Asp Trp Glu Asn Gly
465                 470                 475                 480

Leu Lys Ala Met Glu Cys Ala Leu His Leu Glu Lys Asn Val Asn Glu
                485                 490                 495

Ser Leu Leu Glu Leu His Lys Leu Ala Thr Asp Lys Asn Asp Pro His
            500                 505                 510

Leu Cys Asp Phe Leu Glu Thr His Tyr Leu Asn Glu Gln Val Lys Ala
            515                 520                 525

Ile Lys Glu Leu Gly Asp His Val Thr Asn Leu Arg Arg Met Gly Ala
        530                 535                 540

Pro Glu Ser Gly Met Ala Glu Tyr Leu Phe Asp Lys His Thr Leu Gly
545                 550                 555                 560

Glu Cys Asp Glu Ser
                565
```

```
<210> SEQ ID NO 44
<211> LENGTH: 345
<212> TYPE: DNA
<213> ORGANISM: Artificial Sequence
<220> FEATURE:
<223> OTHER INFORMATION: anti-GFP VHH

<400> SEQUENCE: 44
gatgtgcagt tggttgagtc tggcggggca ctcgtgcagc cgggggggtag tctgagattg        60 agttgtgccg cctccggatt tccagtcaac agatattcaa tgcgctggta tcgacaggcg        120
ccagggaaag agagagaatg ggttgcgggt atgtcatcag cgggtgatcg atcctcttac        180
gaggattcag tgaaagggcg gtttacaata agccgagatg acgccagaaa tacggtatac        240
ctccagatga actccctcaa gccggaagat acggcagttt actattgtaa cgttaatgtt        300
ggatttgagt attggggcca aggaacgcaa gtgaccgtca gcagt                         345
```

```
<210> SEQ ID NO 45
<211> LENGTH: 115
<212> TYPE: PRT
<213> ORGANISM: Artificial Sequence
<220> FEATURE:
<223> OTHER INFORMATION: anti-GFP VHH

<400> SEQUENCE: 45

Asp Val Gln Leu Val Glu Ser Gly Gly Ala Leu Val Gln Pro Gly Gly
1               5                   10                  15

Ser Leu Arg Leu Ser Cys Ala Ala Ser Gly Phe Pro Val Asn Arg Tyr
            20                  25                  30

Ser Met Arg Trp Tyr Arg Gln Ala Pro Gly Lys Glu Arg Glu Trp Val
        35                  40                  45

Ala Gly Met Ser Ser Ala Gly Asp Arg Ser Ser Tyr Glu Asp Ser Val
    50                  55                  60

Lys Gly Arg Phe Thr Ile Ser Arg Asp Asp Ala Arg Asn Thr Val Tyr
65                  70                  75                  80

Leu Gln Met Asn Ser Leu Lys Pro Glu Asp Thr Ala Val Tyr Tyr Cys
                85                  90                  95
```

-continued

```
Asn Val Asn Val Gly Phe Glu Tyr Trp Gly Gln Gly Thr Gln Val Thr
            100                 105                 110

Val Ser Ser
        115
```

GENETICALLY ENCODED FLUORESCENT-IRON FERRITIN NANOPARTICLE PROBES FOR DETECTING AN INTRACELLULAR TARGET BY FLUORESCENT AND ELECTRON MICROSCOPY

CROSS REFERENCE TO RELATED APPLICATIONS

This application is a continuation of PCT Application No. PCT/US2018/065533, filed on Dec. 13, 2018, which claims priority to U.S. Provisional Application No. 62/598,937, filed Dec. 14, 2017, both of which are incorporated herein by reference in their entirety.

ACKNOWLEDGMENT OF GOVERNMENT SUPPORT

This invention was made with government support under Grant No. 5U01 EB021247 awarded by the National Institutes of Health. The government has certain rights in the invention.

FIELD

This disclosure relates to embodiments of probes for labeling an intracellular target and methods of their use.

BACKGROUND

Fluorescent microscopy and electron microscopy (EM) each have limitations. While fluorescence microscopy is effective for multiple target labeling, ultrastructure cannot be revealed using fluorescence microscopy to the extent that it can be revealed with EM. However, sample fixation and target labeling for EM is complicated, and difficult to combine with sample fixation and target labeling for fluorescence microscopy.

SUMMARY

This disclosure provides novel genetically encoded probes for expression in cells to label an intracellular target (e.g., protein or DNA) for detection by both light microscopy (e.g., fluorescence) and EM. The probes are termed fluorescent-iron EM ferritin nanoparticle (FIREnano) probes and are comprised of an assembly of fusion proteins. The fusion proteins comprise a targeting domain that specifically binds to the intracellular target, a detection tag that can be used to detect the intracellular location of the probe using light (e.g., fluorescence) microscopy, and a mammalian (e.g., horse) ferritin heavy chain subunit. The ferritin subunit in the fusion protein self-assembles in mammalian cells to form a globular multi-subunit ferritin nanoparticle containing a cavity in which ferrous iron is oxidized to ferric oxide and stored. When assembled, the targeting domains and the detection tags extend radially outward from the exterior surface of the globular ferritin nanoparticle. The detection tag can be used to identify the intracellular location of the probe by light microscopy, and the ferric oxide in the globular ferritin nanoparticle can be used to detect the intracellular location of the probe by EM.

In several embodiments, the disclosed probes can be used for dynamic live cell imaging, super-resolution microscopy, and EM ultrastructure.

In some embodiments, a nucleic acid molecule is provided that encodes a fusion protein of a disclosed FIREnano probe. In some embodiments, the nucleic acid encodes a fusion protein comprising, in an N- to C-terminal direction, a targeting domain that specifically binds to an intracellular target antigen, a detection tag, and a horse ferritin heavy chain subunit. The horse ferritin heavy chain subunit in the fusion protein self-assembles in mammalian cells to form a globular ferritin nanoparticle that oxidizes ferrous iron to ferric oxide. The targeting domains specifically bind to the intracellular target antigen, and location of the fusion protein in the cell can be detected by both light microscopy (for detection of the detection tag) and EM (for detection of the ferric oxide in the ferritin nanoparticle).

In some embodiments, the intracellular target antigen is a protein (such as chromatin) or a nucleic acid molecule (such as RNA or DNA). In some embodiments, the targeting domain is one of an MS2 stem loop binding protein, a lambda N22 RNA binding protein, a PP7 RNA stem loop coat protein, an anti-suntag scFv, an anti-GFP single-chain antibody, PUFa, PUFb, FRB, FKBP, or dSpCas9. In some embodiments, the detection tag is one of a fluorescent protein or a fluorescent dye binding protein.

In some embodiments, the fusion protein further comprises a nuclear localization sequence N-terminal to the targeting domain The presence of the nuclear localization sequence on the fusion protein increases localization of the fusion protein in the cell nucleus.

Nucleic acid molecules encoding the disclosed fusion proteins are also provided, as are expression vectors including the nucleic acid molecules. Further provided are methods of detecting the location of a target antigen in a cell, comprising expressing a nucleic acid molecule encoding a FIREnano probe as described herein, and detecting the location of the detection tag and the ferritin nanoparticle on the probe in the host cell using fluorescence microscopy and EM, respectively, to detect the location of the target antigen in the cell.

The foregoing and other features and advantages of this disclosure will become more apparent from the following detailed description of several embodiments which proceeds with reference to the accompanying figures.

BRIEF DESCRIPTION OF THE FIGURES

FIGS. 1A-1C. Engineering genetically encoded FIREnano probes to label and visualize the chromatin ultrastructure of genes. (FIG. 1A) Illustration of an embodiment of the FIREnano probe subunit protein structure, from N- to C-terminus. (FIG. 1B) Schematic model showing genetically encoded ferritin nanoparticles that label green-fluorescent protein (GFP)-tagged loci in cells for light microscopy (e.g., fluorescence) and EM. The illustrated probe embodiment contains an N-terminal αGFP camelid antibody ($V_HH$) that binds to GFP tagged loci in cells, a fluorescent protein (e.g., mCherry) that can be detected by fluorescence microscopy, and a self-assembled globular ferritin nanoparticle. Ferritin self-assembles into a 24mer 12 nm iron binding particle. Iron salt is added into the cell culture media to load the ferritin nanoparticle with iron to make it visible by EM. (FIG. 1C) Work flow showing how to locate a FIREnano-labeled intracellular locus. Fluorescent signal (e.g., mCherry) from a FIREnano probe is collected to show that the probe labeled the GFP-tagged genomic locus successfully. A transmission electron microscopy (TEM) image of the same cell was also collected. The light and EM measurements were correlated to align images and locate the target region.

(FIG. 3A) Confocal images of DAPI, GFP, and mCherry showing successful labeling of the TRF1-GFP locus by the $\alpha$GFPV$_H$H-mCherry-*E. coli* Ferritin. (FIG. 3B) Correlated light (left) and TEM (middle) images with high magnification TEM shown for the boxed region. Arrows highlight areas of colocalized GFP and mCherry signal.

FIGS. 4A-4E. TEM of LacI-GFP tagged LacO repeat sequences labeled by $\alpha$GFPV$_H$H-mCherry-*E. coli* ferritin. (FIGS. 4A-4C) Confocal images of GFP, mCherry, and DAPI, showing successful labeling of GFP locus by $\alpha$GFPV$_H$H-mCherry-Ferritin. (FIG. 4D) Correlated light and EM was performed. (FIG. 4E): High magnification TEM images was taken at indicated box region. Arrows highlight areas of colocalized GFP and mCherry signal.

FIGS. 5A-5E. TEM of CX43-GFP tagged gap junction which are labeled by $\alpha$GFPV$_H$H-mCherry-*E. coli* ferritin. Confocal images of GFP (FIG. 5A), mCherry (FIG. 5B), and DAPI (FIG. 5C), showing successful labeling of the LacI-GFP locus by $\alpha$GFPV$_H$H-mCherry-Ferritin. (FIGS. 5D and 5E): Correlated light and EM with high magnification TEM images shown for the boxed region.

(FIG. 7A) Ferritin sequences from five species including heavy and light from human and horse, was human codon optimized and cloned into constructs with an N terminal FLAG tag. (FIG. 7B) Work flow showing how to purify FIREnano particles from mammalian cells using anti-FLAG dynal beads. (FIG. 7C) Left: Denature gel, anti-FLAG western blot is performed to detect the expression level of FLAG-ferritin. $\beta$-actin signal was used as loading control. Right: Native PAGE and silver staining of purified ferritin indicating *E. coli* ferritin is primarily monomeric (28 kDa, lane 1). *P. furiosus* ferritin and *H. pylori* ferritin partially assemble into particles, while all mammalian ferritin (horse and human) assembled into globular nanoparticle structures (lanes 4, 5, 6, and 7) with no detectable monomer, with horse ferritin heavy chain showing the greatest level of assembly.

(FIG. 8A) Four FIREnano probes (1-4) are depicted. These probes were expressed in mammalian cells and detected by mCherry fluorescence or Halotag labeling to show that they do not aggregate in cells (lower images). (FIG. 8B) Left: Denaturing gel, anti-FLAG western blot is performed to detect the expression level of the FIREnano probes. $\beta$-actin signal was used as a loading control. Middle: Native PAGE and silver staining of purified FIREnano probes showing that they all assemble into particles (lanes 1-4 correspond to probes 1-4, respectively), with pure apoferritin and ferritin as controls. Right: Native PAGE, prussian blue and 3,3'-Diaminobenzidine (DAB) staining showing the relative amount of Ferric iron loaded inside each ferritin under normal cell culture condition, with commercial pure apoferritin and ferritin as negative and positive control.

(FIG. 10A) TEM of commercial purchased horse spleen ferritin after 2% uranyl acetate (UA) staining, no staining, or 1% osmium staining. (FIG. 10B) TEM of purified FLAG-NLS-$\alpha$GFPV$_H$H-horse ferritin followed the same staining procedure. Arrow heads indicate iron core of ferritin particles. (FIG. 10C) Cryo-EM of the same sample. Arrow heads indicate iron loaded ferritin particles. Arrows indicate empty ferritin particles.

FIGS. 11A-11D. Fluorescence and EM imaging of $\alpha$GFPV$_H$H-mCherry-horse ferritin labeled ORF3-GFP fibers. U2OS cells expressing ORF3-GFP were transfected with plasmid encoding $\alpha$GFPV$_H$H-mCherry-ferritin and the cells were cultured with 500 $\mu$M FAC to iron-load the FIREnano probe. (FIGS. 11A-11C) confocal images of GFP (ORF3-GFP), mCherry ($\alpha$GFPV$_H$H-mCherry-ferritin), and DRAQ5 are shown. Arrows highlight areas of colocalized GFP and mCherry signal. (FIG. 11D) Correlated TEM image of the arrow region in 11A-11C. High magnification images is shown in boxed inset.

FIGS. 13A-13D. EM Tomography imaging of ORF3-GFP fibers labeled with the $\alpha$GFPV$_H$H-mCherry-ferritin FIREnano probe. U2OS cells expressing ORF3-GFP were transfected with plasmid encoding $\alpha$GFPV$_H$H-mCherry-ferritin and the cells were cultured with 500 $\mu$M FAC to iron-load the resulting FIREnano probe. (FIGS. 13A-13C) confocal images of GFP (ORF3-GFP), mCherry ($\alpha$GFPV$_H$H-mCherry-ferritin), and DRAQ5 signal are shown. Arrows highlight areas of colocalized GFP and mCherry signal. (FIG. 13D) Correlated EM tomography images of the arrow region in 13A-13C. Images of 40 serial 1 nm thick sections were projected and shown.

Figures 14A, 14B:
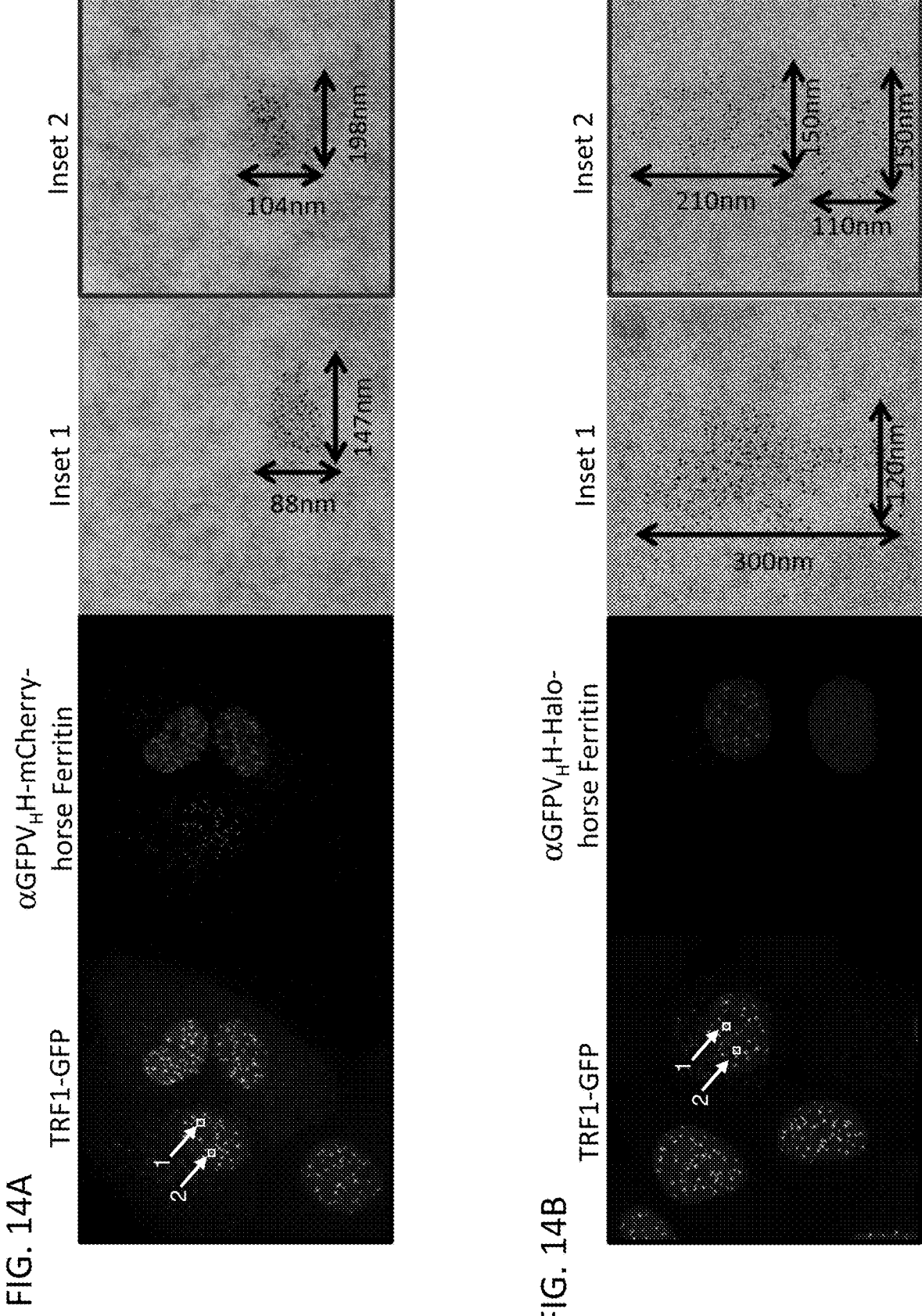
FIGS. 14A and 14B. TEM of TRF1-GFP telomere region labeled by $\alpha$GFPV$_H$H-Halo-ferritin and $\alpha$GFPV$_H$H-mCherry-ferritin. TRF1-GFP Hela cells were transfected with plasmid encoding $\alpha$GFPV$_H$H-mCherry-ferritin (FIG.

14A), or αGFPV$_H$H-Halo-ferritin (FIG. 14B) and the cells were cultured with 500 μM FAC to iron-load the resulting FIREnano probes. Confocal images of GFP and mCherry signal (FIG. 14A) or GFP and halo tag signal (FIG. 14B) are shown. After performing correlated light and EM, TEM images were taken from two spots of each cell. Diameter of individual telomere as indicated by ferritin labels was measured and shown.

FIGS. 15A-15E. Combination of ferritin labeling and ChromEM. Hela cells expressing TRF1-GFP were transfected with plasmid encoding αGFPV$_H$H-mCherry-ferritin and the cells were cultured with 500 μM FAC to iron-load the resulting FIREnano probe. (FIGS. 15A-15C) confocal images of GFP (TRF1-GFP), mCherry (αGFPV$_H$H-mCherry-ferritin), and DRAQ5 signal are shown. (FIGS. 15D and 15E) Transmitted light images of pre and post-DRAQ5 photo-oxidation. Arrows highlight areas of colocalized GFP and mCherry signal.

Figure 16:
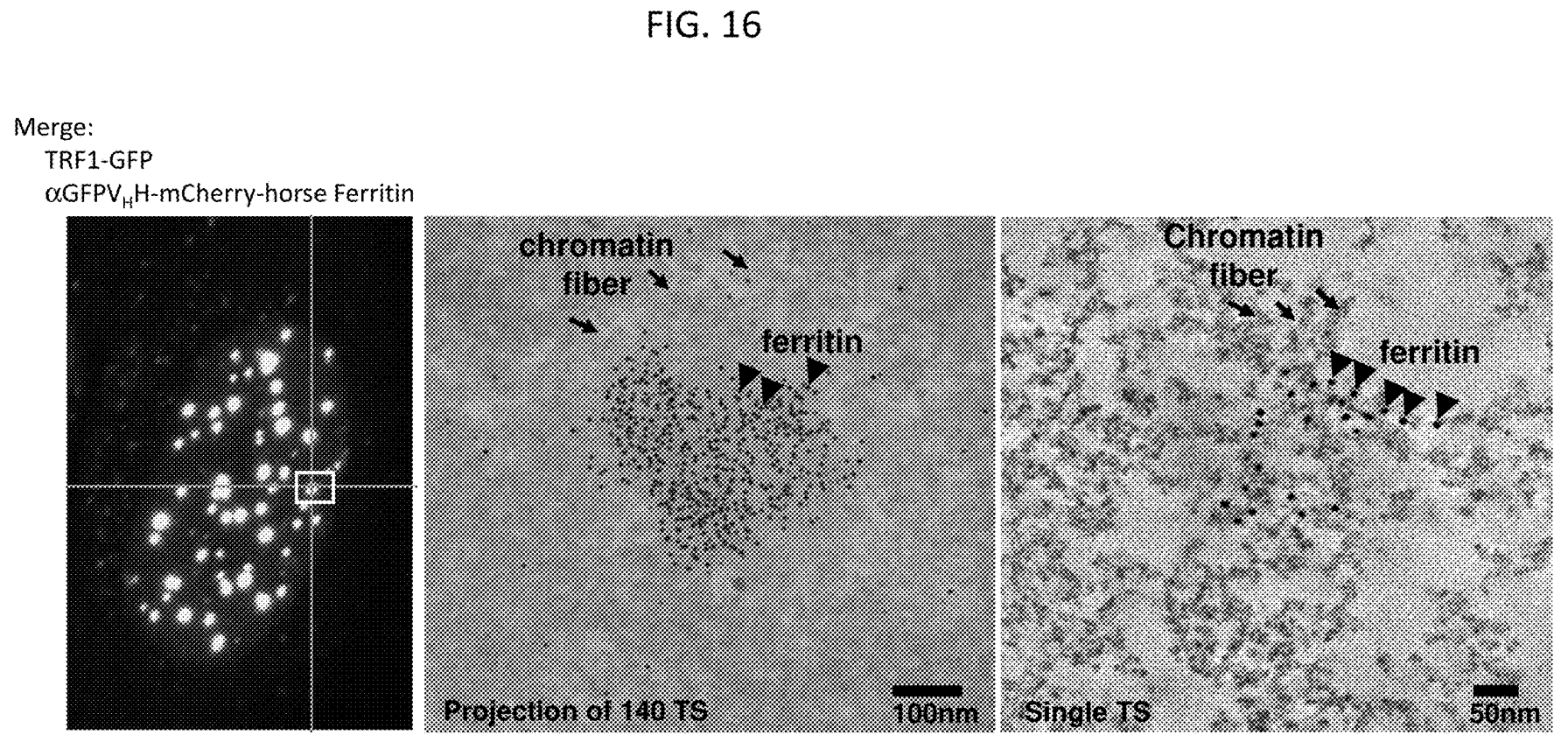

FIG. 16. ChromEMT (EM tomogram) of αGFPV$_H$H-mCherry-ferritin labeled telomere region with chromatin labeled through DRAQ5 photo-oxidation. Hela cells expressing TRF1-GFP were transfected with plasmid encoding αGFPV$_H$H-mCherry-ferritin and the cells were cultured with 500 μM FAC to iron-load the resulting FIREnano probe. Left: Selection of a telomere for subsequent electron tomography. Middle: Projection of ~140 tomogram slices showing both iron core from ferritin particles (arrow heads) and also chromatin fibers (arrows). Right: A single tomographic slice (1 nm thickness) showing ultrastructure of telomere chromatin labels with ferritin particles (dark spots, arrow heads).

Figures 17A, 17B, 17C, 17D:
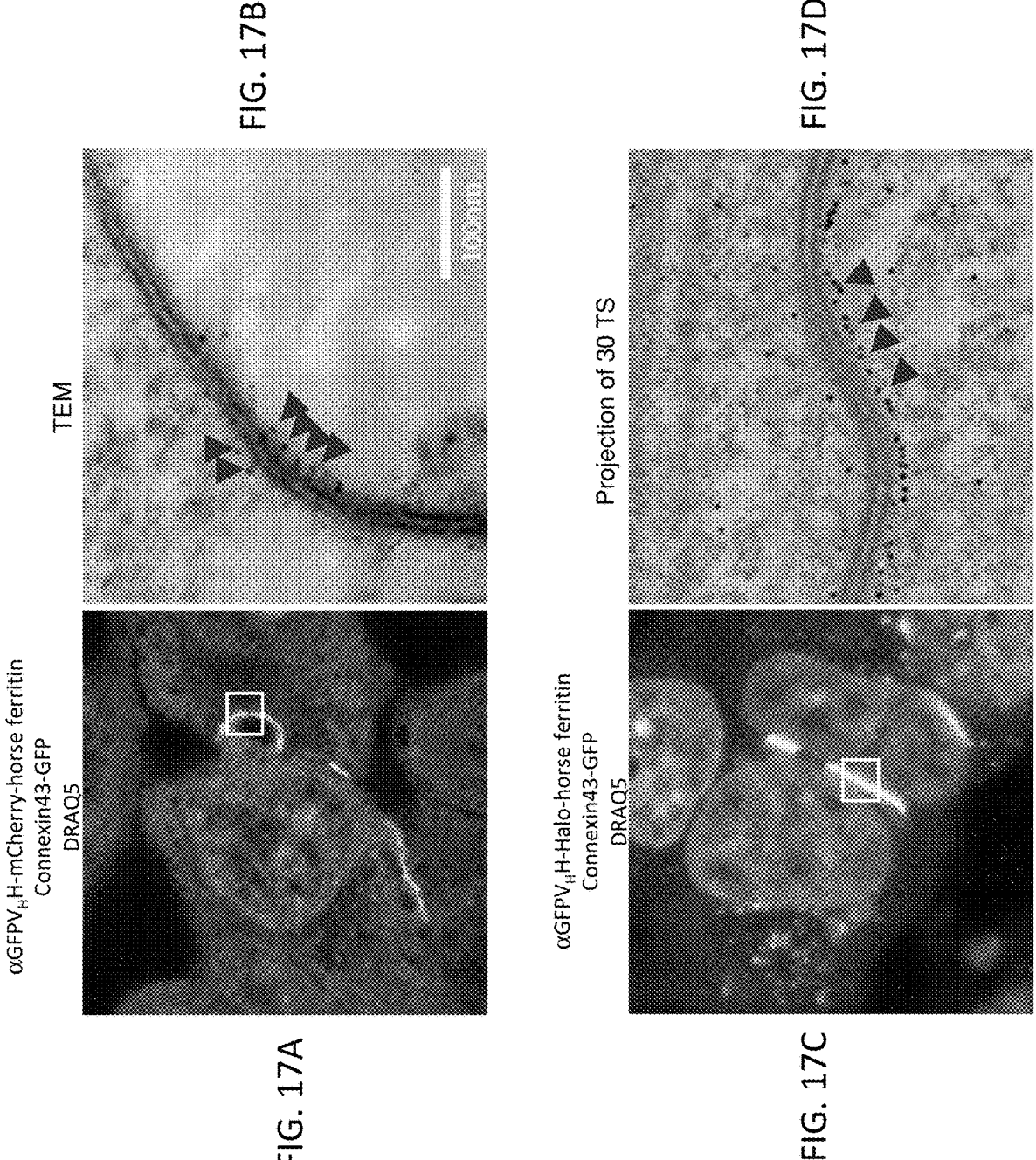

FIGS. 17A-17D. TEM and EMT imaging of ferritin labeled Cx43-GFP gap junction. U2OS cells expressing connexin43(CX43)-GFP were transfected with plasmid encoding αGFPV$_H$H-mCherry-horse ferritin and the cells were cultured with 500 μM FAC to iron-load the resulting FIREnano probe. (FIG. 17A) Confocal images of gap junction structure with CX43-GFP and αGFPV$_H$H-mCherry-ferritin, staining overlapped. (FIG. 17B) TEM of αGFPV$_H$H-mCherry-ferritin labeled CX43-GFP gap junction; the boxed area of FIG. 17A is shown. (FIG. 17C) Confocal images of gap junction structure region are collected. Connexin43-GFP, αGFPV$_H$H-Halo-ferritin, DAPI are overlapped. (FIG. 17D) 4 tilt EMT was performed on αGFPV$_H$H-Halo-horse ferritin labeled Cx43-GFP gap junction. 30 tomogram slices were projected together; the boxed area of FIG. 17C is shown. Arrows indicate individual ferritin particles.

Figure 18A:
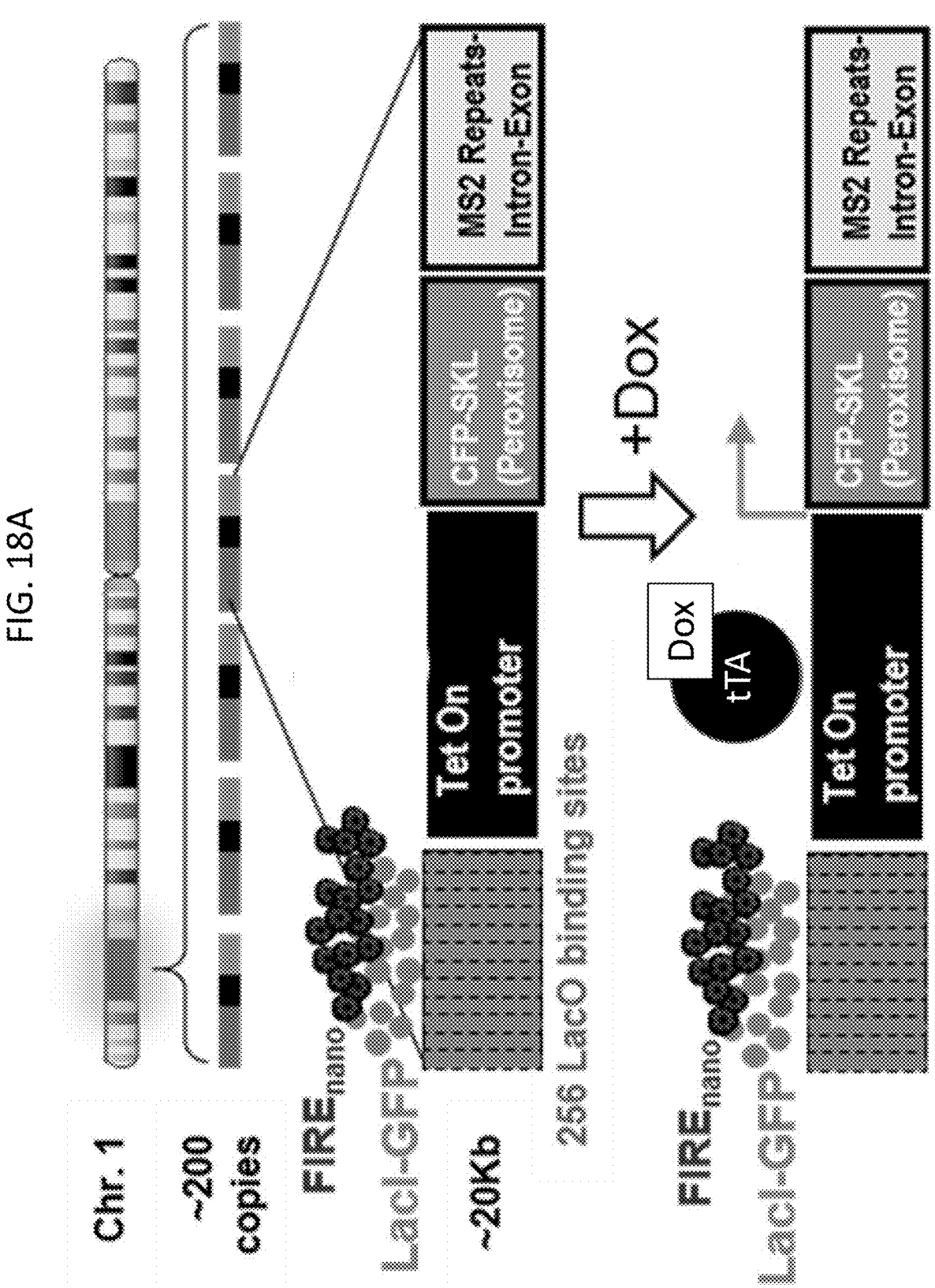
Figure 18B:
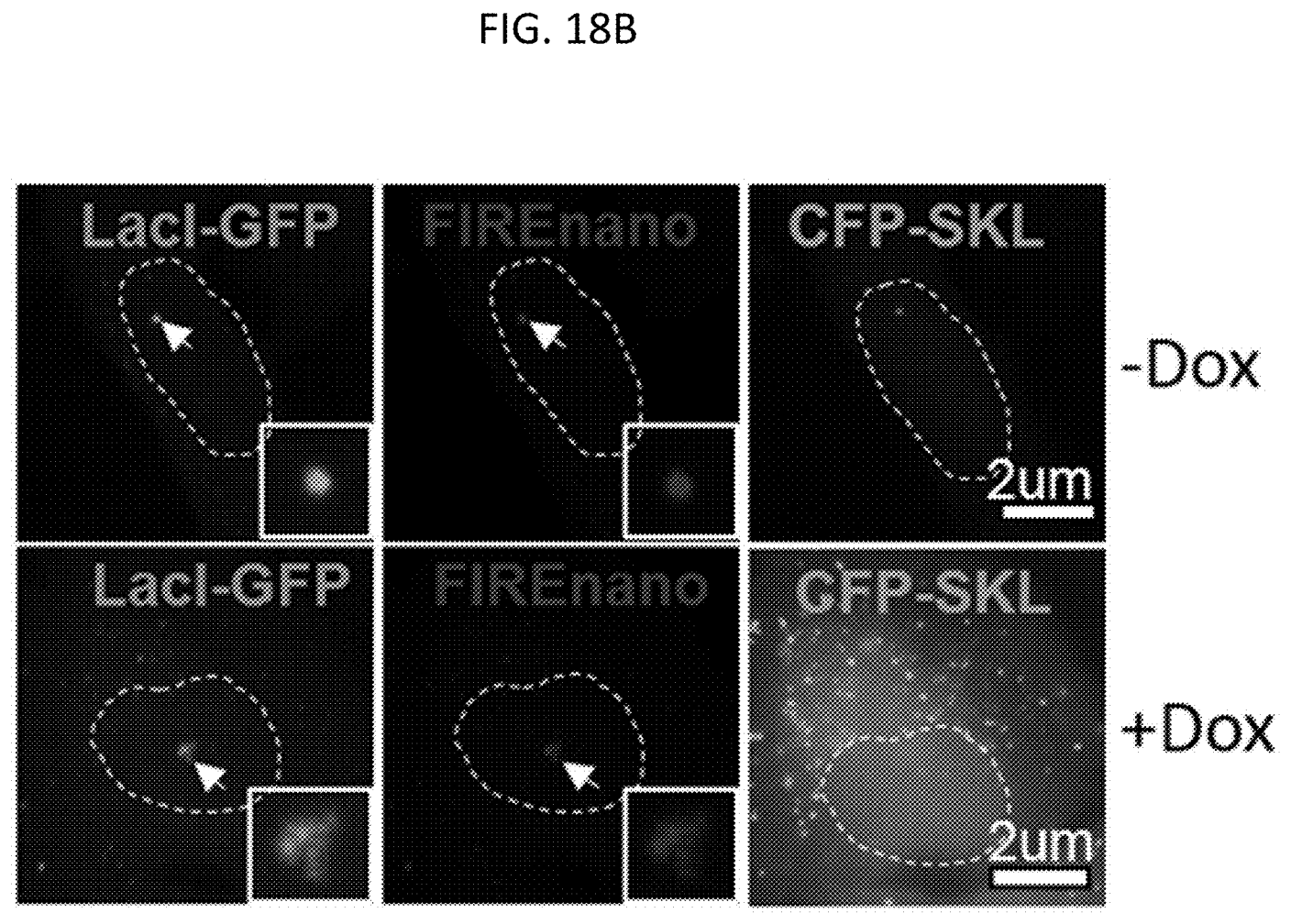
Figures 19A, 19B, 19C:
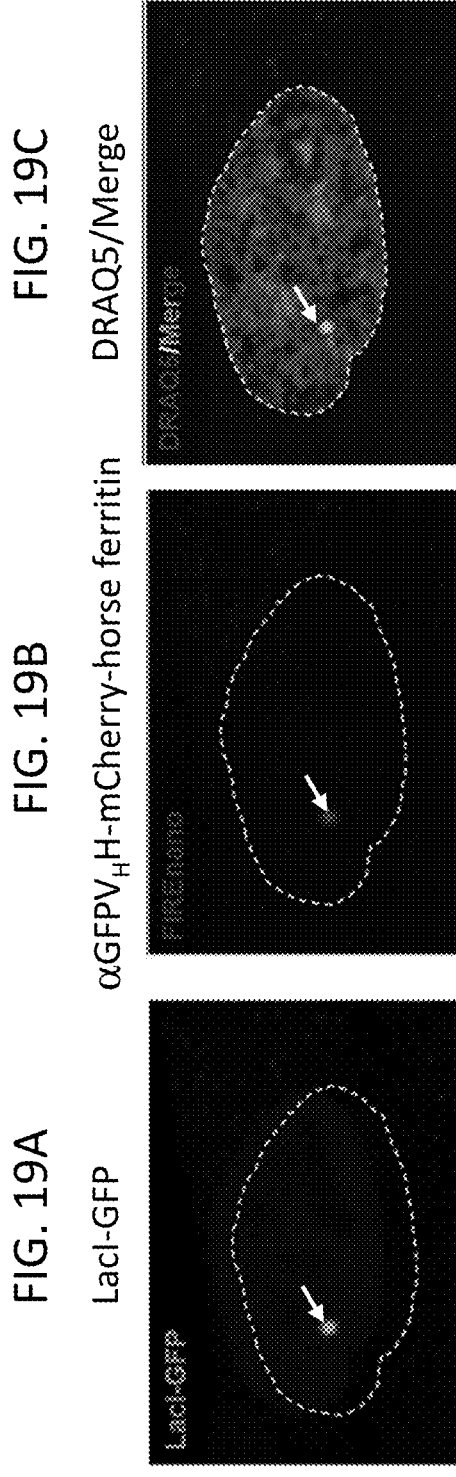
Figures 19D, 19E, 19F:
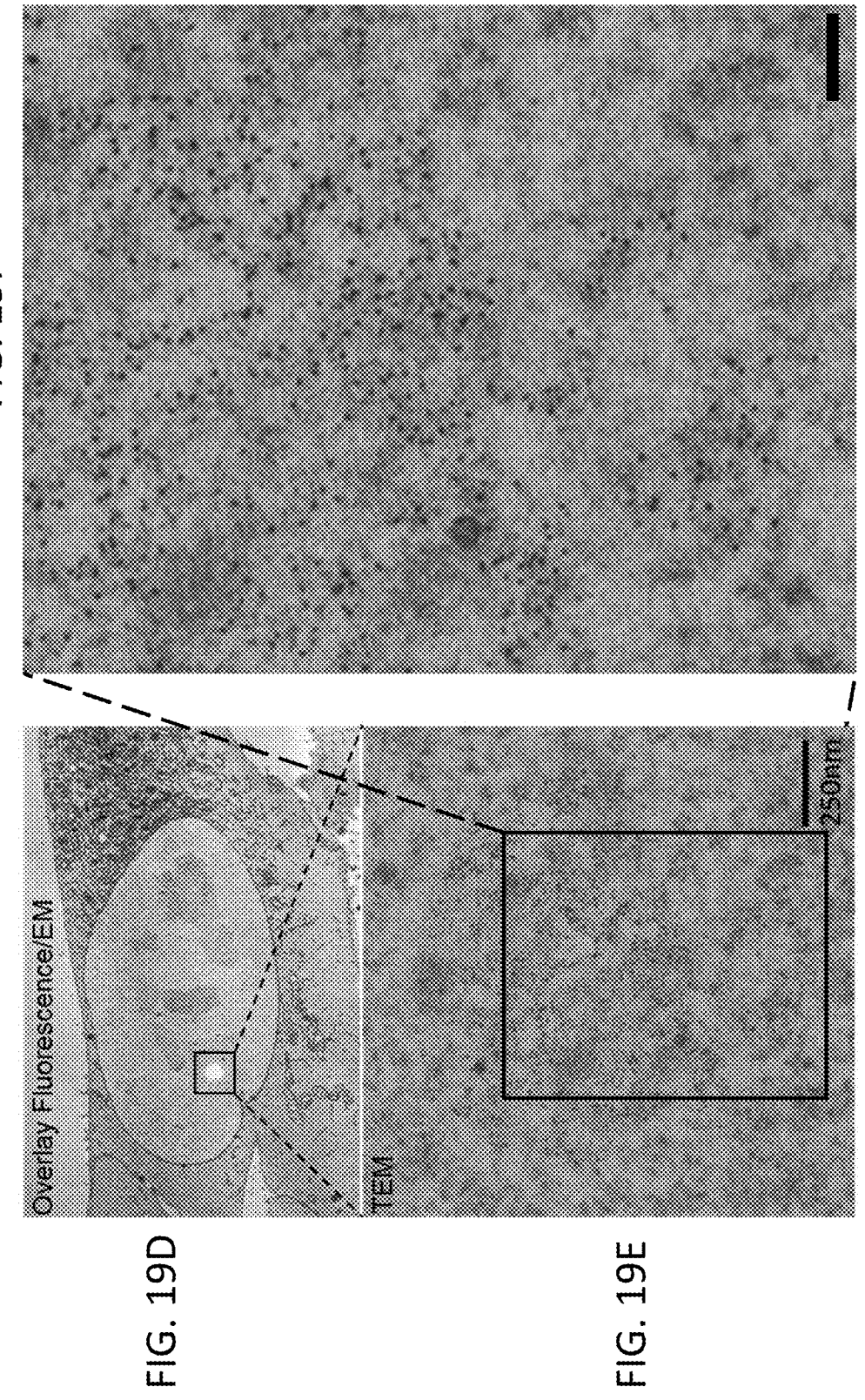
Figures 21A, 21B, 21C, 21D, 21E:
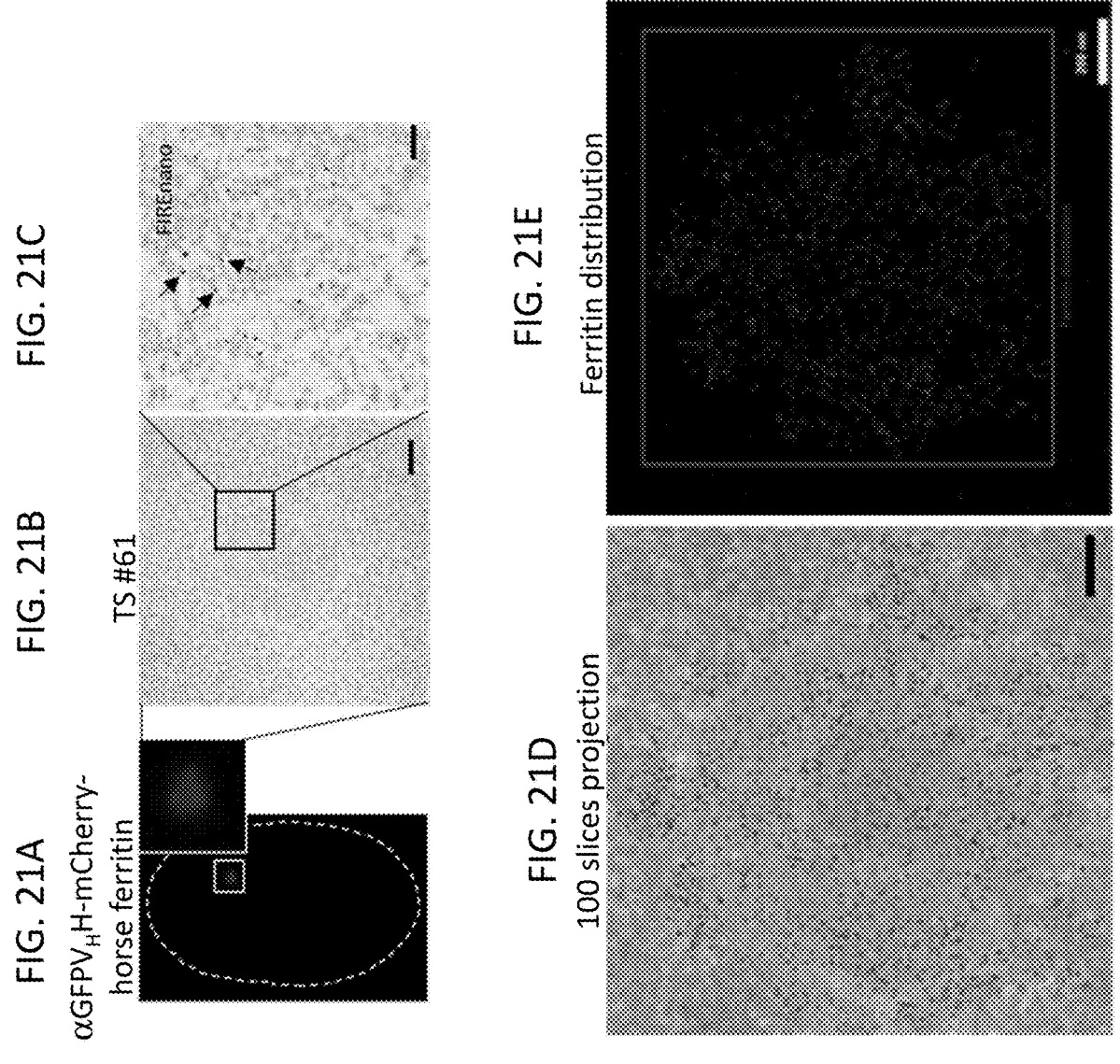
Figures 22A, 22B, 22C, 22D, 22E:
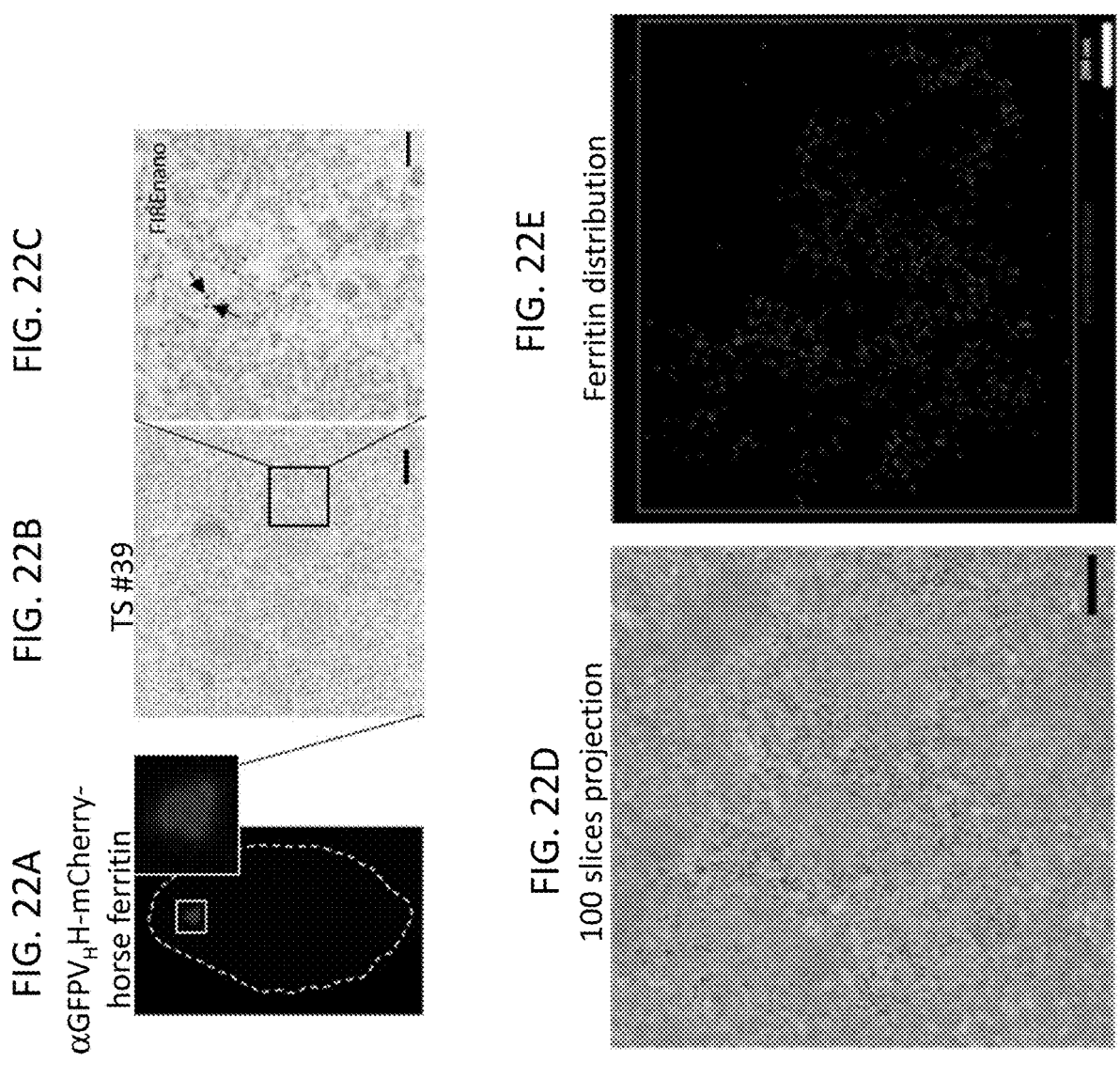

FIGS. 18A and 18B. Overview of U2OS cell line containing LacO and Tet On promoter genomic insert in Chromosome 1. (FIG. 18A) Schematic representation of the genomic insert. About 4 Mb sequences containing 200 gene arrays are artificially incorporated into chromosome 1 in the U2OS cell line. In each gene array, there are about 256 lacO binding sites, 96 Tet On promoter repeats, a mini CMV promoter, a CFP-SKL reporter which will locate in peroxisome in cytoplasm, and 24 MS2 stem loops, intron and exon. The CFP-SKL expression can be induced by adding doxycycline to the cell culture media. As depicted in the schematic, the FIREnano probe (e.g., αGFPV$_H$H-Halo-horse ferritin) can be applied to label LacI-GFP which binds to LacO sequences in both silent (without doxycycline, "−Dox") and active (with doxycycline, "+Dox") state. (FIG. 18B) The modified cell line was transfected with αGFPV$_H$H-mCherry-ferritin encoding plasmid. Confocal images are collected to show αGFPV$_H$H-Halo-horse ferritin can successfully label LacI-GFP in both silent (upper) and active (bottom) state. The CFP signal was collected by wide-field fluorescent microscope.

FIGS. 19A-19F. TEM of LacI-GFP tagged LacO repeat sequences labeled with αGFPV$_H$H-mCherry-horse ferritin. The modified cell line described in FIG. 18 was transfected with plasmid encoding αGFPV$_H$H-mCherry-ferritin and the cells were cultured with 500 μM FAC to iron-load the resulting FIREnano probe. Confocal images show GFP (FIG. 19A) and mCherry (FIG. 19B) signal. (FIG. 19C) The DRAQ5 signal is shown merged with the images from FIG. 19A and FIG. 19B. (FIG. 19D) Correlated light and EM. (FIG. 19E) TEM image showing ferritin nanoparticles (dark spots). (FIG. 19F) High magnification of box region in FIG. 19E.

FIGS. 20A and 20B. The FIREnano probe labels Lad GFP-tagged LacO sequences with and without the presence of doxycycline. The modified cell line described in FIG. 18 was transfected with plasmid encoding αGFPV$_H$H-mCherry-ferritin and the cells were cultured with 500 μM FAC to iron-load the resulting FIREnano probe. Doxycycline was added (FIG. 20B) or not (FIG. 20A) to the cell culture media. Confocal images of GFP and mCherry are shown, as are TEM and Correlated light and EM images. Arrows highlight areas of colocalized GFP and mCherry signal.

FIGS. 21A-21E. EM tomography was performed on the region of FIREnano labeled LacO sequences in the silent state. The modified cell line described in FIG. 18 was transfected with plasmid encoding αGFPV$_H$H-mCherry-ferritin and the cells were cultured with 500 μM FAC to iron-load the resulting FIREnano probe. The cells were cultured without the presence of doxycycline. (FIG. 21A) Confocal image showing fluorescent (mCherry) signal from FIREnano probes. (FIG. 21B) Image of one single tomogram slice (#61). (FIG. 21C) High magnification images of the boxed region in FIG. 21B, with FIREnano labels indicated by arrow. (FIG. 21D) Images from 100 tomography slices were projected to show the general distribution of FIREnano probes. (FIG. 21E) The FIREnano label is segmented and 3D distribution was displayed. The FIREnano distribution under silent state indicate LacO array formed a compact sphere structure.

FIGS. 22A-22E. EM tomography was performed on the region of FIREnano labeled LacO sequences in the silent state. The modified cell line described in FIG. 18 was transfected with plasmid encoding αGFPV$_H$H-mCherry-ferritin and the cells were cultured with 500 μM FAC to iron-load the resulting FIREnano probe. The cells were cultured with the presence of doxycycline. (FIG. 22A) Confocal image showing fluorescent (mCherry) signal from FIREnano probes. (FIG. 22B) Image of one single tomogram slice (#39). (FIG. 22C) High magnification images of the boxed region in FIG. 21B, with FIREnano labels indicated by arrow. (FIG. 22D) Images from 100 tomography slices were projected to show the general distribution of FIREnano probes. (FIG. 22E) FIREnano labels is segmented and 3D distribution was displayed. The FIREnano distribution under active state indicate LacO array occupy a bigger area than in silent state and is a more open structure.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~30 kb), which was created on Jun. 8, 2020, which is incorporated by reference herein. In the accompanying sequence listing:

SEQ ID NO: 1 is an exemplary nucleotide sequence encoding NLS-αGFPV$_H$H-GS linker-mCherry-GS linker-*E. coli* ferritin.
atgcccaaaaagaagaggaaagtgggatcgggtatggcagatgttcaattggtagaaagtggtggagcactcgtaca gcctggtggttctcttcgactgtcatgcgcagcttcaggatttccagtgaatagatatagtatgagatggtatagac aagcccctggaaaagaaagagagtgggtggccggaatgtcctcagccggagatagaagtagttatgaagatagtgtt aaaggacgatttacaatttcaagagatgatgcaagaaatacagtttacctccaaatgaatagtcttaaacctgaaga tacagcagtttattattgtaatgttaacgtgggattcgaatactggggtcagggaacacaagtaacggtaagtagcg gttcaggctggagccacccgcagttcgaaaaaggatccgggcatcaccatcatcaccacggatccgggcccaagaaa aagcgcaaggtaatggtgagcaagggcgaggaggataacatggccatcatcaaggagttcatgcgcttcaaggtgca catggagggctccgtgaacggccacgagttcgagatcgagggcgagggcgagggccgcccctacgagggcacccaga ccgccaagctgaaggtgaccaagggtggccccctgcccttcgcctgggacatcctgtcccctcagttcatgtacggc tccaaggcctacgtgaagcacccccgccgacatccccgactacttgaagctgtccttccccgagggcttcaagtggga gcgcgtgatgaacttcgaggacggcggcgtggtgaccgtgacccaggactcctccctgcaggacggcgagttcatct acaaggtgaagctgcgcggcaccaacttcccctccgacggccccgtaatgcagaagaagaccatgggctgggaggcc tcctccgagcggatgtaccccgaggacggcgccctgaagggcgagatcaagcagaggctgaagctgaaggacggcgg ccactacgacgctgaggtcaagaccacctacaaggccaagaagcccgtgcagctgcccggcgcctacaacgtcaaca tcaagttggacatcacctcccacaacgaggactacaccatcgtggaacagtacgaacgcgccgagggccgccactcc accggcggcatggacgagctgtacaagggatccggctcaggatctatgaagggcgacaccaaggtcatcaactacct gaacaagttgctggggaacgaactcgtggccatcaaccagtacttcctgcacgcacgcatgttcaagaactggggcc tgaagcgcctgaacgatgtggagtaccacgagtccatcgacgagatgaagcacgccgatagatacatcgagcggatt ctgtttctggaaggacttccgaatttgcaagacctggggaagctgaatatcggagaggatgtggaggaaatgctgag aagcgacctcgcgctggaacttgatggtgccaagaacctcagggaagccattggatacgctgactcggtgcacgact acgtgtcacgggacatgatgatcgagatcctgcgcgacgaagaaggccacattgactggctcgaaactgagctggac ctgatccagaagatgggactccagaactatctgcaagcgcagattcgggaagagggttaa SEQ ID NO: 2 is an exemplary nucleotide sequence encoding FLAG-*E. coli* ferritin.
atggactacaaggaccacgatggtgattataaggatcatgatatagactataaggacgacgacgacaagggaggagg gtccggcggcggaagtggcggtggctcaatgttgaaacctgagatgattgagaaacttaatgaacagatgaatttgg aactttacagttccttgttgtatcagcaaatgagtgcttggtgcagctatcatacgtttgagggtgcggcagcgttc ttgcggaggcatgcgcaggaggaaatgacccacatgcagagacttttttgattacctcactgataccggaaatcttcc tcgaatcaacacggtagaaagccctttcgccgaatatagtagcttggacgagctgtttcaagaaacgtacaaacacg agcagctcatcacacagaagataaatgagctggctcatgctgcaatgaccaatcaagactaccctacatttaacttt ctgcagtggtatgtgagtgaacaacacgaagaagagaaactgttcaaatctattattgataaacttagtctcgctgg taagtccggtgagggtttgtatttcatagacaaagaactctccactcttgatacccagaactaa SEQ ID NO: 3 is an exemplary nucleotide sequence encoding horse ferritin heavy chain.
atgactaccgcttttccctcccaagttaggcaaaattaccatcaagacagcgaagctgctatcaaccgccagatcaa tcttgagctccacgcttcctatgtctatctgtctatgtccttttattttgatagagatgacgtcgcactgaagaact tcgctaagtacttcctgcatcagagtcacgaggaaagggagcacgctgaaaagcttatgaaactgcaaaatcaacgg ggggggcgcatcttccttcaggatataaaaaagcctgaccaagatgactgggagaacggcctcaaggctatggaatg cgctctccatctggagaagaacgtaaatgagtctctttgctggagctgcacaagctggcgacagacaaaaatgacccgc -continued atttgtgtgatttcctggaaactcattatcttaatgaacaagtgaaggctattaaagaattgggcgatcatgtaacg aacctgagaaggatgggggcacctgaatcagggatggccgaatatctgttcgataagcatacattgggtgagtgtga cgaatcttga SEQ ID NO: 4 is an exemplary nucleotide sequence encoding FLAG-*helicobacter* ferritin.
atggactataaggaccatgatggcgattatataaagaccatgacattgattataaggacgacgacgataagggcggcgg cagcgggggggggctccggcggtggctctatgttgagtaaagacatcataaaactcctgaatgagcaggtaaacaaag agatgcagtcaagcaacctctacatgtcaatgtcctcttggtgttacacacattctctggatggggcgggcttgttc cttttcgaccacgcagcggaagagtatgagcacgcaaagaaactgattattttttctcaacgagaataacgtgccggt tcagcttacctcaatcagcgcccccgagcacaaattcgagggcttgactcaaatcttccaaaaagcgtatgagcacg agcaacacataagtgaatccattaacaacatagtggaccacgctattaagtccaaagatcacgcaacctttaatttc ctgcagtggtatgttgccgaacaacatgaggaagaggttctttttaaagatatactggataagatagaactcatcgg gaacgaaaatcatgggttgtacctcgctgatcagtacgtaaaaggaatagctaaatcaagaaaaagttga SEQ ID NO: 5 is an exemplary nucleotide sequence encoding FLAG-human ferritin heavy chain.
atggattacaaggaccatgacgggggattatataaggaccatgatattgactataaagacgacgatgataaaggaggcgg cagtggtggtggtagtggcggtggatccatgtcttcacaaatacgacaaaactactccaccgatgtgagaggcggcgg tcaatagcctggttaatttgtatctgcaagcatcatatacgtacctgtccctgggtttttacttcgatagggacgat gttgccctggaaggtgttagccattttttccgcgagttggcagaagaaaaaggggagggttacgagaggcttctgaa aatgcagaatcagcggggtggtagagctttgtttcaagatataaaaaagcctgccgaggacgaatggggcaagactc ctgatgccatgaaggcggccatggccttggaaaaaaagttgaaccaggcactcctcgatctgcatgctctcggcagc gcccggacggaccccccacttgtgtgacttttttggaaacacattttctggacgaggaagtgaagctcattaaaaaat gggggaccacttgactaatctgcaccgccttgggggtccagaagccggattgggcgaatatcttttgagagactca ccttgaagcatgattga SEQ ID NO: 6 is an exemplary nucleotide sequence encoding FLAG-NLS-
αGFPV$_H$H-GS linker-horse ferritin heavy chain.
atggactacaaggaccacgatggcgattatataaagatcacgacatagattacaaagatgatgatgataagcctaagaa gaagcgaaaagttggcatggcggatgttcagctcgtagagtctggcggcgcactggtgcaacccggtggctccctgc gcttgagctgtgctgcttcaggattttcccgtgaacagatattccatgcgctggtatcggcaggctcctggaaaagag cgagagtgggtcgcagggatgtcctccgccggtgataggagctcatacgaagacagcgttaagggacgctttacaat ctctcgagatgacgcccgcaataccgtctacctgcagatgaacagtcttaagcctgaggataccgcagtttattatt gtaacgtgaatgtcggttttgagtactgggggcagggcacgcaggtgacagtttcttccggcggcggtagtggaggc ggatcaggggggcggtagcatgacaaccgcttttcccagtcaggttcggcaaaactaccatcaggacagcgaagcagc gatcaatcgacaaattaacctcgagctccatgctagctacgtttacttgagtatgtccttctattttgatcgcgacg atgttgcgttgaaaaatttcgctaagtatttcttgcaccagtcacatgaggaacgcgagcatgcggaaaagttgatg aagctgcaaaaccagcgaggcgggcgcattttccttcaagacatcaaaaagccagatcaggatgattgggagaacgg ccttaaggcaatggagtgtgcgctccaccttgaaaagaatgtcaacgaatccctgctcgaactccataagctggcga ccgacaaaaatgatcctcacctttgcgatttttctggagacacattatctgaatgagcaagtgaaagcaataaaggag ttgggtgatcatgtcacaaaccttagacggatgggggcaccagaatccggaatggcagaatacttgtttgataagca tacgctgggtgagtgtgatgaatcttag SEQ ID NO: 7 is an exemplary nucleotide sequence encoding FLAG-NLS-
αGFPV$_H$H-GS linker-mCherry-GS linker-horse ferritin heavy chain.
atggattacaaagatcacgacggagattataaggatcacgatatcgattataaagacgatgatgacaaacccaaaaa aaagcgcaaagttggtatggcggatgtgcagttggttgagtctggcggggcactcgtgcagccgggggggtagtctga gattgagttgtgccgcctccggattttccagtcaacagatattcaatgcgctggtatcgacaggcgccagggaaagag -continued agagaatgggttgcgggtatgtcatcagcgggtgatcgatcctcttacgaggattcagtgaaagggcggtttacaat aagccgagatgacgccagaaatacggtatacctccagatgaactccctcaagccggaagatacggcagtttactatt gtaacgttaatgttggatttgagtattggggccaaggaacgcaagtgaccgtcagcagtggtggtggaagtggcgga gggtcaggaggcggatctatggttagcaagggcgaggaggataatatggccattatcaaagaattcatgcgctttaa ggtccacatggagggtagtgtcaacggtcatgaatttgagatagagggtgaagggggaaggtaggccttacgagggta ctcaaactgcgaaattgaaagtcacaaagggggtcccctcccttttgcgtgggatatactctccccacaatttatg tacggttcaaaagcctatgttaagcaccctgcggacatccccgactacctgaaactcagttttcctgaaggcttcaa gtgggagcgggtcatgaattttgaggacggtggggtcgtaacggtcactcaggactcatctcttcaagatggtgagt ttatctataaagtaaagttgcgcggtactaactttccgtccgacggaccagtaatgcaaaaaaaaacaatgggttgg gaggcttcatccgaacggatgtatcccgaagacggggctctcaagggtgagattaaacaaaggcttaaactgaagga tggaggccattacgatgctgaagttaaaaccacgtataaagcgaagaaacccgttcagctgcctggtgcatataatg tgaatatcaaattggatataaacctcacacaatgaggactatactatcgtagaacaatatgaacgggcggaaggacga cactcaaccggggggaatggatgaactttataaaggggggaggaagcggggggagggtctgggggtggttcaggcggggg atcaggtggcgggagtatgactactgcattcccgagccaagtgcggcagaattaccaccaggactctgaagcggcca tcaaccgacaaatcaacctggaactgcatgcgtcttacgtttatctgtcaatgagctttttactttgatagagacgat gtcgcattgaagaacttcgccaaatattttcttcatcagagccatgaggaaagggaacatgcagaaaaacttatgaa attgcagaaccagcgcggtggaaggattttcctccaagacataaagaaaccggatcaggacgactgggagaatggcc tgaaggcaatggaatgtgcacttcacctcgaaaagaacgtgaacgagagcctcctggaactgcataaattggccact gacaaaaacgatccacacctgtgcgatttccttgagactcattatcttaacgagcaagtgaaagcaattaaagagtt gggtgatcatgtcactaacctgagacgcatgggggcaccagaaagcggcatggcagagtatttgtttgacaagcata cacttggtgagtgtgacgagtcttga SEQ ID NO: 8 is an exemplary nucleotide sequence encoding FLAG-NLS-
αGFPV$_H$H-GS linker-halo tag-GS linker-horse ferritin heavy chain.
atggattacaaagatcacgacggagattataaggatcacgatatcgattataaagacgatgatgacaaacccaaaaa aaagcgcaaagttggtatggcggatgtgcagttggttgagtctggcggggcactcgtgcagccggggggtagtctga gattgagttgtgccgcctccggatttccagtcaacagatattcaatgcgctggtatcgacaggcgccagggaaagag agagaatgggttgcgggtatgtcatcagcgggtgatcgatcctcttacgaggattcagtgaaagggcggtttacaat aagccgagatgacgccagaaatacggtatacctccagatgaactccctcaagccggaagatacggcagtttactatt gtaacgttaatgttggatttgagtattggggccaaggaacgcaagtgaccgtcagcagtggtggtggaagtggcgga gggtcaggaggcggatctgaaatcggtactggctttccattcgaccccattatgtggaagtcctgggcgagcgcat gcactacgtcgatgttggtccgcgcgatggcacccctgtgctgttcctgcacggtaacccgacctcctcctacgtgt ggcgcaacatcatcccgcatgttgcaccgacccatcgctgcattgctccagacctgatcggtatgggcaaatccgac aaaccagacctgggttatttcttcgacgaccacgtccgcttcatggatgccttcatcgaagccctgggtctggaaga ggtcgtcctggtcattcacgactggggctccgctctgggtttccactgggccaagcgcaatccagagcgcgtcaaag gtattgcatttatggagttcatccgccctatcccgacctgggacgaatggccagaatttgcccgcgagaccttccag gccttccgcaccaccgacgtcggccgcaagctgatcatcgatcagaacgtttttatcgagggtacgctgccgatggg tgtcgtccgcccgctgactgaagtcgagatggaccattaccgcgagccgttcctgaatcctgttgaccgcgagccac tgtggcgcttcccaaacgagctgccaatcgccggtgagccagcgaacatcgtcgcgctggtcgaagaatacatggac tggctgcaccagtcccctgtcccgaagctgctgttctggggcaccccaggcgttctgatcccaccggccgaagccgc tcgcctggccaaaagcctgcctaactgcaaggctgtggacatcggcccgggtctgaatctgctgcaagaagacaacc cggacctgatcggcagcgagatcgcgcgctggctgtccacgctcgagatttccggcggggggaggaggcagcggggga gggggttctggggggtggtggatcaggcggggggaggctcaggtggcgggggaagtatgactactgcattcccgagcca agtgcggcagaattaccaccaggactctgaagcggccatcaaccgacaaatcaacctggaactgcatgcgtcttacg tttatctgtcaatgagcttttactttgatagagacgatgtcgcattgaagaacttcgccaaatattttcttcatcag agccatgaggaaagggaacatgcagaaaaacttatgaaattgcagaaccagcgcggtggaaggattttcctccaaga cataaagaaaccggatcaggacgactgggagaatggcctgaaggcaatggaatgtgcacttcacctcgaaaagaacg tgaacgagagcctcctggaactgcataaattggccactgacaaaaacgatccacacctgtgcgatttccttgagact cattatcttaacgagcaagtgaaagcaattaaagagttgggtgatcatgtcactaacctgagacgcatgggggcacc agaaagcggcatggcagagtatttgtttgacaagcatacacttggtgagtgtgacgagtcttga SEQ ID NO: 9 is an exemplary nucleotide sequence encoding MS2 stem loop
binding protein (MCP).
atggcttctaactttactcagttcgttctcgtcgacaatggcggaactggcgacgtgactgtcgccccaagcaactt cgctaacgggatcgctgaatggatcagctctaactcgcgttcacaggcttacaaagtaacctgtagcgttcgtcaga gctctgcgcagaatcgcaaatacaccatcaaagtcgaggtgcctaaaggcgcctggcgttcgtacttaaatatggaa ctaaccattccaattttcgccacgaattccgactgcgagcttattgttaaggcaatgcaaggtctcctaaaagatgg aaacccgattccctcagcaatcgcagcaaactccggcatctac SEQ ID NO: 10 is an exemplary nucleotide sequence encoding lambda N22
RNA binding protein (N22p).
atgggtaatgctcggacccggcgaagagagaggcgggctgagaagcaggcacagtggaaggctgcaaac SEQ ID NO: 11 is an exemplary nucleotide sequence encoding PP7 RNA stem
loop coat protein (PCP).
atgggttccaaaaccatcgttctttcggtcggcgaggctactcgcactctgactgagatccagtccaccgcagaccg tcagatcttcgaagagaaggtcgggcctctggtgggtcggctgcgcctcacggcttcgctccgtcaaaacggagcca agaccgcgtatcgcgtcaacctaaaactggatcaggcggacgtcgttgattccggacttccgaaagtgcgctacact caggtatggtcgcacgacgtgacaatcgttgcgaatagcaccgaggcctcgcgcaaatcgttgtacgatttgaccaa gtccctcgtcgcgacctcgcaggtcgaagatcttgtcgtcaaccttgtgccgctgggccgt SEQ ID NO: 12 is an exemplary nucleotide sequence encoding anti-suntag
scFv.
atgggtccagacatagtgatgacgcagagtccgtctagtctctcagcttctgtcggcgaccgggttactattacatg ccgctccagcactggagcagtgacaacgtctaactacgcttcatgggttcaagaaaagccaggaaaactcttcaaag gcctgattggtgggaccaacaatcgagcacccggtgttcctagccggttttctggcagcctcataggagataaagcg acgctgactatatcaagtttgcaacctgaggatttcgccacatacttctgcgccctttggtattccaaccactgggt cttcggacaaggcactaaggtggaactgaagagaggcggtggcggctccggcggtggtggctccggggggcggcgggt ccagcggtggtgggagcgaagtaaagttgctcgaatccggggggaggactcgtgcaacccggaggatcattgaaactg tcctgcgcggtgtcaggattctcactcacagactacggagtaaattgggttcgccaagctccgggccggggtctgga atggatcggcgtgatctggggcgatggtatcaccgactataactctgcactcaaagataggtttatcatttccaaag acaatgggaagaacacggtatacctgcagatgtctaaggtgagaagcgatgacacagcgttgtattattgtgtgact gggcttttgattattggggtcagggcacactcgtgactgtctccagc SEQ ID NO: 13 is an exemplary nucleotide sequence encoding anti-mCherry
V$_H$H.
atggctcaagttcagcttgtcgagagcggcggcagtttggttcaacctggaggtagtcttcggctctcttgcgcggc tagtgggcggtttgcggagtcttctagtatggggtggtttcggcaggccccaggcaaagaacgcgagtttgttgcag cgattagttggagtggtggggcgacgaattatgcagatagcgcaaagggccgatttacgcttagccgggacaacact aagaacaccgtttacttgcaaatgaactcattgaaaccggacgatacagcggtttattactgcgcggccaacttggg gaactatatatcaagcaaccagaggctctacggttactggggccaagggacgcaagttacagtatctagccctttca cg -continued SEQ ID NO: 14 is an exemplary nucleotide sequence encoding PUFa.
tctagaggccgcagccgccttttggaagattttcgaaacaaccggtaccccaatttacaactgcgggagattgctgg acatataatggaattttcccaagaccagcatgggtccagattcattcagctgaaactggagcgtgccacaccagctg agcgccagcttgtcttcaatgaaatcctccaggctgcctaccaactcatggtggatgtgtttggtaattacgtcatt cagaagttctttgaatttggcagtcttgaacagaagctggctttggcagaacggattcgaggccacgtcctgtcatt ggcactacagatgtatggcagccgtgttatcgagaaagctcttgagtttattccttcagaccagcagaatgagatgg ttcgggaactagatggccatgtcttgaagtgtgtgaaagatcagaatggcaatcacgtggttcagaaatgcattgaa tgtgtacagccccagtctttgcaatttatcatcgatgcgtttaagggacaggtatttgccttatccacacatcctta tggctgccgagtgattcagagaatcctggagcactgtctccctgaccagacactccctattttagaggagcttcacc agcacacagagcagctggtacaggatcaatatggaaattatgtaatccaacatgtactggagcacggtcgtcctgag gataaaagcaaaattgtagcagaaatccgaggcaatgtacttgtattgagtcagcacaaatttgcaagcaatgttgt ggagaagtgtgttactcacgcctcacgtacggagcgcgctgtgctcatcgacgaggtgtgcaccatgaacgacggtc cccacagtgccttatacaccatgatgaaggaccagtatgccaactacgtggtccagaagatgattgacgtggcggag ccaggccagcggaagatcgtcatgcataagatccggccccacatcgcaactcttcgtaagtacacctatggcaagca cattctggccaagctggagaagtactacatgaagaacggtgttgacttaggggggccggcc SEQ ID NO: 15 is an exemplary nucleotide sequence encoding PUFb.
tctagaggccgcagccgccttttggaagattttcgaaacaaccggtaccccaatttacaactgcgggagattgctgg acatataatggaattttcccaagaccagcatgggtccagattcattcagctgaaactggagcgtgccacaccagctg agcgccagcttgtcttcaatgaaatcctccaggctgcctaccaactcatggtggatgtgtttggtaattacgtcatt cagaagttctttgaatttggcagtcttgaacagaagctggctttggcagaacggattcgaggccacgtcctgtcatt ggcactacagatgtatggctgccgtgttatccagaaagctcttgagtttattccttcagaccagcagaatgagatgg ttcgggaactagatggccatgtcttgaagtgtgtgaaagatcagaatggcaatcacgtggttcagaaatgcattgaa tgtgtacagccccagtctttgcaatttatcatcgatgcgtttaagggacaggtatttgccttatccacacatcctta tggctgccgagtgattcagagaatcctggagcactgtctccctgaccagacactccctattttagaggagcttcacc agcacacagagcagctggtacaggatcaatatggaagttatgtaatcgaacatgtactggagcacggtcgtcctgag gataaaagcaaaattgtagcagaaatccgaggcaatgtacttgtattgagtcagcacaaatttgcaaacaatgttgt gcagaagtgtgttactcacgcctcacgtacggagcgcgctgtgctcatcgatgaggtgtgcaccatgaacgacggtc cccacagtgccttatacaccatgatgaaggaccagtatgccaactacgtggtccagaagatgattgacgtggcggag ccaggccagcggaagatcgtcatgcataagatccggccccacatcgcaactcttcgtaagtacacctatggcaagca cattctggccaagctggagaagtactacatgaagaacggtgttgacttaggggggccggcc SEQ ID NO: 16 is an exemplary nucleotide sequence encoding FRB.
gagatgtggcatgaaggcctagaagaggcctctcgcttgtactttggggagaggaacgtcaaaggcatgtttgaggt gctggagcccctgcatgctatgatggaacgcggtccccagaccctgaaggaaacgtcctttaatcaggcatatggtc gagatttaatggaggcacaagaatggtgccgaaagtacatgaaatcagggaacgtcaaggacctcctccaagcctgg gacctctactatcacgtgttcagacgaatctcaaagcag SEQ ID NO: 17 is an exemplary nucleotide sequence encoding FKBP.
ggagtgcaggtggaaaccatctccccaggagacgggcgcaccttccccaagcgcggccagacctgcgtggtgcacta caccgggatgcttgaagatggaaagaaatttgattcctcccgggacagaaacaagcccctttaagtttatgctaggca agcaggaggtgatccgaggctgggaagaagggggttgcccagatgagtgtgggtcagagagccaaactgactatatct ccagattatgcctatggtgccactgggcacccaggcatcatcccaccacatgccactctcgtcttcgatgtggagct tctaaaactg -continued SEQ ID NO: 18 is an exemplary nucleotide sequence encoding dSpCas9.
gacaagaagtactccattgggctcgctatcggtaccaacagcgtcggctgggccgtcattacggacgagtacaaggt gccgagcaaaaaattcaaagttctgggcaataccgatcgccacagcataaagaagaacctcattggagccctcctgt tcgactccggggagacggccgaagccacgcggctcaaaagaacagcacggcgcagatatacccgcagaaagaatcgg atctgctacctgcaggagatctttagtaatgagatggctaaggtggatgactctttcttccataggctggaggagtc cttttttggtggaggaggataaaaagcacgagcgccacccaatctttggcaatatcgtggacgaggtggcgtaccatg aaaagtacccaaccatatatcatctgaggaagaagctggtagacagtactgataaggctgacttgcggttgatctat ctcgcgctggcgcacatgatcaaatttcggggacacttcctcatcgaggggggacctgaacccagacaacagcgatgt cgacaaactctttatccaactggttcagacttacaatcagcttttcgaggagaacccgatcaacgcatccggcgttg acgccaaagcaatcctgagcgctaggctgtccaaatcccggcggctcgaaaacctcatcgcacagctccctggggag aagaagaacggcctgtttggtaatcttatcgccctgtcactcgggctgacccccaactttaaatctaacttcgacct ggccgaagatgccaagctgcaactgagcaaagacacctacgatgatgatctcgacaatctgctggcccagatcggcg accagtacgcagacctttttttggcggcaaagaacctgtcagacgccattctgctgagtgatattctgcgagtgaac acggagatcaccaaagctccgctgagcgctagtatgatcaagcgctatgatgagcaccaccaagacttgactttgct gaaggcccttgtcagacagcaactgcctgagaagtacaaggaaattttcttcgatcagtctaaaaatggctacgccg gatacattgacggcggagcaagccaggaggaattttacaaatttattaagcccatcttggaaaaaatggacggcacc gaggagctgctggtaaagctgaacagagaagatctgttgcgcaaacagcgcactttcgacaatggaagcatcccccca ccagattcacctgggcgaactgcacgctatcctcaggcggcaagaggatttctaccccttttttgaaagataacaggg aaaagattgagaaaatcctcacatttcggataccctactatgtaggcccccctcgctcggggaaattccagattcgcg tggatgactcgcaaatcagaagagaccatcactccctggaacttcgaggaagtcgtggataaggggggcctctgccca gtccttcatcgaaaggatgactaactttgataaaaatctgcctaacgaaaaggtgcttcctaaacactctctgctgt acgagtacttcacagtttataacgagctcaccaaggtcaaatacgtcacagaagggatgagaaagccagcattcctg tctggagagcagaagaaagctatcgtggacctcctcttcaagacgaaccggaaagttaccgtgaaacagctcaaaga agactatttcaaaaagattgaatgtttcgactctgttgaaatcagcggagtggaggatcgcttcaacgcatccctgg gaacgtatcacgatctcctgaaaatcattaaagacaaggacttcctggacaatgaggagaacgaggacattcttgag gacattgtcctcacccttacgttgtttgaagatagggagatgattgaagaacgcttgaaaacttacgctcatctctt cgacgacaaagtcatgaaacagctcaagagacgccgatatacaggatggggggcggctgtcaagaaaactgatcaatg gcatccgagacaagcagagtggaaagacaatcctggattttcttaagtccgatggatttgccaaccggaacttcatg cagttgatccatgatgactctctcaccttttaaggaggacatccagaaagcacaagtttctggccaggggggacagtct tcacgagcacatcgctaatcttgcaggtagcccagctatcaaaaagggaatactgcagaccgttaaggtcgtggatg aactcgtcaaagtaatgggaaggcataagcccgagaatatcgttatcgagatggcccgagagaaccaaactacccag aagggacagaagaacagtagggaaaggatgaagaggattgaagagggtataaaagaactggggtcccaaatccttaa ggaacacccagttgaaaacacccagcttcagaatgagaagctctacctgtactacctgcagaacggcagggacatgt acgtggatcaggaactggacatcaaccggttgtccgactacgacgtggatgctatcgtgcccaaagctttctcaaa gatgattctattgataataaagtgttgacaagatccgataaaaatagagggaagagtgataacgtcccctcagaaga agttgtcaagaaaatgaaaaattattggcggcagctgctgaacgccaaactgatcacacaacggaagttcgataatc tgactaaggctgaacgaggtggcctgtctgagttggataaagccggcttcatcaaaaggcagcttgttgagacacgc cagatcaccaagcacgtggcccaaattctcgattcacgcatgaacaccaagtacgatgaaaatgacaaactgattcg agaggtgaaagttattactctgaagtctaagctggtctcagatttcagaaaggactttcagttttataaggtgagag agatcaacaattaccaccatgcgcatgatgcctacctgaatgcagtggtaggcactgcacttatcaaaaaatatccc aagctggaatctgaatttgtttacggagactataaagtgtacgatgttaggaaaatgatcgcaaagtctgagcagga -continued aataggcaaggccaccgctaagtacttcttttacagcaatattatgaattttttcaagaccgagattacactggcca atggagagattcggaagcgaccacttatcgaaacaaacggagaaacaggagaaatcgtgtgggacaagggtagggat ttcgcgacagtccgcaaggtcctgtccatgccgcaggtgaacatcgttaaaaagaccgaagtacagaccggaggctt ctccaaggaaagtatcctcccgaaaaggaacagcgacaagctgatcgcacgcaaaaaagattgggaccccaagaaat acggcggattcgattctcctacagtcgcttacagtgtactggttgtggccaaagtggagaaagggaagtctaaaaaa ctcaaaagcgtcaaggaactgctgggcatcacaatcatggagcgatccagcttcgagaaaaaccccatcgactttct cgaagcgaaaggatataaagaggtcaaaaaagacctcatcattaagctgcccaagtactctctctttgagcttgaaa acggccggaaacgaatgctcgctagtgcgggcgagctgcagaaaggtaacgagctggcactgccctctaaatacgtt aatttcttgtatctggccagccactatgaaaagctcaaagggtctcccgaagataatgagcagaagcagctgttcgt ggaacaacacaaacactaccttgatgagatcatcgagcaaataagcgagttctccaaaagagtgatcctcgccgacg ctaacctcgataaggtgctttctgcttacaataagcacagggataagcccatcagggagcaggcagaaaacattatc cacttgtttactctgaccaacttgggcgcgcctgcagccttcaagtacttcgacaccaccatagacagaaagcggta cacctctacaaaggaggtcctggacgccacactgattcatcagtcaattacggggctctatgaaacaagaatcgacc tctctcagctcggtggagac SEQ ID NO: 19 is the amino acid sequence of NLS-αGFPV<sub>H</sub>H-GS linker-
mCherry-GS linker-*E.coli* ferritin.
MPKKKRKVGSGMADVQLVESGGALVQPGGSLRLSCAASGFPVNRYSMRWYRQAPGKEREWVAGMSSAGDRSSYEDSV

KGRFTISRDDARNTVYLQMNSLKPEDTAVYYCNVNVGFEYWGQGTQVTVSSGSGWSHPQFEKGSGHHHHHHGSGPKK

KRKVMVSKGEEDNMAIIKEFMRFKVHMEGSVNGHEFEIEGEGEGRPYEGTQTAKLKVTKGGPLPFAWDILSPQFMYG

SKAYVKHPADIPDYLKLSEPEGFKWERVMNFEDGGVVTVTQDSSLQDGEFIYKVKLRGTNFPSDGPVMQKKTMGWEA

SSERMYPEDGALKGEIKQRLKLKDGGHYDAEVKTTYKAKKPVQLPGAYNVNIKLDITSHNEDYTIVEQYERAEGRHS

TGGMDELYKGSGSGSMKGDTKVINYLNKLLGNELVAINQYFLHARMFKNWGLKRLNDVEYHESIDEMKHADRYIERI

LFLEGLPNLQDLGKLNIGEDVEEMLRSDLALELDGAKNLREAIGYADSVHDYVSRDMMIEILRDEEGHIDWLETELD

LIQKMGLQNYLQAQIREEG

SEQ ID NO: 20 is the amino acid sequence of FLAG-*E.coli* ferritin.
MDYKDHDGDYKDHDIDYKDDDDKGGGSGGGSGGGSMLKPEMIEKLNEQMNLELYSSLLYQQMSAWCSYHTFEGAAAF

LRRHAQEEMTHMQRLFDYLTDTGNLPRINTVESPFAEYSSLDELFQETYKHEQLITQKINELAHAAMTNQDYPTFNF

LQWYVSEQHEEEKLFKSIIDKLSLAGKSGEGLYFIDKELSTLDTQN

SEQ ID NO: 21 is the amino acid sequence of horse ferritin heavy chain.
MTTAFPSQVRQNYHQDSEAAINRQINLELHASYVYLSMSFYFDRDDVALKNFAKYFLHQSHEEREHAEKLMKLQNQR

GGRIFLQDIKKPDQDDWENGLKAMECALHLEKNVNESLLELHKLATDKNDPHLCDFLETHYLNEQVKAIKELGDHVT

NLRRMGAPESGMAEYLFDKHTLGECDES

SEQ ID NO: 22 is the amino acid sequence of FLAG-*helicobacter* ferritin.
MDYKDHDGDYKDHDIDYKDDDDKGGGSGGGSGGGSMLSKDIIKLLNEQVNKEMQSSNLYMSMSSWCYTHSLDGAGLF

LFDHAAEEYEHAKKLIIFLNENNVPVQLTSISAPEHKFEGLTQIFQKAYEHEQHISESINNIVDHAIKSKDHATFNF

LQWYVAEQHEEEVLFKDILDKIELIGNENHGLYLADQYVKGIAKSRKS

SEQ ID NO: 23 is the amino acid sequence of FLAG-human ferritin heavy chain.
MDYKDHDGDYKDHDIDYKDDDDKGGGSGGGSGGGSMSSQIRQNYSTDVEAAVNSLVNLYLQASYTYLSLGFYFDRDD

VALEGVSHFFRELAEEKREGYERLLKMQNQRGGRALFQDIKKPAEDEWGKTPDAMKAAMALEKKLNQALLDLHALGS

ARTDPHLCDFLETHFLDEEVKLIKKMGDHLTNLHRLGGPEAGLGEYLFERLTLKHD

SEQ ID NO: 24 is the amino acid sequence of FLAG-NLS-αGFPV<sub>H</sub>H-GS
linker-horse ferritin heavy chain.
MDYKDHDGDYKDHDIDYKDDDDKPKKKRKVGMADVQLVESGGALVQPGGSLRLSCAASGFPVNRYSMRWYRQAPGKE

REWVAGMSSAGDRSSYEDSVKGRFTISRDDARNTVYLQMNSLKPEDTAVYYCNVNVGFEYWGQGTQVTVSSGGGSGG

-continued
GSGGGSMTTAFPSQVRQNYHQDSEAAINRQINLELHASYVYLSMSFYFDRDDVALKNFAKYFLHQSHEEREHAEKLM

KLQNQRGGRIFLQDIKKPDQDDWENGLKAMECALHLEKNVNESLLELHKLATDKNDPHLCDFLETHYLNEQVKAIKE

LGDHVTNLRRMGAPESGMAEYLFDKHTLGECDES

SEQ ID NO: 25 is the amino acid sequence of FLAG-NLS-αGFPV<sub>H</sub>H-GS
linker-mCherry-GS linker-horse ferritin heavy chain.
MDYKDHDGDYKDHDDYKDDDDKPKKKRKVGMADVQLVESGGALVQPGGSLRLSCAASGFPVNRYSMRWYRQAPGKE

REWVAGMSSAGDRSSYEDSVKGRFTISRDDARNTVYLQMNSLKPEDTAVYYCNVNVGFEYWGQGTQVTVSSGGGSGG

GSGGGSMVSKGEEDNMAIIKEFMRFKVHMEGSVNGHEFEIEGEGEGRPYEGTQTAKLKVTKGGPLPFAWDILSPQFM

YGSKAYVKHPADIPDYLKLSFPEGFKWERVMNFEDGGVVTVTQDSSLQDGEFIYKVKLRGTNFPSDGPVMQKKTMGW

EASSERMYPEDGALKGEIKQRLKLKDGGHYDAEVKTTYKAKKPVQLPGAYNVNIKLDITSHNEDYTIVEQYERAEGR

HSTGGMDELYKGGGSGGGSGGGSGGGSGGGSMTTAFPSQVRQNYHQDSEAAINRQINLELHASYVYLSMSFYFDRDD

VALKNFAKYFLHQSHEEREHAEKLMKLQNQRGGRIFLQDIKKPDQDDWENGLKAMECALHLEKNVNESLLELHKLAT

DKNDPHLCDFLETHYLNEQVKAIKELGDHVTNLRRMGAPESGMAEYLFDKHTLGECDES

SEQ ID NO: 26 is the amino acid sequence of FLAG-NLS-αGFPV<sub>H</sub>H-GS
linker-halo tag-GS linker-horse ferritin heavy chain.
MDYKDHDGDYKDHDIDYKDDDDKPKKKRKVGMADVQLVESGGALVQPGGSLRLSCAASGFPVNRYSMRWYRQAPGKE

REWVAGMSSAGDRSSYEDSVKGRFTISRDDARNTVYLQMNSLKPEDTAVYYCNVNVGFEYWGQGTQVTVSSGGGSGG

GSGGGSEIGTGFPFDPHYVEVLGERMHYVDVGPRDGTPVLFLHGNPTSSYVWRNIIPHVAPTHRCIAPDLIGMGKSD

KPDLGYFFDDHVRFMDAFIEALGLEEVVLVIHDWGSALGFHWAKRNPERVKGIAFMEFIRPIPTWDEWPEFARETFQ

AFRTTDVGRKLIIDQNVFIEGTLPMGVVRPLTEVEMDHYREPFLNPVDREPLWRFPNELPIAGEPANIVALVEEYMD

WLHQSPVPKLLFWGTPGVLIPPAEAARLAKSLPNCKAVDIGPGLNLLQEDNPDLIGSEIARWLSTLEISGGGGSGG

GGSGGGGSGGGGSGGGGSMTTAFPSQVRQNYHQDSEAAINRQINLELHASYVYLSMSFYFDRDDVALKNFAKYFLHQ

SHEEREHAEKLMKLQNQRGGRIFLQDIKKPDQDDWENGLKAMECALHLEKNVNESLLELHKLATDKNDPHLCDFLET

HYLNEQVKAIKELGDHVTNLRRMGAPESGMAEYLFDKHTLGECDES

SEQ ID NO: 27 is the amino acid sequence of MS2 binding protein (MCP).
MASNFTQFVLVDNGGTGDVTVAPSNFANGIAEWISSNSRSQAYKVTCSVRQSSAQNRKYTIKVEVPKGAWRSYLNME

LTIPIFATNSDCELIVKAMQGLLKDGNPIPSAIAANSGIY

SEQ ID NO: 28 is the amino acid sequence of lambda N22 RNA binding protein
(N22p).
MGNARTRRRERRAEKQAQWKAAN SEQ ID NO: 29 is the amino acid sequence of PP7 RNA stem loop coat protein
(PCP).
MGSKTIVLSVGEATRTLTEIQSTADRQIFEEKVGPLVGRLRLTASLRQNGAKTAYRVNLKLDQADVVDSGLPKVRYT

QVWSHDVTIVANSTEASRKSLYDLTKSLVATSQVEDLVVNLVPLGR

SEQ ID NO: 30 is the amino acid sequence of anti-suntag scFv.
MGPDIVMTQSPSSLSASVGDRVTITCRSSTGAVTTSNYASWVQEKPGKLFKGLIGGTNNRAPGVPSRFSGSLIGDKA

TLTISSLQPEDFATYFCALWYSNHWVFGQGTKVELKRGGGGSGGGGSGGGGSSGGGSEVKLLESGGGLVQPGGSLKL

SCAVSGFSLTDYGVNWVRQAPGRGLEWIGVIWGDGITDYNSALKDRFIISKDNGKNTVYLQMSKVRSDDTALYYCVT

GLFDYWGQGTLVTVSS

SEQ ID NO: 31 is the amino acid sequence of anti-mCherry V<sub>H</sub>H.
MAQVQLVESGGSLVQPGGSLRLSCAASGRFAESSSMGWFRQAPGKEREFVAAISWSGGATNYADSAKGRFTLSRDNT

KNTVYLQMNSLKPDDTAVYYCAANLGNYISSNQRLYGYWGQGTQVTVSSPFT

SEQ ID NO: 32 is the amino acid sequence of PUFa.
SRGRSRLLEDFRNNRYPNLQLREIAGHIMEFSQDQHGSRFIQLKLERATPAERQLVFNEILQAAYQLMVDVFGNYVI

QKFFEFGSLEQKLALAERIRGHVLSLALQMYGSRVIEKALEFIPSDQQNEMVRELDGHVLKCVKDQNGNHVVQKCIE

CVQPQSLQFIIDAFKGQVFALSTHPYGCRVIQRILEHCLPDQTLPILEELHQHTEQLVQDQYGNYVIQHVLEHGRPE

DKSKIVAEIRGNVLVLSQHKFASNVVEKCVTHASRTERAVLIDEVCTMNDGPHSALYTMMKDQYANYVVQKMIDVAE

PGQRKIVMHKIRPHIATLRKYTYGKHILAKLEKYYMKNGVDLGGPA

SEQ ID NO: 33 is the amino acid sequence of PUFb.
SRGRSRLLEDFRNNRYPNLQLREIAGHIMEFSQDQHGSRFIQLKLERATPAERQLVFNEILQAAYQLMVDVFGNYVI

QKFFEFGSLEQKLALAERIRGHVLSLALQMYGCRVIQKALEFIPSDQQNEMVRELDGHVLKCVKDQNGNHVVQKCIE

CVQPQSLQFIIDAFKGQVFALSTHPYGCRVIQRILEHCLPDQTLPILEELHQHTEQLVQDQYGSYVIEHVLEHGRPE

DKSKIVAEIRGNVLVLSQHKFANNVVQKCVTHASRTERAVLIDEVCTMNDGPHSALYTMMKDQYANYVVQKMIDVAE

PGQRKIVMHKIRPHIATLRKYTYGKHILAKLEKYYMKNGVDLGGPA

SEQ ID NO: 34 is the amino acid sequence of FRB.
EMWHEGLEEASRLYFGERNVKGMFEVLEPLHAMMERGPQTLKETSFNQAYGRDLMEAQEWCRKYMKSGNVKDLLQAW

DLYYHVFRRISKQ

SEQ ID NO: 35 is the amino acid sequence of FKBP.
GVQVETISPGDGRTFPKRGQTCVVHYTGMLEDGKKFDSSRDRNKPFKFMLGKQEVIRGWEEGVAQMSVGQRAKLTIS

PDYAYGATGHPGIIPPHATLVFDVELLKL

SEQ ID NO: 36 is the amino acid sequence of dSpCas9.
DKKYSIGLAIGTNSVGWAVITDEYKVPSKKFKVLGNTDRHSIKKNLIGALLFDSGETAEATRLKRTARRRYTRRKNR

ICYLQEIFSNEMAKVDDSFFHRLEESFLVEEDKKHERHPIFGNIVDEVAYHEKYPTIYHLRKKLVDSTDKADLRLIY

LALAHMIKFRGHFLIEGDLNPDNSDVDKLFIQLVQTYNQLFEENPINASGVDAKAILSARLSKSRRLENLIAQLPGE

KKNGLFGNLIALSLGLTPNFKSNFDLAEDAKLQLSKDTYDDDLDNLLAQIGDQYADLFLAAKNLSDAILLSDILRVN

TEITKAPLSASMIKRYDEHHQDLTLLKALVRQQLPEKYKEIFFDQSKNGYAGYIDGGASQEEFYKFIKPILEKMDGT

EELLVKLNREDLLRKQRTFDNGSIPHQIHLGELHAILRRQEDFYPFLKDNREKIEKILTFRIPYYVGPLARGNSRFA

WMTRKSEETITPWNFEEVVDKGASAQSFIERMTNFDKNLPNEKVLPKHSLLYEYFTVYNELTKVKYVTEGMRKPAFL

SGEQKKAIVDLLFKTNRKVTVKQLKEDYFKKIECFDSVEISGVEDRFNASLGTYHDLLKIIKDKDFLDNEENEDILE

DIVLTLTLFEDREMIEERLKTYAHLFDDKVMKQLKRRRYTGWGRLSRKLINGIRDKQSGKTILDFLKSDGFANRNFM

QLIHDDSLTFKEDIQKAQVSGQGDSLHEHIANLAGSPAIKKGILQTVKVVDELVKVMGRHKPENIVIEMARENQTTQ

KGQKNSRERMKRIEEGIKELGSQILKEHPVENTQLQNEKLYLYYLQNGRDMYVDQELDINRLSDYDVDAIVPQSFLK

DDSIDNKVLTRSDKNRGKSDNVPSEEVVKKMKNYWRQLLNAKLITQRKFDNLTKAERGGLSELDKAGFIKRQLVETR

QITKHVAQILDSRMNTKYDENDKLIREVKVITLKSKLVSDFRKDFQFYKVREINNYHHAHDAYLNAVVGTALIKKYP

KLESEFVYGDYKVYDVRKMIAKSEQEIGKATAKYFFYSNIMNFFKTEITLANGEIRKRPLIETNGETGEIVWDKGRD

FATVRKVLSMPQVNIVKKTEVQTGGFSKESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFELENGRKRMLASAGELQKGNELALPSKYV

NFLYLASHYEKLKGSPEDNEQKQLFVEQHKHYLDEIIEQISEFSKRVILADANLDKVLSAYNKHRDKPIREQAENII

HLFTLTNLGAPAAFKYFDTTIDRKRYTSTKEVLDATLIHQSITGLYETRIDLSQLGGD

SEQ ID NO: 37 is the amino acid sequence of a glycine-serine peptide linker.
GGGSGGGSGGGS SEQ ID NO: 38 is an exemplary nucleic acid sequence encoding a halo tag.
gaaatcggtactggctttccattcgacccccattatgtgtggaagtcctgggcgagcgcatgcactacgtcgatgttgg tccgcgcgatggcaccctgtgctgttcctgcacggtaacccgacctcctcctacgtgtggcgcaacatcatcccgc atgttgcaccgacccatcgctgcattgctccagacctgatcggtatgggcaaatccgacaaaccagacctgggttat ttcttcgacgaccacgtccgcttcatggatgccttcatcgaagccctgggtctggaagaggtcgtcctggtcattca cgactggggctccgctctgggtttccactgggccaagcgcaatccagagcgcgtcaaaggtattgcatttatggagt tcatccgccctatcccgacctgggacgaatggccagaatttgcccgcgagaccttccaggccttccgcaccaccgac gtcggccgcaagctgatcatcgatcagaacgttttttatcgagggtacgctgccgatgggtgtcgtccgcccgctgac -continued tgaagtcgagatggaccattaccgcgagccgttcctgaatcctgttgaccgcgagccactgtggcgcttcccaaacg agctgccaatcgccggtgagccagcgaacatcgtcgcgctggtcgaagaatacatggactggctgcaccagtcccct gtcccgaagctgctgttctggggcaccccaggcgttctgatcccaccggccgaagccgctcgcctggccaaaagcct gcctaactgcaaggctgtggacatcggcccgggtctgaatctgctgcaagaagacaacccggacctgatcggcagcg agatcgcgcgctggctgtccacgctcgagatttccggc SEQ ID NO: 39 is the amino acid sequence of a halotag.
EIGTGFPFDPHYVEVLGERMHYVDVGPRDGTPVLFLHGNPTSSYVWRNIIPHVAPTHRCIAPDLIGMGKSDKPDLGY

FFDDHVRFMDAFIEALGLEEVVLVIHDWGSALGFHWAKRNPERVKGIAFMEFIRPIPTWDEWPEFARETFQAFRTTD

VGRKLIIDQNVFIEGTLPMGVVRPLTEVEMDHYREPFLNPVDREPLWRFPNELPIAGEPANIVALVEEYMDWLHQSP

VPKLLFWGTPGVLIPPAEAARLAKSLPNCKAVDIGPGLNLLQEDNPDLIGSEIARWLSTLEISG

SEQ ID NO: 40 is an exemplary nucleic acid sequence encoding mCherry.
atggttagcaagggcgaggaggataatatggccattatcaaagaattcatgcgctttaaggtccacatggagggtag tgtcaacggtcatgaatttgagatagagggtgaaggggaaggtaggccttacgagggtactcaaactgcgaaattga aagtcacaaggggggtcccctccttttgcgtgggatatactctccccacaatttatgtacggttcaaaagcctat gttaagcaccctgcggacatccccgactacctgaaactcagttttcctgaaggcttcaagtgggagcgggtcatgaa ttttgaggacggtggggtcgtaacggtcactcaggactcatctcttcaagatggtgagtttatctataaagtaaagt tgcgcggtactaactttccgtccgacggaccagtaatgcaaaaaaaaacaatgggttgggaggcttcatccgaacgg atgtatcccgaagacggggctctcaagggtgagattaaacaaaggcttaaactgaaggatggaggccattacgatgc tgaagttaaaaccacgtataaagcgaagaaacccgttcagctgcctggtgcatataatgtgaatatcaaattggata taacctcacacaatgaggactatactatcgtagaacaatatgaacgggcggaaggacgacactcaaccgggggaatg gatgaactttataaa SEQ ID NO: 41 is the amino acid sequence of mCherry.
MVSKGEEDNMAIIKEFMRFKVHMEGSVNGHEFEIEGEGEGRPYEGTQTAKLKVTKGGPLPFAWDILSPQFMYGSKAY

VKHPADIPDYLKLSFPEGFKWERVMNFEDGGVVTVTQDSSLQDGEFIYKVKLRGTNFPSDGPVMQKKTMGWEASSER

MYPEDGALKGEIKQRLKLKDGGHYDAEVKTTYKAKKPVQLPGAYNVNIKLDITSHNEDYTIVEQYERAEGRHSTGGM

DELYK

SEQ ID NO: 42 is an exemplary nucleotide sequence encoding αGFPV$_H$H-GS
linker-mCherry-GS linker-horse ferritin heavy chain.
atggatgtgcagttggttgagtctggcggggcactcgtgcagccggggggtagtctgagattgagttgtgccgcctc cggatttccagtcaacagatattcaatgcgctggtatcgacaggcgccagggaaagagagagaatgggttgcgggta tgtcatcagcgggtgatcgatcctcttacgaggattcagtgaaagggcggtttacaataagccgagatgacgccaga aatacggtataccctccagatgaactccctcaagccggaagatacggcagtttactattgtaacgttaatgttggatt tgagtattggggccaaggaacgcaagtgaccgtcagcagtggtggtggaagtggcggagggtcaggaggcggatcta tggttagcaagggcgaggaggataatatggccattatcaaagaattcatgcgctttaaggtccacatggagggtagt gtcaacggtcatgaatttgagatagagggtgaaggggaaggtaggccttacgagggtactcaaactgcgaaattgaa agtcacaaggggggtcccctccttttgcgtgggatatactctccccacaatttatgtacggttcaaaagcctatg ttaagcaccctgcggacatccccgactacctgaaactcagttttcctgaaggcttcaagtgggagcgggtcatgaat ttttgaggacggtggggtcgtaacggtcactcaggactcatctcttcaagatggtgagtttatctataaagtaaagtt gcgcggtactaactttccgtccgacggaccagtaatgcaaaaaaaaacaatgggttgggaggcttcatccgaacgga tgtatcccgaagacggggctctcaagggtgagattaaacaaaggcttaaactgaaggatggaggccattacgatgct gaagttaaaaccacgtataaagcgaagaaacccgttcagctgcctggtgcatataatgtgaatatcaaattggatat aacctcacacaatgaggactatactatcgtagaacaatatgaacgggcggaaggacgacactcaaccgggggaatgg atgaactttataaaggggggaggaagcggggggagggtctgggggtggttcaggcgggggatcaggtggcgggagtatg -continued

```
actactgcattcccgagccaagtgcggcagaattaccaccaggactctgaagcggccatcaaccgacaaatcaacct ggaactgcatgcgtcttacgtttatctgtcaatgagcttttactttgatagagacgatgtcgcattgaagaacttcg ccaaatattttcttcatcagagccatgaggaaagggaacatgcagaaaaacttatgaaattgcagaaccagcgcggt ggaaggattttcctccaagacataaagaaaccggatcaggacgactgggagaatggcctgaaggcaatggaatgtgc acttcacctcgaaaagaacgtgaacgagagcctcctggaactgcataaattggccactgacaaaaacgatccacacc tgtgcgatttccttgagactcattatcttaacgagcaagtgaaagcaattaaagagttgggtgatcatgtcactaac ctgagacgcatgggggcaccagaaagcggcatggcagagtatttgtttgacaagcatacacttggtgagtgtgacga gtcttga
```

SEQ ID NO: 43 is the amino acid sequence of $\alpha GFPV_HH$-GS linker-mCherry-GS
linker-horse ferritin heavy chain.
```
DVQLVESGGALVQPGGSLRLSCAASGFPVNRYSMRWYRQAPGKEREWVAGMSSAGDRSSYEDSVKGRFTISRDDARN

TVYLQMNSLKPEDTAVYYCNVNVGFEYWGQGTQVTVSSGGGSGGGSGGGSMVSKGEEDNMAIIKEFMRFKVHMEGSV

NGHEFEIEGEGEGRPYEGTQTAKLKVTKGGPLPFAWDILSPQFMYGSKAYVKHPADIPDYLKLSFPEGFKWERVMNF

EDGGVVTVTQDSSLQDGEFIYKVKLRGTNFPSDGPVMQKKTMGWEASSERMYPEDGALKGEIKQRLKLKDGGHYDAE

VKTTYKAKKPVQLPGAYNVNIKLDITSHNEDYTIVEQYERAEGRHSTGGMDELYKGGGSGGGSGGGSGGGSGGGSMT

TAFPSQVRQNYHQDSEAAINRQINLELHASYVYLSMSFYFDRDDVALKNFAKYFLHQSHEEREHAEKLMKLQNQRGG

RIFLQDIKKPDQDDWENGLKAMECALHLEKNVNESLLELHKLATDKNDPHLCDFLETHYLNEQVKAIKELGDHVTNL

RRMGAPESGMAEYLFDKHTLGECDES
```

SEQ ID NO: 44 is an exemplary nucleotide sequence encoding $\alpha GFPV_HH$.
```
gatgtgcagttggttgagtctggcggggcactcgtgcagccggggggtagtctgagattgagttgtgccgcctccgg atttccagtcaacagatattcaatgcgctggtatcgacaggcgccagggaaagagagagaatgggttgcgggtatgt catcagcgggtgatcgatcctcttacgaggattcagtgaaagggcggtttacaataagccgagatgacgccagaaat acggtatacctccagatgaactccctcaagccggaagatacggcagtttactattgtaacgttaatgttggatttga gtattggggccaaggaacgcaagtgaccgtcagcagt
```

SEQ ID NO: 45 is the amino acid sequence of $\alpha GFPV_HH$.
```
DVQLVESGGALVQPGGSLRLSCAASGFPVNRYSMRWYRQAPGKEREWVAGMSSAGDRSSYEDSVKGRFTISRDDARN

TVYLQMNSLKPEDTAVYYCNVNVGFEYWGQGTQVTVSS
```

DETAILED DESCRIPTION

I. Summary of Terms

Unless otherwise noted, technical terms are used according to conventional usage. Definitions of common terms in molecular biology may be found in Benjamin Lewin, *Genes X,* published by Jones & Bartlett Publishers, 2009; and Meyers et al. (eds.), *The Encyclopedia of Cell Biology and Molecular Medicine,* published by Wiley-VCH in 16 volumes, 2008; and other similar references. As used herein, the singular forms "a," "an," and "the," refer to both the singular as well as plural, unless the context clearly indicates otherwise. As used herein, the term "comprises" means "includes." Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

Antigen: An intracellular component that can be specifically bound by a targeting domain As used herein, an "intracellular antigen" includes both native antigens found in cells, as well as non-native antigens expressed in a cell by recombinant methods. Non-limiting examples of antigens include, but are not limited to, proteins, lipids, polysaccharides, and nucleic acids.

Detecting: To identify the existence, presence, or fact of something. General methods of detecting may be supplemented with the protocols and reagents disclosed herein. For example, included herein are methods of detecting the localization of an intracellular antigen using FIREnano probes for fluorescence and electron microscopy.

Detection tag: A polypeptide that, when fused to a heterologous protein to form a fusion protein, facilitates the detection of the location of the fusion protein when it is expressed in cells. Non-limiting examples of detection tags include fluorescent proteins (such as mCherry) and fluorescent dye binding proteins, such as a halotag.

Expression: Translation of a nucleic acid into a protein.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Ferritin: Ferritins are a family of proteins that self-assemble into a multi-subunit globular-shaped nm-sized protein complex containing a cavity in which hydrated ferric oxide is mineralized. Specifically, 24 ferritin subunits self-assemble to form ~12 nm spherical nanoparticles with a hollow inner cavity and octahedral symmetry. In nature, the ferritin nanoparticle have ferroxidase activity, store ferric oxide in their cavity, and release it in a controlled fashion. Only the heavy chain subunit oxidizes ferrous iron to ferric oxide. Ferritin that is not combined with iron is called apoferritin.

Fluorescent protein: A protein that has the ability to emit light of a particular wavelength (emission wavelength) when exposed to light of another wavelength (excitation wavelength). Non-limiting examples of fluorescent proteins are the green fluorescent protein (GFP) from Aequorea victoria and natural and engineered variants thereof, spectral variants of GFP which have a different fluorescence spectrum (e.g., YFP, CFP), and GFP-like fluorescent proteins (e.g., DsRed;

and DsRed variants, for example, DsRed1, DsRed2, mCherry, mApple, mOrange, and mRasberry).

Fusion Protein: A single polypeptide chain including the sequence of two or more heterologous proteins, often linked by a peptide linker.

Host cells: Cells in which a vector can be propagated and its nucleic acid expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Isolated: An "isolated" biological component (such as a protein, for example a disclosed recombinant ferritin nanoparticle that has been substantially separated or purified away from other biological components, such as other chromosomal and extrachromosomal DNA, RNA, and proteins. Proteins, peptides and nucleic acids that have been "isolated" include those purified by standard purification methods. The term also embraces proteins or peptides prepared by recombinant expression in a host cell as well as chemically synthesized proteins, peptides and nucleic acid molecules. Isolated does not require absolute purity, and can include protein, peptide, or nucleic acid molecules that are at least 50% isolated, such as at least 75%, 80%, 90%, 95%, 98%, 99%, or even 99.9% isolated.

Nucleic acid molecule: A deoxyribonucleotide or ribonucleotide polymer or combination thereof including without limitation, cDNA, mRNA, genomic DNA, and synthetic (such as chemically synthesized) DNA or RNA. The nucleic acid can be double stranded (ds) or single stranded (ss). Where single stranded, the nucleic acid can be the sense strand or the antisense strand. Nucleic acids can include natural nucleotides (such as A, T/U, C, and G), and can include analogs of natural nucleotides, such as labeled nucleotides. "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein-coding regions, in the same reading frame.

Peptide Linker: A polypeptide of 50 or fewer amino acids that is used to fuse two heterologous polypeptides into one contiguous polypeptide chain. Non-limiting examples of peptide linkers include glycine linkers, serine linkers, and glycine-serine linkers, such as a 10 amino acid glycine-serine linker. Unless context indicates otherwise, reference to "linking" or "fusing" a first polypeptide and a second polypeptide (or to two polypeptides "linked" or "fused" together) by peptide linker refers to covalent linkage of the first and second polypeptides to the N- and C-termini of the peptide linker to form a single polypeptide chain. Such linkage is typically accomplished using molecular biology techniques to genetically manipulate DNA encoding the first polypeptide linked to the second polypeptide by the peptide linker.

Polypeptide and Protein: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with "protein."

Probe: A fusion protein comprising one or more detection tags (for example, one or more fluorescent proteins) or other reporter moiety (such as a heavy chain ferritin subunit linked to ferric oxide) that is used to detect the location of a target antigen in a cell.

Sequence identity: The similarity between amino acid sequences is expressed in terms of the similarity between the sequences, otherwise referred to as sequence identity. Sequence identity is frequently measured in terms of percentage identity; the higher the percentage, the more similar the two sequences are. Homologs, orthologs, or variants of a polypeptide will possess a relatively high degree of sequence identity when aligned using standard methods.

Methods of alignment of sequences for comparison are well known in the art. Various programs and alignment algorithms are described in: Smith & Waterman, *Adv. AppL Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. In the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

Variants of a polypeptide are typically characterized by possession of at least about 75%, for example, at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet.

As used herein, reference to "at least 90% identity" (or similar language) refers to "at least 90%, at least 91%, at least 92%, at least 93%, at least 94%, at least 95%, at least 96%, at least 97%, at least 98%, at least 99%, or even 100% identity" to a specified reference sequence.

Single chain antibody: A single polypeptide chain that includes at least one antibody variable region, or an engineered variant thereof, that specifically binds to a target antigen. Single chain antibodies include, for example, antibody formats containing heavy and light chain variable regions ($V_H$ and $V_L$, respectively) expressed as a single polypeptide chain, such as a single-chain variable fragment (scFv), as well as antibody formats containing a single variable region that specifically binds to the target antigen, such as a single domain antibodies (sdAb or nanobody). An scFv is a genetically engineered molecule containing the heavy and light chain variable domains of one or more antibody(ies) linked by a suitable polypeptide linker as a genetically fused single chain molecule. The intramolecular orientation of the heavy chain variable domain and the light chain variable domain in a scFv is typically not decisive for scFvs. Thus, scFvs with both possible arrangements ($V_H$-domain-linker domain-$V_L$-domain; $V_L$-domain-linker domain-$V_H$-domain) may be used. A single domain antibody is a monomeric variable region that specifically binds to a target antigen. In some embodiments, single-domain antibodies are based on heavy-chain only antibodies found in camelids, which are called $V_H$H fragments or camelid antibodies. Additional description of single chain antibody formats can be found, for example, in Kontermann and Dubel (Ed), Antibody Engineering, Vols. 1-2, $2^{nd}$ Ed., Springer Press, 2010.

Specifically bind: When referring to the targeting domain of a genetically encoded FIREnano probe as provided herein, specifically bind refers to a binding reaction which determines the presence of a target antigen in the presence of a heterogeneous population of proteins and other biologics. Thus, under designated conditions, a targeting domain binds preferentially to a particular target antigen in a cell and does not bind in a significant amount to other biological components of the cell (such as proteins or polysaccharides). Specific binding can be determined by methods known in the art.

Targeting domain: A polypeptide that that specifically binds to an intracellular target antigen, and that when fused to a heterologous protein to form a fusion protein, facilitates the co-localization of the fusion protein with the target antigen in cells. Non-limiting examples of targeting domains include single domain antibodies that specifically bind to an intracellular antigen, such as genomic DNA or RNA.

Target antigen: An intracellular antigen whose detection and/or intracellular localization is intended.

Under conditions sufficient for: A phrase that is used to describe any environment that permits a desired activity.

II. FIREnano Probes

This disclosure provides novel genetically encoded probes that are expressed in a cell to label an intracellular target (e.g., protein/DNA) for both light microscopy (e.g., fluorescence) and EM. The probes are termed fluorescent-iron EM ferritin nanoparticle (FIREnano) probes and are comprised of an assembly of fusion proteins. The fusion proteins comprise a targeting domain that specifically binds to the intracellular target, a detection tag that can be used to detect the intracellular location of the probe using light (e.g., fluorescence) microscopy, and a mammalian (e.g., horse) ferritin heavy chain subunit. The ferritin subunit in the fusion protein self-assembles in mammalian cells to form a globular multi-subunit ferritin nanoparticle that oxidizes ferrous iron to ferric oxide. When assembled, the targeting domains and the detection tags extend radially outward from the exterior surface of the globular ferritin nanoparticle. The detection tag can be used to identify the intracellular location of the fusion protein by light microscopy, and the ferric oxide in the ferritin nanoparticle can be to detect the intracellular location of the probe using EM.

The order of the components of the fusion protein can vary. However, the ferritin heavy chain subunit is included at the C-terminal portion of the fusion protein. In some embodiments, the fusion protein comprises, in an N- to C-terminal direction, the targeting domain that specifically binds to an intracellular antigen, the detection tag, and the ferritin heavy chain subunit. In other embodiments, the fusion protein comprises, in an N- to C-terminal direction, the detection tag, the targeting domain that specifically binds to an intracellular antigen, and the ferritin heavy chain subunit.

In the context of the fusion protein, the ferritin heavy chain subunit self-assembles into a globular multi-subunit ferritin nanoparticle in an intracellular environment. If endogenous ferritin heavy and light chain molecules are present in the intracellular environment, then the resulting globular multi-subunit ferritin nanoparticle may also include one or more endogenous ferritin heavy or light chains. For example, adding iron salt into cell culture medium can induce expression of endogenous human ferritin heavy and light chain, which may be incorporated into the globular multi-subunit ferritin nanoparticle containing the fusion protein of the FIREnano probe. The mixing ratio of endogenous ferritin heavy and light chains to the fusion protein of the FIREnano probe can be controlled, for example, by the ratio of endogenous ferritin heavy and light chains to the fusion protein of the FIREnano probe and monitored by native gel assay Further, the self-assembled ferritin heavy chain subunit of the fusion protein oxidizes ferrous iron to ferric oxide. The ferric oxide can be detected as a heavy particle using EM. In some embodiments, the ferritin subunit included in the fusion protein is a horse ferritin subunit that comprises or consists of the amino acid sequence set forth as SEQ ID NO: 21.

The detection tag included in the fusion protein facilitates detection of the intracellular location of the probe using light (e.g., fluorescence) microscopy. In some embodiments, the detection tag is a fluorescent protein. Any suitable fluorescent protein can be used, for example, GFP or a variant thereof, such as YFP or CFP, or a GFP-like fluorescent protein, such as DsRed and DsRed variants, such as DsRed1, DsRed2, mCherry, mApple, mOrange, or mRasberry. In some embodiments, the detection tag is an mCherry fluorescent protein that comprises or consists of the amino acid sequence set forth as SEQ ID NO: 41. In additional embodiments, the detection tag is a fluorescent dye binding protein, such as a halotag. In such embodiments, the intracellular location of the fusion protein can be detected by applying the fluorescent dye that binds to the fluorescent dye binding protein to the cells. In some embodiments, the detection tag is a halotag comprising or consisting of the amino acid sequence set forth as SEQ ID NO: 39.

The targeting domain included in the fusion protein specifically binds to an intracellular target antigen, thereby facilitating the co-localization of the fusion protein with the target antigen. In some embodiments, the targeting domain is a single chain antibody (such as a scFv or a $V_HH$) that specifically binds to the target antigen.

The target antigen can be any intracellular antigen of interest, such as a protein (e.g., chromatin) or a nucleic acid (e.g., DNA or RNA). In some embodiments, the target antigen is a heterologous protein expressed in the cell, and the targeting domain specifically binds to the heterologous antigen. In other embodiments, the target antigen is a native antigen expressed within the cell, and the targeting domain specifically binds to the native antigen.

Non-limiting examples of targeting domains include a $\alpha$GFPV$_H$H targeting domain (which specifically binds to GFP), an anti-suntag scFv (which specifically binds to suntag), an anti-mCherry nanobody (which specifically binds to mCherry), RNA binding proteins that specifically bind to an RNA tag (such as MCP, which specifically bind to the MS2 RNA tag, PCP, which specifically bind to the PP7 RNA tag, and N22p, which specifically bind to the lambda N22 RNA tag), and a PUF protein that specifically binds to PUF sequences in the 3' untranslated region (3'UTR) of specific target mRNAs.

For targeting of particular DNA sequences, DNA binding proteins, such as transcription factors, can used as a targeting domain In additional embodiments, the targeting domain is a dCas9 protein or a dCas13d protein that can be used with CRISPR technology to label a particular genomic locus, or a transcription activator-like effector (TALE) that can be used with TALEN technology to label a particular genomic locus.

In some embodiments, the targeting domain is a subunit of a dimerization domain, such as an inducible dimerization domain.

In some embodiments, the targeting domain comprises or consists of the amino acid sequence set forth as any one of SEQ ID NO: 27 (MS2 binding protein, MCP), SEQ ID NO: 28 (lambda N22 RNA binding protein, N22p), SEQ ID NO: 29 (PP7 RNA stem loop coat protein, PCP), SEQ ID NO: 30 (anti-suntag scFv), SEQ ID NO: 32 (PUFa), SEQ ID NO: 33 (PUFb), SEQ ID NO: 34 (FRB), SEQ ID NO: 35 (FKBP), SEQ ID NO: 36 (dSpCas9), or SEQ ID NO: 45 ($\alpha$GFPV$_H$H).

The targeting domain, the detection tag, and the ferritin heavy chain subunit included in the fusion protein can be directly linked via peptide bond, or indirectly linked by a peptide linker. Any appropriate peptide linker can be used, such as a glycine-serine peptide linker, for example as set forth as SEQ ID NO: 37 (GGGSGGGSGGGS). In some embodiments, the detection tag and the ferritin heavy chain subunit are fused via a peptide linker, such as a glycine-serine peptide linker, for example as set forth as SEQ ID NO: 37. In some embodiments, the targeting domain and the detection tag are fused via a peptide linker, such as a glycine-serine peptide linker, for example as set forth as SEQ ID NO: 37. In some embodiments, the detection tag and the ferritin heavy chain subunit, and the targeting domain and the detection tag, are fused via a peptide linker, such as a glycine-serine peptide linker, for example as set forth as SEQ ID NO: 37.

In some embodiments, the fusion protein further comprises a nuclear localization sequence (NLS) to increase localization of the fusion protein in the nucleus of cells. Any suitable NLS can be incorporated into the fusion protein, such as the SV40 Large T-antigen NLS, which has the sequence of PKKKRKV (residues 24-30 of SEQ ID NO: 25). The nuclear localization sequence can be included at any appropriate location within the fusion protein, typically N-terminal to the targeting domain In some embodiments, the fusion protein further comprises additional proteins tags for various purposes, for example for purification and/or detection. In some embodiments, the fusion protein further comprises a FLAG tag (DYKDDDK, residues 16-23 of SEQ ID NO: 25) near or at the N-terminus of the fusion protein.

In some embodiments, the fusion protein comprises or consists of the amino acid sequence set forth as any one of SEQ ID NOs: 25, 26, or 43.

The fusion protein can include sequence modifications, such as amino acid substitutions, deletions or insertions, as long as the fusion protein retains the functional properties of the targeting domain (specific binding to the target antigen), detection tag (detection by light (e.g., fluorescence) microscopy), and ferritin heavy chain subunit (self-assembly into a ferritin nanoparticle and oxidation of ferrous iron to ferric oxide). These variations in sequence can be naturally occurring variations or they can be engineered through the use of appropriate genetic engineering techniques. The fusion protein can be derivatized or linked to another molecule (such as another peptide or protein), as long as the fusion protein retains the functional properties of the targeting domain (specific binding to the target antigen), detection tag (detection by light (e.g., fluorescence) microscopy), and ferritin heavy chain subunit (self-assembly into a ferritin nanoparticle and oxidation of ferrous iron to ferric oxide).

In some embodiments, the fusion protein can be produced in cells (for example by expression from a nucleic acid molecule that encodes the probe (see Section III below), and isolated, for example, by preparative chromatography and immunological separations.

III. Polynucleotides and Expression

Polynucleotides encoding a subunit of the disclosed FIREnano probes are also provided. These polynucleotides include, for example, DNA, cDNA and RNA sequences encoding a subunit of the disclosed FIREnano probes. One of skill in the art can readily use the genetic code to construct a variety of functionally equivalent nucleic acids, such as nucleic acids which differ in sequence but which encode the same protein sequence. In a non-limiting embodiment, the polynucleotide comprises the sequence set forth as any one of SEQ ID NOs: 7, 8, or 42.

Exemplary nucleic acids can be prepared by cloning techniques. Examples of appropriate cloning and sequencing techniques, and instructions sufficient to direct persons of skill through many cloning exercises are known (see, e.g., Sambrook et al. (Molecular Cloning: A Laboratory Manual, 4$^{th}$ ed., Cold Spring Harbor, New York, 2012) and Ausubel et al. (In Current Protocols in Molecular Biology, John Wiley & Sons, New York, through supplement 104, 2013). Product information from manufacturers of biological reagents and experimental equipment also provide useful information. Such manufacturers include the SIGMA Chemical Company (Saint Louis, MO), R&D Systems (Minneapolis, MN), Pharmacia Amersham (Piscataway, NJ), CLONTECH Laboratories, Inc. (Palo Alto, CA), Chem Genes Corp., Aldrich Chemical Company (Milwaukee, WI), Glen Research, Inc., GIBCO BRL Life Technologies, Inc. (Gaithersburg, MD), Fluka Chemica-Biochemika Analytika (Fluka Chemie AG, Buchs, Switzerland), Invitrogen (Carlsbad, CA), and Applied Biosystems (Foster City, CA), as well as many other commercial sources known to one of skill.

Nucleic acids can also be prepared by amplification methods Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

The polynucleotides encoding a subunit of a disclosed FIREnano probe can include a recombinant DNA which is incorporated into a vector (such as an expression vector) into an autonomously replicating plasmid or virus or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single and double forms of DNA.

Polynucleotide sequences encoding a subunit of a disclosed FIREnano probe can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

DNA sequences encoding a subunit of a disclosed FIREnano probe can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Hosts can include microbial, yeast, insect and mammalian organisms. Methods of expressing nucleic acid sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human) Exemplary cells of use include *Escherichia coli, Bacillus subtilis, Saccharomyces cerevisiae, Salmonella typhimurium, Neurospora,* and immortalized mammalian cell lines. Techniques for the propagation of mammalian cells in culture are well-known (see, e.g., Helgason and Miller (Eds.), 2012, Basic Cell Culture Protocols (Methods in Molecular Biology), 4$^{th}$ Ed., Humana Press). Examples of commonly used mammalian host cell lines are HeLa cells, CHO cells, and COS cell lines, although cell lines may be used, such as cells designed to provide higher expression, desirable glycosylation patterns, or other features. In some embodiments, the host cells include HEK293 cells.

Transformation of a host cell with recombinant DNA is typically carried out by conventional techniques. Where the host is prokaryotic, such as, but not limited to, *E. coli,* competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or viral vectors can be used. Eukaryotic cells can also be co-transformed with polynucleotide sequences encoding a disclosed antigen, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Viral Expression Vectors, Springer press, Muzyczka ed., 2011). One of skill in the art can readily use an expression systems such as plasmids and vectors of use in producing proteins in cells including higher eukaryotic cells such as the COS, CHO, HeLa, and myeloma cell lines.

Modifications can be made to a nucleic acid encoding a subunit of the disclosed FIREnano probe without diminishing its biological activity. Some modifications can be made to facilitate the cloning, expression, or incorporation of the FIREnano probe into a fusion protein. Such modifications include, for example, termination codons, a methionine added at the amino terminus to provide an initiation, site, additional amino acids placed on either terminus to create conveniently located restriction sites, or additional amino acids (such as poly His) to aid in purification steps.

V. Methods of Detection

Further provided are methods of detecting the location of a target antigen in a cell. The method comprises expressing a nucleic acid molecule encoding a FIREnano probe in the cell. As discussed above, the FIREnano probe is a fusion protein comprising a targeting domain that specifically binds to the intracellular target antigen, a detection tag that can be used to detect the intracellular location of the probe using light (e.g., fluorescence) microscopy, and a mammalian (e.g., horse) ferritin heavy chain subunit that self-assembles into globular multi-subunit ferritin nanoparticle that oxidizes ferrous iron to ferric oxide, and that can be used to detect the intracellular location of the probe using EM. Once expressed in the cell, the targeting domain of the fusion protein specifically binds to the target antigen, and the location of the detection tag and the ferritin nanoparticle in the host cell can be detected using fluorescence microscopy and EM, respectively, to detect the location of the target antigen in the cell.

In several embodiments, the method is performed in vitro, with host cells expressing the fusion protein. In several embodiments, the host cells are incubated in growth medium comprising transferrin and/or ferric ammonium citrate.

In some embodiments, the fusion protein is expressed in the host cells, and then the host cells are fixed prior to analysis with light (e.g., fluorescence) microscopy and EM. In other embodiments, the fusion protein is expressed in the host cells, and the fusion protein is detected by live cell imaging prior to fixation for analysis with light (e.g., fluorescence) microscopy and/or EM.

Any appropriate light and/or electron microscopy technique (e.g., fluorescence microscopy, TEM, EMT, ChromEMT) can be used to detect the detection tag and the ferritin nanoparticle in order to determine the location of the fusion protein in the host cells.

Further, any appropriate host cell can be used in the disclosed methods. In several embodiments the host cell is a mammalian cell, such as a human cell.

EXAMPLES

The following examples are provided to illustrate particular features of certain embodiments, but the scope of the claims should not be limited to those features exemplified.

Example 1

Genetically Encoded FIREnano Probes for Visualizing Structures within Intact Cells by Fluorescent and Electron Microscope The example illustrates genetically encoded FIREnano probes that are expressed in a cell to label an intracellular target (e.g., protein/DNA) for both fluorescence and EM. The disclosed probes can be used for dynamic live imaging and EM ultrastructure.

Figure 1C:
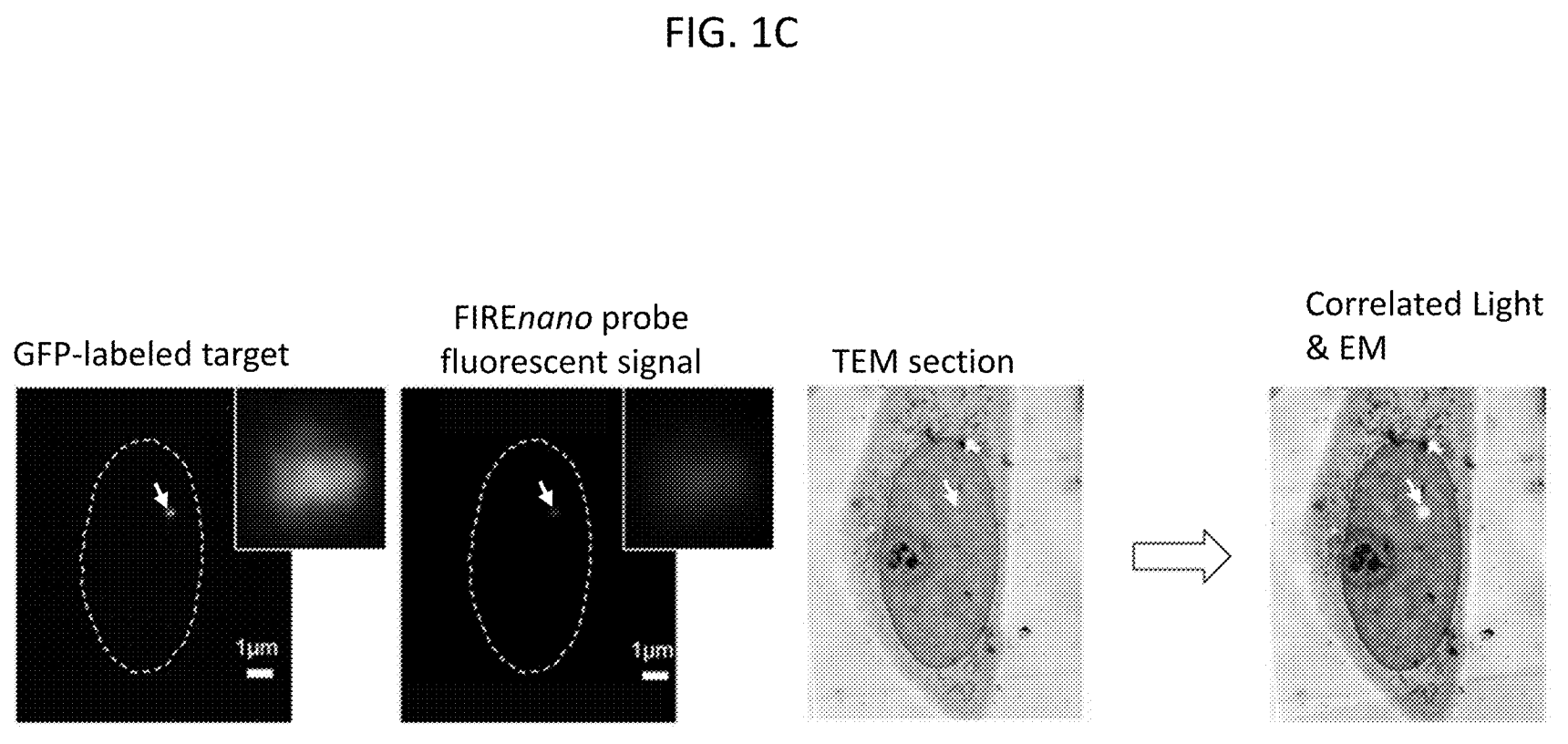

Ferritins are a family of large multi-subunit proteins that self-assemble to form a cavity in which hydrated ferric oxide is mineralized and stored (FIG. 1B). Ferritin subunits self-assemble to form 24mer 12 nm spherical particles with a hollow inner cavity and octahedral symmetry. Mammalian ferritins include heavy and light chains, however, only the heavy chain subunit oxidizes ferrous iron to ferric oxide. Interestingly, the mammalian ferritin heavy chain self-assembles into a ferritin 24mer in the absence of the light chain. Metal ions pass into the inner cavity through channels between ferritin subunits. Each subunit includes four long helical bundles and a tilted short R-helix connected by a flexible loop.

Several different embodiments of the genetically encoded FIREnano probes were designed and tested. Human codon-optimized E. coli ferritin constructs were fused to the mCherry fluorescent protein and a lama antibody that specifically binds to GFP (termed $\alpha GFPV_HH$-mCherry-E. coli Ferritin). Llama antibodies are single chain antibodies that only contain a heavy chain variable region ($V_HH$). Ferritin assembles in cytoplasm. Therefore, to concentrate the synthetic constructs in the nucleus a nuclear localization sequence (NLS) was also included. The DNA sequence encoding the $\alpha GFPV_HH$-mCherry-E. coli Ferritin probe is provided as SEQ ID NO: 1. To test this probe, several different cell-lines that stably express GFP linked to a subcellular targeting element were used: Adenovirus protein ORF3-GFP which forms huge GFP labeled fibers; Connexin43-GFP which forms GFP-labeled gap junction structures; TRF1-GFP, which contains GFP-labeled telomere ends (human telomeres are tethered to the nuclear envelope during postmitotic nuclear assembly); and LacI-GFP, which contains GFP-labeled lacO sequences in chromosome 1. The colocalization of mCherry with GFP in these cell lines demonstrates that the $\alpha GFPV_HH$-mCherry-E. coli Ferritin constructs labeled GFP tagged locus very well (FIG. 2).

Figure 2A:
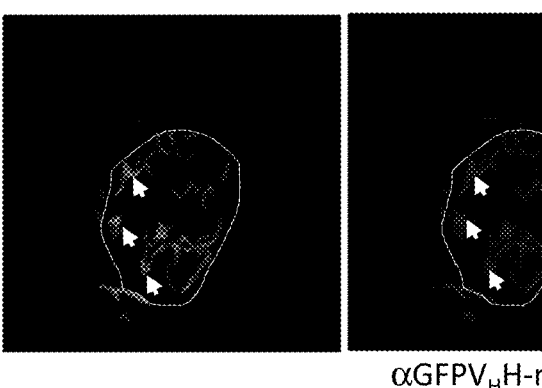
FIGS. 2A-2D. Genetically encoded FIREnano probes label discrete loci in cells. Plasmid encoding the $\alpha$GFPV$_H$H-mCherry-*E. coli* ferritin FIREnano probe was transfected into cells with GFP-tagged loci under conditions for iron loading of ferritin. GFP and mCherry fluorescence was detected to localize the GFP-tag and FIREnano probe, respectively. The FIREnano probe was expressed in U2OS cells expressing ORF3-GFP that forms GFP labeled intracellular fibers (FIG. 2A), Hela cells expressing TRF1-GFP that labels telomere sequences (FIG. 2B), U2OS cells expressing LacI-GFP that labels LacO repeat sequences (artificially incorporated into Chromosome 1) (FIG. 2C), and U2OS cells expressing Connexin43 (CX43)-GFP that labels gap junctions (FIG. 2D). Arrows highlight areas of colocalized GFP and mCherry signal.
Figure 2B:
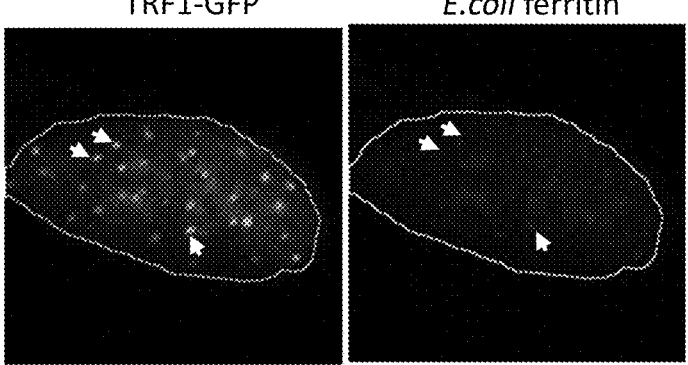
Figure 2C:
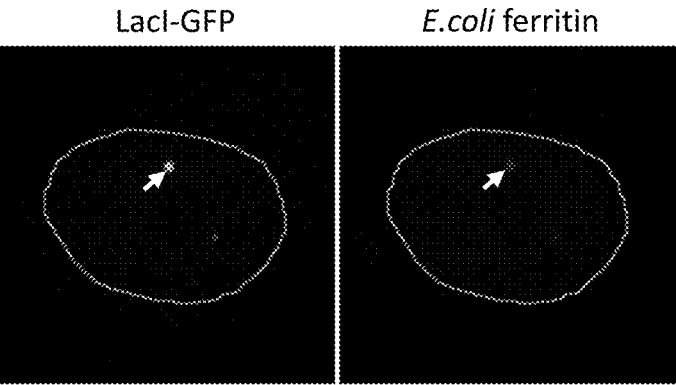
Figure 2D:
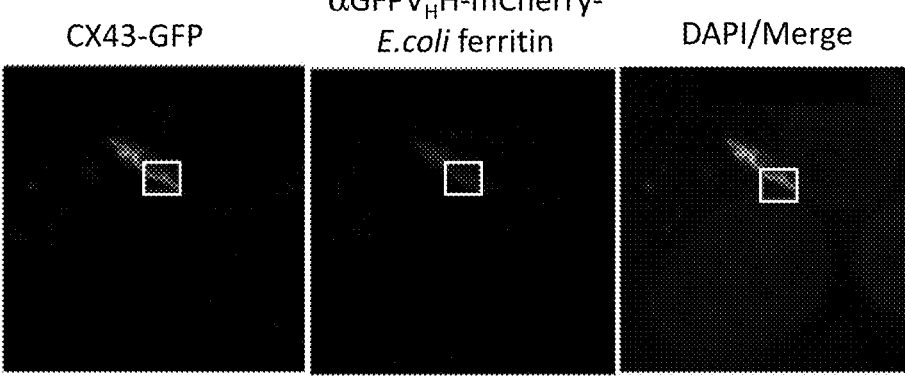
Figure 3A:
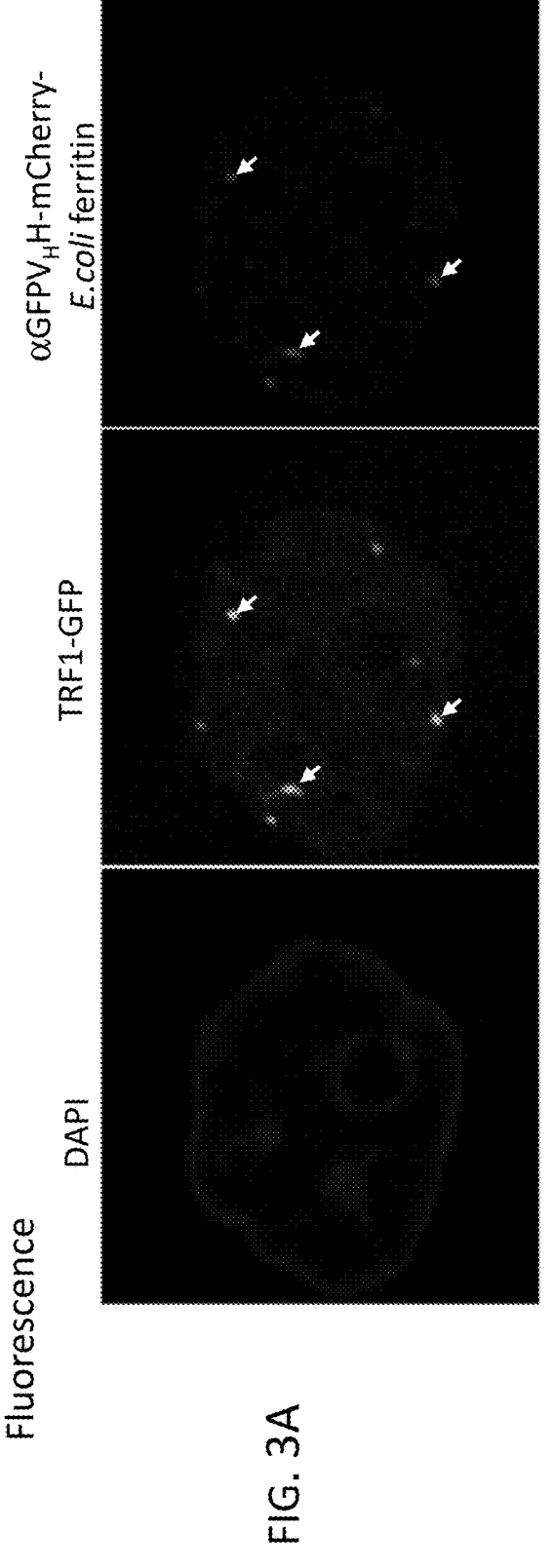
FIGS. 3A and 3B. TEM of TRF1-GFP telomere locus labeled by the $\alpha$GFPV$_H$H-mCherry-*E. coli* ferritin.

TRF1-GFP cells were transfected with $\alpha GFPV_HH$-mCherry-E. coli Ferritin. 24 hours after transfection, cells were fixed with glutaraldehyde, further fixed by aqueous osmium teteroxide, dehydrated in ethanol series, and finally embedded in durcupan ACM resin. Navminator software was used to correlate light and EM images and find the same region in EM sections. TEM images of thin sections are shown in FIG. 3. Despite the ability of the $\alpha GFPV_HH$-mCherry-E. coli Ferritin construct to co-localize and fluorescently label GFP tagged proteins, iron particles in the corresponding EM sections of the regions of interest were not detected. Similar results were obtained in corresponding assays in the cells expressing LacI-GFP (to label lacO sequences in chromosome 1) (FIG. 4) and cells expressing connexin43-GFP which forms GFP-labeled gap junction structures (FIG. 5).

Figure 6:
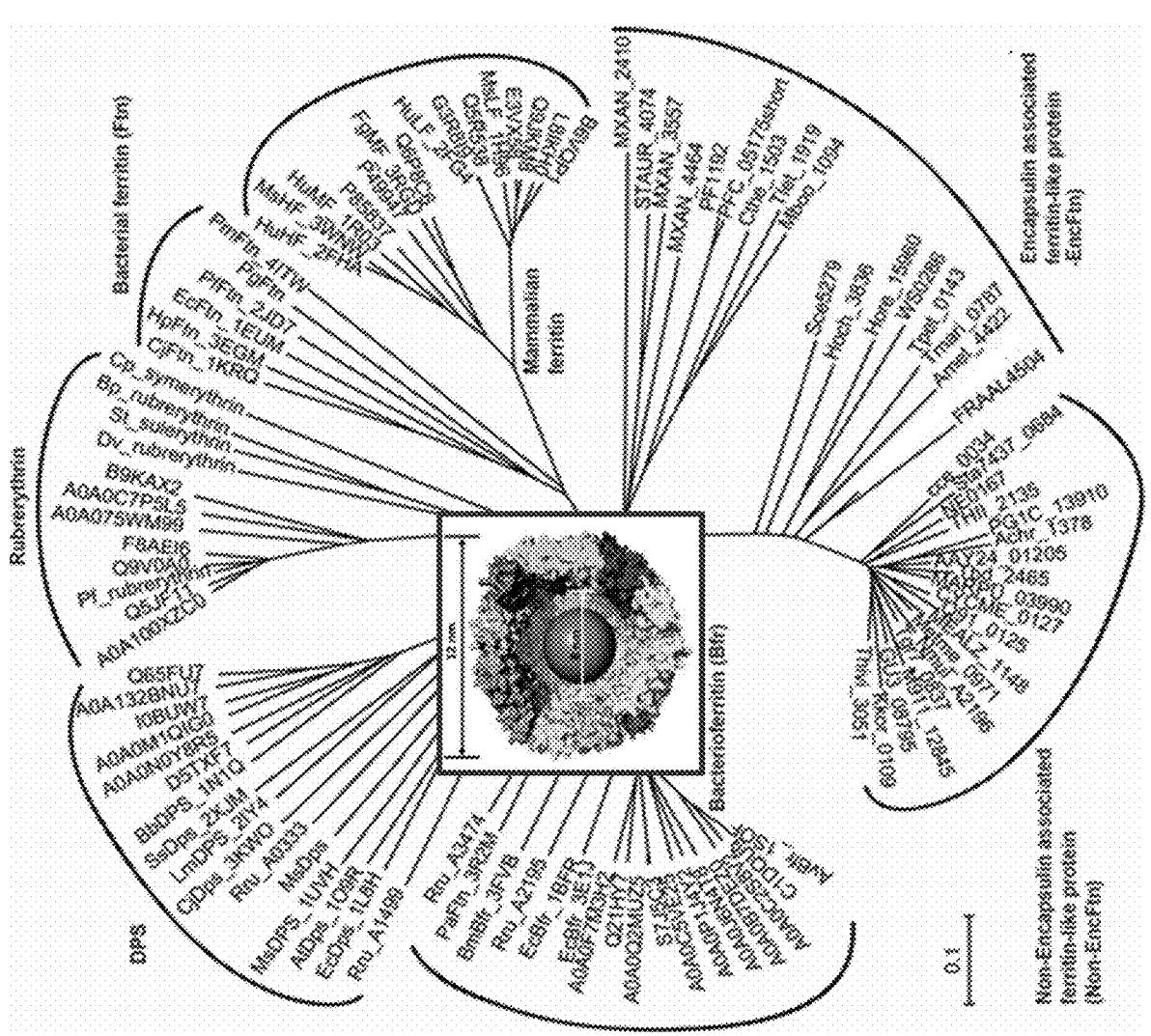
FIG. 6. Phylogenetic tree of ferritin family proteins.
Figures 7A, 7B, 7C:
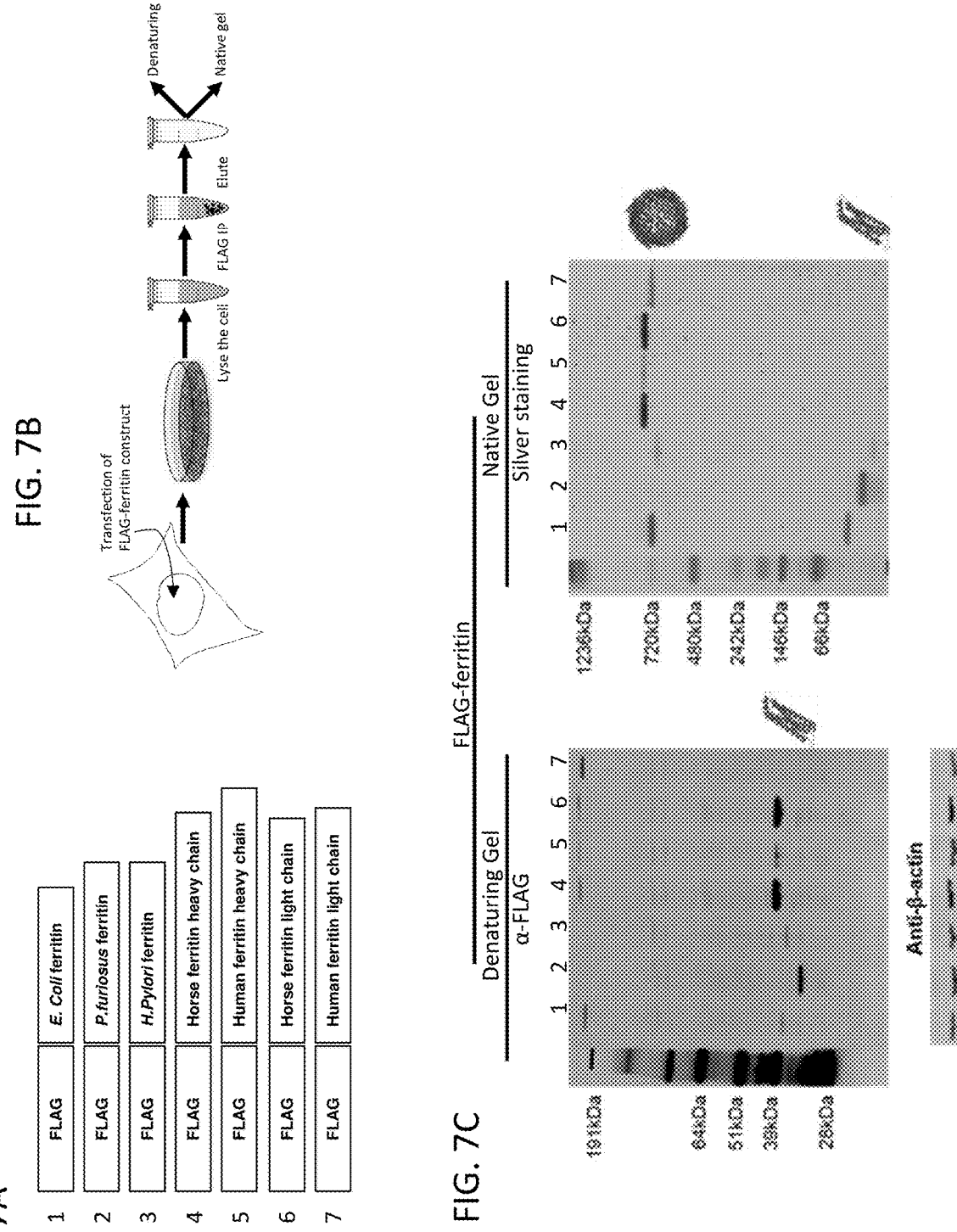
FIGS. 7A-7C. Assembly of genetically modified ferritin particles from several species.

It was reasoned that the lack of EM contrast could be due to the failure of *E. coli* ferritin fusion proteins to assemble and/or load iron in the nucleus of mammalian cells. Additionally, ferritin is found across the different kingdoms of life (FIG. 6). Thus, it was also reasoned that ferritin other than *E. coli* ferritin might perform better in mammalian cells. Therefore, ferritin from several different organisms was fused with an N-terminal 3× FLAG tag and assessed for assembly into iron storing particles in mammalian cells (FIG. 7). These included ferritins from Helicobacter pylori, Horses, Humans, *E. coli*. The FLAG-ferritin protein was immunoprecipitated from mammalian cells lysate using RIPA buffer. FLAG-ferritin was eluted by competition with flag peptide and analyzed using a combination of SDS PAGE and native gel electrophoresis to reveal the expression and self-assembly of the FLAG-ferritin. Ferritin monomers are about 21 kDa molecular weight, whereas the self-assembled nanoparticle is about 600-700 kDa. The native gel analysis revealed that the FLAG-*E. coli* ferritin self-assemble into the complex poorly, indicating that the $\alpha$GFPV$_H$H-mCherry-*E. coli* Ferritin expressed in mammalian cells also failed to self-assemble. It was determined that mammalian ferritins assembled better than bacteria ferritins in human cells. Horse ferritin heavy chain performed particularly well when compared to other ferritin fusion constructs, therefore, horse ferritin was selected for further analysis.

Mammalian ferritins comprise both heavy and light chains. However, only the heavy chain oxidizes ferrous iron to ferric oxide, and the iron core is where EM contrast comes from. The *E. coli* ferritin particles comprise heavy chains only, which is a very simple system. Also, many bacterial proteins can express and function well in human cells, such as bacterial proteins used in the CRISPER technology. Thus, it is surprising that the *E. coli* ferritin did not self-assemble well in human cells.

Figure 8A:
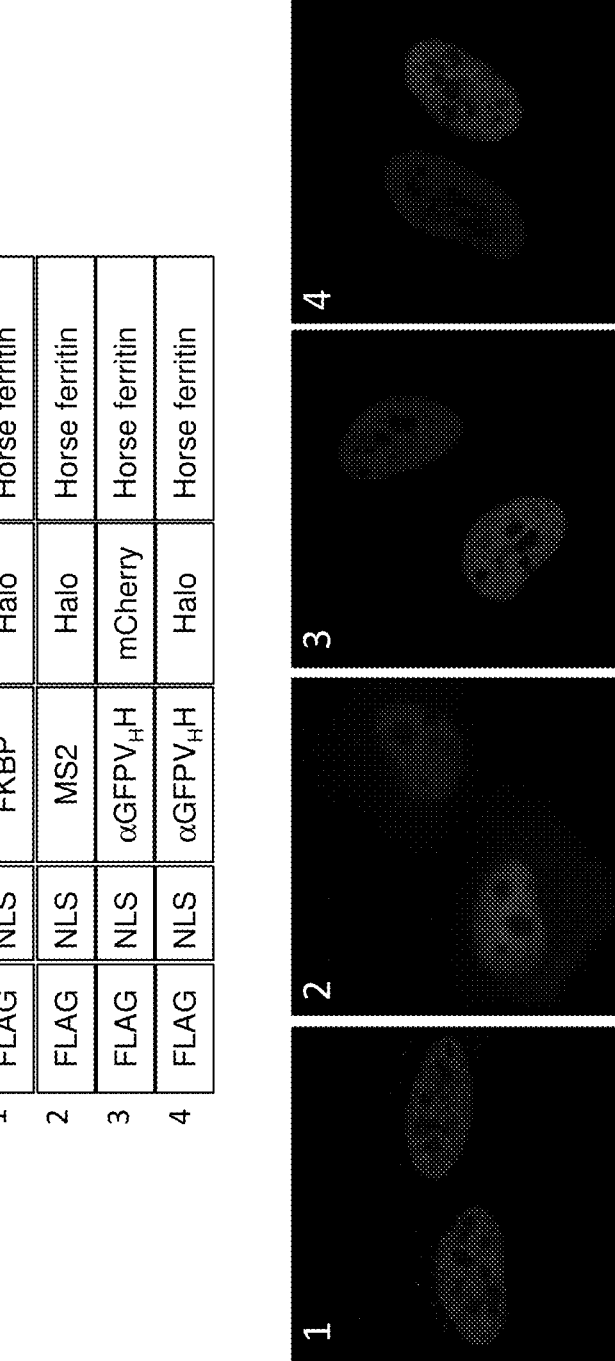
FIGS. 8A and 8B. Assembly of genetically modified FIREnano probes containing horse ferritin.
Figure 8B:

Assembly of candidate genetically modified FIREnano probes by using horse ferritin was assessed (FIG. 8). These probes were expressed in mammalian cells and detected by mCherry fluorescence or Halo tag labeling, showing that these probes do not aggregate in cells. The expressed constructs were subjected to native PAGE, which showed that all the horse ferritin constructs were able to assemble as >500 kDa particles. However, iron loading was relatively inefficient as evidenced by Prussian Blue staining of ferritins on native gels when compared to purified horse spleen ferritin as a positive control. The results indicate the FIREnano probes form ferritin nanoparticles but are not iron-loaded efficiently when expressed under typical cell-culture conditions.

Figure 9:
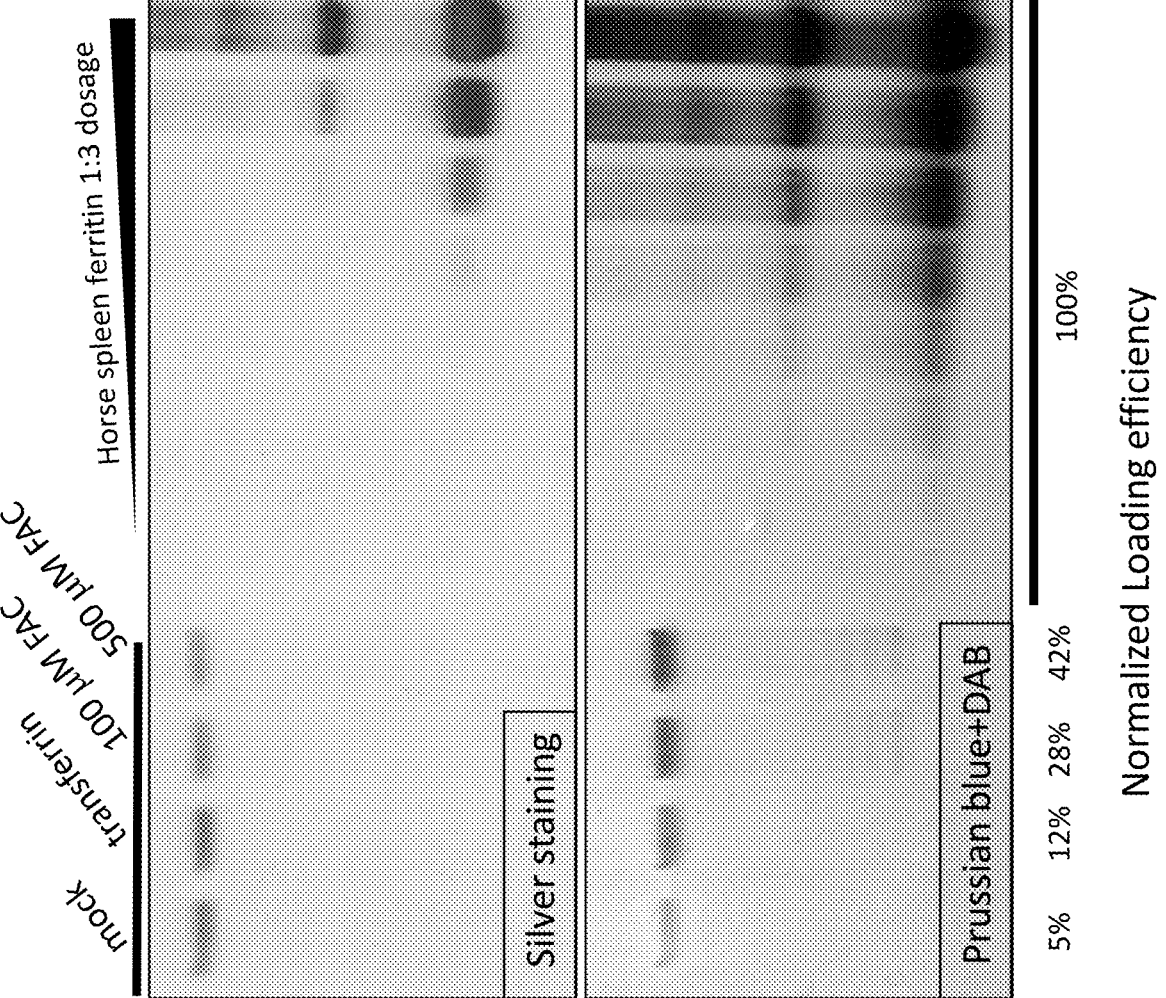
FIG. 9. Optimization of iron loading efficiency of genetically modified FIREnano probes. The FIREnano probes 1-4 from FIG. 8 were expressed in human cells and an iron source (transferrin or ferric ammonium citrate (FAC)) was added to the cell culture media to increase the iron loading efficiency. Lane 1: normal condition. Lane 2: transferrin. Lane 3: 100 $\mu$M FAC. Lane 4: 500 $\mu$M FAC. Upper panel: Native PAGE and silver staining of purified FIREnano probes indicates the relative expression level. Iron-loaded ferritin purified from spleen was used as a standard. Lower panel: Native gel, prussian blue and DAB staining showing the relative amount of ferric iron loaded inside ferritin particles in each condition. Normalized loading efficiency was calculated by normalizing band value from Prussian blue+DAB staining relative to sliver staining. The 500 $\mu$M FAC condition provided the greatest level of iron loading for the FIREnano probe.

To overcome this, transferrin and/or ferric ammonium citrate (FAC) was added into the cell culture medium. Prussian blue staining of particles in native gels showed that the iron loading efficiency was increased from 5% to 42% after optimization (FIG. 9).

Figures 10A, 10B, 10C:
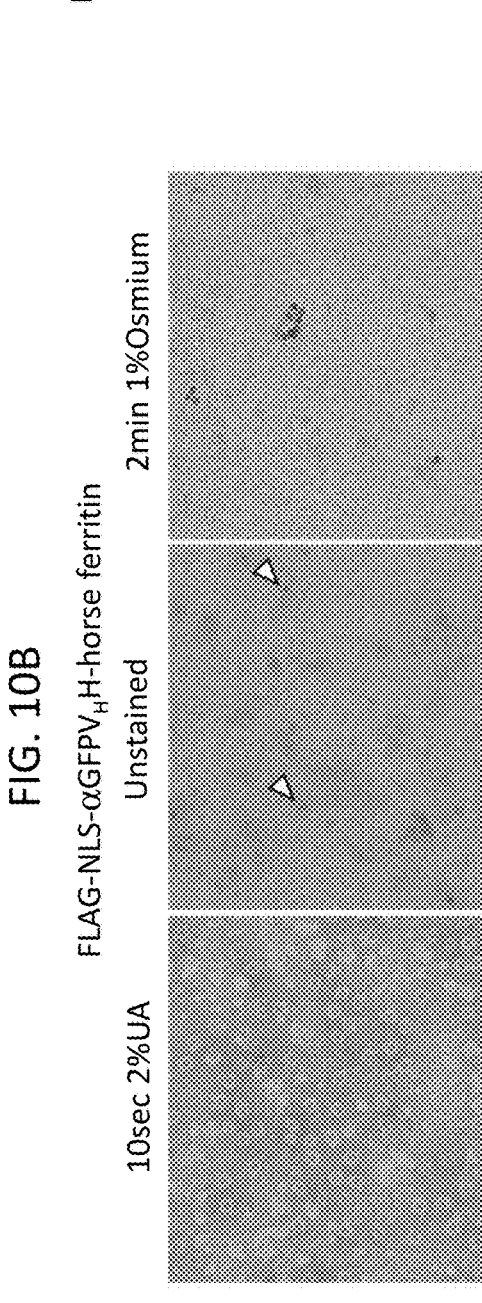
FIGS. 10A-10C. TEM and Cryo-EM of purified Flag-tagged horse ferritin nanoparticles.

Finally, both TEM and Cryo-EM was performed on horse spleen ferritin and the FLAG-NLS-$\alpha$GFPV$_H$H-horse ferritin purified from human cells, which show that they self-assemble into particles that have ~12 nm protein shells and ~4-5 nm ferric oxide cores (FIG. 10), very similar to the commercially purchased horse spleen ferritin.

Figure 12:
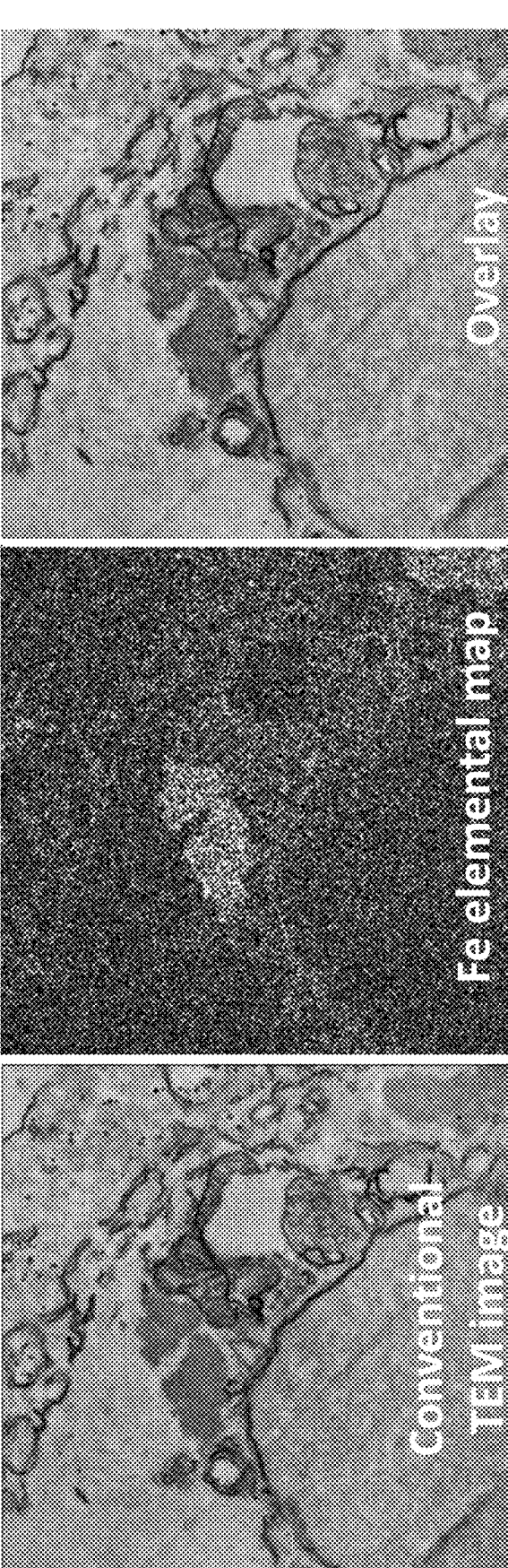
FIG. 12. Electron energy loss spectroscopy (EELS) imaging of ORF3-GFP fibers labeled with the $\alpha$GFPV$_H$H-mCherry-ferritin FIREnano probe. Left panel: TEM; middle panel: Fe EELS; right panel: overlay of TEM and EELS images.

To show that the $\alpha$GFPV$_H$H-mCherry-horse ferritin probe could label GFP tagged intracellular targets through $\alpha$GFPV$_H$H binding, an adenoviral protein E4-ORF3 marker was used as an example since it assembles huge fibers when it is transiently over-expressed. The large fiber morphology allows facile correlation of light and EM images, which facilitates EM analysis. ORF3-GFP expressing U2OS cells were transfected with $\alpha$GFPV$_H$H-mCherry-ferritin encoding plasmid and the cells were cultured with 500 μM FAC to iron-load the FIREnano probe. $\alpha$GFPV$_H$H-mCherry-ferritin successfully labeled ORF3-GFP fiber by fluorescent signal. Furthermore, iron core signals (dark round spots) originating from ferritin particles were identified in the ORF3-GFP fiber region by TEM (FIG. 11). Using Electron energy loss spectroscopy (EELS), the enrichment of iron element at the ferritin labeled ORF3 region was confirmed (FIG. 12), indicating the dark particles are loaded with ferric oxide and their identity as ferritin particles.

mCherry can form a dimer. Therefore, to offset the possibility that mCherry-ferritin constructs can nucleate with each other at high local concentrations, mCherry was replaced with a Halo-tag. The Halo tag is a modified hydrolase that covalently links chloroalkane-bound to functional groups, such as fluorescent dyes or biotin. Using the halotag the probe can be visualized using brighter and more stable fluorescent molecules, with different excitation and emission spectrums than that of mCherry. Halotag detection is also compatible with super-resolution methods such as Storm imaging. Native gel and silver staining shows that $\alpha$GFPV$_H$H-Halo-ferritin can form particles even more efficiently than $\alpha$GFPV$_H$H-mCherry-ferritin.

To show that the $\alpha$GFPV$_H$H-mCherry-horse ferritin probe could label GFP tagged intracellular targets through $\alpha$GFPV$_H$H binding, an adenoviral protein E4-ORF3 marker was used as an example since it assembles huge fibers when it is transiently over-expressed. The large fiber morphology allows facile correlation of light and EM images, which facilitates EM analysis. ORF3-GFP expressing U2OS cells were transfected with $\alpha$GFPV$_H$H-mCherry-ferritin encoding plasmid and the cells were cultured with 500 μM FAC to iron-load the FIREnano probe. $\alpha$GFPV$_H$H-mCherry-ferritin successfully labeled ORF3-GFP fiber by fluorescent signal. Furthermore, iron core signals (dark round spots) originating from ferritin particles were identified in the ORF3-GFP fiber region by TEM (FIG. 11). Using Electron energy loss spectroscopy (EELS) and correlated light/EM tomography, the enrichment of iron element at the ferritin labeled ORF3 region was confirmed (FIGS. 12 and 13), indicating the dark particles are loaded with ferric oxide and their identity as ferritin particles.

The $\alpha$GFPV$_H$H-mCherry-horse ferritin probe was next used to observe a nuclear structure, namely telomeres. Telomeres are repetitive DNA sequences that bind to TRF1 and TRF2 and that form the shelterin complex to protect the chromosome end. A stable TRF1-GFP expressing Hela cell line was used in these assays. Telomere is a good target since each telomere contains around 500-3000 "TTAGGG" repeats, thus thousands of TRF1-GFP proteins are associated with each telomere. $\alpha$GFPV$_H$H-mCherry-horse ferritin was expressed in the stable TRF1-GFP expressing Hela cell line with 500 μM FAC to iron-load the FIREnano probe. Labeling of GFP-TRF1 telomeres was assessed fluorescence microscopy and EM. Remarkably, even in TEM thin sections, $\alpha$GFPV$_H$H-mCherry-horse ferritin particles can be readily observed as clusters, with each cluster representing one telomere DNA repeat and organization in the nucleus (FIG. 14). This shows that the strategy in using ferritin particles to label a specific gene locus was successful and enables direct observation of ferritin particles in EM images.

Additionally, assays were performed to show that the FIREnano probe can be combined with ChromEMT to visualize the structure of DNA and chromatin at telomeric repeats. ChromEMT combines electron microscopy tomography (EMT) with the (ChromEM) DNA labeling method that selectivity enhances the contrast of DNA. The technique is described in Ou et al ("ChromEMT: Visualizing 3D chromatin structure and compaction in interphase and mitotic cells," Science, 357(6349), 2017), which is incorporated by reference herein. ChromEMT exploits a fluorescent dye (DRAQ5), which binds to DNA, and upon excitation, catalyzes the deposition of diaminobenzidine polymers on the surface, enabling chromatin to be visualized with OsO4 in EM. Hela TRF1-GFP cells were transfected with $\alpha GFPV_HH$-mCherry-horse ferritin with 500 μM FAC in the media to iron-load the FIREnano probe, and 24 hours after transfection the cells were fixed with glutaraldehyde and stained with DRAQ5. Photo-oxidation was performed. The transmitted light image of post-photo-oxidation shows that DRAQ5 has photo-oxidized DAB monomer into DAB polymer that coated chromatin (FIG. 15). To reveal chromatin ultrastructure, Navminator was used to locate a telomere region and collected a 4-tilt EM tomography. Impressively, hundreds of ferritin particles were found in the background of DRAQ5 photo-oxidation, while the chromatin polymers are clearly visible by ChromEM labeling (FIG. 16). These results were repeated consistently in different cells and experiments, indicating the ferritin probe is compatible with ChromEM. The results of these assays provide, for the first time, in situ chromatin ultrastructure of a telomere.

In another example, the $\alpha GFPV_HH$-mCherry-horse ferritin probe was used to label Connexin43-GFP (Cx43-GFP), which is an important component in characteristic gap junction structure in the cytoplasm (FIG. 17). $\alpha GFPV_HH$-mCherry-ferritin successfully labeled and colocalized with Connexin43-GFP by fluorescent signal. Through 70 nm thin section TEM, iron-loaded ferritin particles were observed to co-localize with the Cx43-GFP with very uniform size of ~4-5 nm diameter from the $\alpha GFPV_HH$-mCherry-ferritin labeled Gap junction region. A corresponding assay was conducted using the $\alpha GFPV_HH$-halo-ferritin to label the Cx43-GFP gap junction region. Ferritin particles were detected by 4-tilt tomogram. The projection of 30 tomogram slices shows very clear alignment of many ferritin particles close to the gap junction, with their distance to the cell membrane all at comparable level.

To show that the FIREnano probe can be used to label chromosomal structures near regulatable genomes structures, the probes were assessed for labeling of LacO binding sites in a LacO/TetOn genomic insert. FIG. 18 provides an overview of the genomic insert. About 4 Mb sequences containing 200 gene arrays are artificially incorporated into chromosome 1 in the U2OS cell line. In each gene array, there are about 256 lacO binding sites, 96 Tet On promoter repeats, a mini CMV promoter, a CFP-SKL reporter which will locate in peroxisome in cytoplasm, and 24 MS2 stem loops, intron and exon. The CFP-SKL expression can be induced by adding doxycycline to the cell culture media. As depicted in the schematic, the FIREnano probe (e.g., $\alpha GFPV_HH$-Halo-horse ferritin) can be applied to label LacI-GFP which binds to LacO sequences in both silent (without doxycycline) and active (with doxycycline) state. The modified cell line was transfected with $\alpha GFPV_HH$-mCherryferritin encoding plasmid and the resulting FIREnano probe successfully label LacI-GFP in both silent (upper) and active (bottom) state (FIG. 18B).

The modified cell line depicted in FIG. 18 was transfected with $\alpha GFPV_HH$-mCherry-ferritin encoding plasmid and the cells were cultured with 500 μM FAC to iron-load the FIREnano probe and subsequently processed for light and EM analysis. Confocal and ChromEMT analysis show co-localization of the LacI-GFP and FIREnano probes, and labeling of the LacO genomic insert (FIG. 19). Labeling was unaffected by the presence or absence of Doxycycline (FIG. 20). However, as shown in FIG. 21-22, the FIREnano distribution under silent state (without doxycycline) indicated LacO array formed a compact sphere structure, wherein as the FIREnano distribution under active state indicated that the LacO array occupied a bigger area a more open structure than in silent state.

Further, these assays indicate that replacement of the $\alpha GFPV_HH$ targeting domain of the ferritin probe with other targeting domains can be used to label many different targets within cells, such as DNA, RNA, and proteins. For example, replacement of the $\alpha GFPV_HH$ targeting domain with dCas9 can facilitate labeling any genomic locus using the dCas9/TALEN technology. An increasing number of single chain antibodies that recognize different intracellular targets are available, such as anti-suntag single chain antibody (scFv), anti-mCherry nanobody. Similarly, RNA tags, including MS2, PP7 and lambda N22, can be recognized by RNA binding proteins, such as MCP, PCP, and N22p, which can be used as targeting domains. Further, PUF proteins bind to related sequence motifs in the 3' untranslated region (3'UTR) of specific target mRNAs, and therefore can also be used as targeting domains.

For targeting of particular DNA sequences, DNA binding proteins, such as transcription factors, can used as a targeting domain Further, a CRISPER/dCas9 fusion, or TALE fusion with a detection tags and a mammalian (e.g., horse) ferritin can be made. CRISPR uses a small guide (sg) RNA with a protospacer motif to target the Cas9 endonuclease protein to target DNA sequences. Mutations that ablate the nuclease activity of Cas9 (dCas9) enable it to be repurposed to label endogenous genomic loci. Transcription activator-like effector nucleases (TALEN) are restriction enzymes that can be engineered to cut specific sequences of DNA. They are made by fusing a TAL effector DNA-binding domain to a DNA cleavage domain (a nuclease which cuts DNA strands). Direct (dCas9-detection tag-ferritin; TALE-detection tag-ferritin) or indirect (dCas9-GFP; TALE-GFP: $\alpha GFPV_HH$-halo-ferritin) fusion allows the labeling any genomic sequences of interest.

Finally, to avoid transient transfection which might affect the ultrastructure of the cell and also to attain more even staining, the FIREnano probe can be expressed in cells using an adenovirus vector, which enables temporal control (hours post infection) as well as transcriptional control and downstream multiplexing of different labeling methods.

Materials and Methods

Cloning. To make the ferritin constructs, *E. coli* ferritin, *Helicobacter* ferritin, horse ferritin heavy chain, human ferritin heavy chain were human codon optimized. Different element/modules liken NLS, $\alpha GFPV_HH$, mCherry, halo tag, FLAG tag, GS linker were position adjusted and designed for whole ferritin fusion constructs. The whole encoding sequence (e.g., FLAG-NLS-$\alpha GFPV_HH$-halo-horse ferritin heavy chain) was synthesized through IDT and inserted into the multiple cloning sites of pcDNA3 through Gibson reaction.

Cell culture and transfection. HeLa TRF1-GFP, Hela Cx43-GFP, or U2OS cells were cultured in Dulbecco's Modified Eagle Medium (Invitrogen) supplemented with 10% fetal bovine serum. Transfection was performed in 35 mm MatTek dishes. 1 μg ferritin construct DNA was transfected (for 3.5 cm dishes) using X-tremeGENE (sigma). 24 hours after transfection, ferric ammonium citrate was added into cell culture media (final concentration: 500 μM). 48 hours after transfection, cells were fixed with 2.5% glutaraldehyde, and imaged, followed by sample embedding.

EM sample preparation. Cells were fixed with 2.5% EM grade glutaraldehyde (Electron Microscopy Sciences) in 5 mM CaCl2, 0.1M sodium cacodylate acid buffer, pH 7.4, at room temperature for 5 minutes with continued fixation for an additional hour on ice. From this step on, the cells were always treated either on ice or on a cold stage set at 4° C. All solutions were cold before applying to cells. After imaging, cells were stained for 30 minutes with a final concentration of 2% osmium tetroxide, 2 mM CaCl2, 1.5% potassium ferrocyanide (no performed when EELS was collected) in 0.15M sodium cacodylate acid buffer. After staining, cells were washed with double distilled water 5×2 minutes. Then cells were ethanol dehydrated in increasing concentration of ethanol (20-50-70-90-100-100% of ice cold ethanol with 3 minutes incubation for each concentration). Durcupan resin is prepared with the following ratio: components A:B:C: D=11:10:0.3:0.1 g. Dehydrated cells were infiltrated with solution containing 50% ethanol, 50% pre-mixed Durcupan resin for 30 minutes. The solution was replaced with 100% Durcupan resin and infiltrated for 30 minutes. This step was repeated 4 more times and the embedded cells placed in a vacuum oven for 48 hours (60° C.). For TEM, epoxy embedded cells were cut using a diamond knife into 70-80 nm sections. For tomography, embedded cells were cut into 250 nm sections.

FLAG-tagged ferritin purification. 24 μg FLAG-tagged ferritin constructs was transfected into 10 cm dishes using lipo2000 (ThermoFisher). 24 hours after transfection, ferric ammonium citrate was added into cell culture media (final concentration: 500 μM). 48 hours after transfection, cells were lysed using RIPA buffer. Clarified cell lysate was incubated with 50 μl ANTI-FLAG® M2 Magnetic Beads (Sigma) overnight. Beads was washed with RIPA buffer and PBS buffer 3 times each. 100 μl PBS with FLAG peptide (4 mg/ml) was incubated with beads for 3 hours for elute FLAG-ferritin off the beads. Eluted fractions were subjected to 3-12% Bis-Tris SDS-PAGE, or NativePAGE Bis-Tris Gels (ThermoFisher).

Silver staining. After SDS-PAGE and native gel running, silver staining was performed using Pierce™ Silver Stain Kit (ThermoFisher).

Prussian blue staining. After SDS-PAGE and native gel running, the gel was washed with water for 5 minutes. Prussian blue staining reagent was prepare: 2% ferrocyanide, 2% HCl (1-1.5 g potassium ferrocyanide, 43.7 ml ddH2O, 2.7 mL HCl). Gel was incubated in prussian blue staining for 1 hour in room temperature. Gel was washed with water frequently for 1 hour. Dissolve 12.5 mg of DAB powder in 500 uL of DMSO, add 1× TBS (50 mM Tris-Cl, pH 7.5 150 mM NaCl) till 50 mL, and 84 uL 30% H2O2. Gel was incubated in DAB buffer at room temperature until dark bands show up, then block the reaction with water.

Figure 3B:
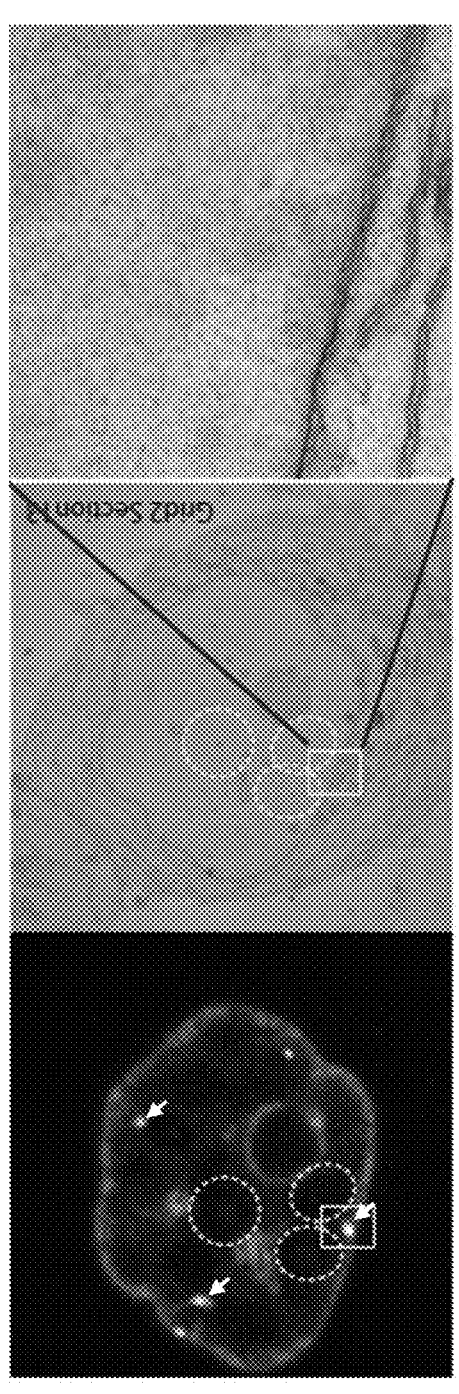

Tomography Data collection. Plastic sections were first carbon coated to improve their stability under the electron beam. 5 and 10 nm colloidal gold particles were deposited on both sides of the sections as fiducial markers for image alignment purpose. The tomography data was collected on a FEI Titan microscope operating at 300 kV with a 4K by 4K Gatan Ultrascan CCD camera, and the specimen was loaded in a rotation sample holder manufactured by Fischione Instruments (Model 2040). SerialEM was used for automatic tilt series acquisition to acquire all the micrographs at different specimen orientation. The 8-tilt data collection scheme is shown in FIG. 3B, where the specimen orientation is displayed for each tilt series and the order for which the tilt series is acquired is shown in numerical order in the middle panel. For each tilt series, adjustments are made to stage/sample height to ensure identical eucentric height, and magnification for all tilt series. The sequence of tilt series following the multilevel access scheme, which minimizes errors associated with sample shrinkage evenly across all tilt series. For each tilt series, images were acquired by rotating the sample holder from −60° to +60° with 1° increments.

It will be apparent that the precise details of the methods or compositions described may be varied or modified without departing from the spirit of the described embodiments. We claim all such modifications and variations that fall within the scope and spirit of the claims below.

We claim:

1. An isolated nucleic acid molecule encoding a fusion protein, the fusion protein comprising:

in an N- to C-terminal direction:
a nuclear localization sequence;
a targeting domain that specifically binds to an intracellular target antigen;
a detection tag; and
a horse ferritin heavy chain subunit; and
wherein the horse ferritin heavy chain subunit in the fusion protein self-assembles in mammalian cells to form a globular ferritin nanoparticle.

2. The nucleic acid molecule of claim 1, wherein the globular ferritin nanoparticle has ferroxidase activity and stores ferric oxide.

3. The nucleic acid molecule of claim 1, wherein the targeting domain is a single chain antibody that specifically binds to the intracellular target antigen.

4. The nucleic acid molecule of claim 1, wherein the intracellular target antigen is one of DNA, RNA, or chromatin.

5. The nucleic acid molecule of claim 1, wherein the targeting domain is an anti-GFP scFv, or an anti-GFP $V_H$H; or comprises or consists of the amino acid sequence set forth as SEQ ID NO: 45.

6. The nucleic acid molecule of claim 1, wherein the targeting domain is an MS2 stem loop binding protein, a lambda N22 RNA binding protein, a PP7 RNA stem loop coat protein, PUFa, or PUFb; or comprises or consists of the amino acid sequence set forth as any one of SEQ ID NOs: 27-29 and 32-33.

7. The isolated nucleic acid molecule of claim 1, wherein the detection tag is detectable in cells by fluorescence microscopy.

8. The nucleic acid molecule of claim 1, wherein the detection tag is selected from a fluorescent protein or a fluorescent dye binding protein.

9. The nucleic acid molecule of claim 8, wherein the fluorescent protein comprises mCherry, and/or the fluorescent dye binding protein comprises halotag.

10. The nucleic acid molecule of claim 8, wherein the detection tag comprises or consists of the amino acid sequence set forth as SEQ ID NO: 41.

11. The nucleic acid molecule of claim 1, wherein the horse ferritin subunit comprises the amino acid sequence set forth as SEQ ID NO: 21.

12. The nucleic acid molecule of claim 1, wherein the detection tag is linked to the horse ferritin subunit by a glycine-serine peptide linker.

13. The nucleic acid molecule of claim 12, wherein the glycine-serine peptide linker comprises or consists of the amino acid sequence set forth as SEQ ID NO: 37 (GGGSGGGSGGGS).

14. The nucleic acid molecule of claim 1, wherein the fusion protein comprises the amino acid sequence set forth as SEQ ID NO: 25.

15. The nucleic acid molecule of claim 1, operably linked to a promoter.

16. An expression vector comprising the nucleic acid molecule of claim 14.

17. A method of detecting the location of a target antigen in a mammalian cell, comprising:

expressing the nucleic acid molecule of claim 1 in a mammalian host cell; and
detecting the location of the detection tag and the ferritin nanoparticle in the mammalian host cell using fluorescence microscopy and electron microscopy, respectively, to detect the location of the target antigen.

18. The method of claim 17, wherein the mammalian host cell is incubated in growth medium comprising transferrin and/or ferric ammonium citrate.

19. The nucleic acid molecule of claim 1, wherein the targeting domain is an anti-suntag scFv; or comprises or consists of the amino acid sequence set forth as SEQ ID NO: 30.

20. The nucleic acid molecule of claim 1, wherein the targeting domain is FRB, or FKBP; or comprises or consists of the amino acid sequence set forth as SEQ ID NO: 34 or 35.

21. The nucleic acid molecule of claim 1, wherein the targeting domain is dSpCas9, or dCas13d; or comprises or consists of the amino acid sequence set forth as SEQ ID NO: 36.

22. The nucleic acid molecule of claim 1, wherein the intracellular target antigen is in the nucleus.

23. The nucleic acid molecule of claim 8, wherein the detection tag comprises or consists of the amino acid sequence set forth as SEQ ID NO: 39.

24. The nucleic acid molecule of claim 1, wherein the fusion protein comprises the amino acid sequence set forth as SEQ ID NO: 26.

25. The nucleic acid molecule of claim 1, wherein the fusion protein comprises the amino acid sequence set forth as SEQ ID NO: 43.

26. An expression vector comprising the nucleic acid molecule of claim 24.

27. An expression vector comprising the nucleic acid molecule of claim 25.

28. The fusion protein encoded by the nucleic acid molecule of claim 1.

29. A ferritin nanoparticle comprising the fusion protein of claim 28.

30. The ferritin nanoparticle of claim 29, further comprising a ferritin light chain.

\* \* \* \* \*